US006846481B1

(12) United States Patent
Gaertig et al.

(10) Patent No.: US 6,846,481 B1
(45) Date of Patent: Jan. 25, 2005

(54) RECOMBINANT EXPRESSION OF HETEROLOGOUS NUCLEIC ACIDS IN PROTOZOA

(75) Inventors: Jacek Gaertig, Athens, GA (US); Harry W. Dickerson, Jr., Athens, GA (US); Theodore G. Clark, Ithaca, NY (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/498,612

(22) Filed: Feb. 4, 2000

Related U.S. Application Data

(60) Provisional application No. 60/131,121, filed on Apr. 27, 1999, provisional application No. 60/124,905, filed on Mar. 17, 1999, provisional application No. 60/122,372, filed on Mar. 2, 1999, and provisional application No. 60/118,634, filed on Feb. 4, 1999.

(51) Int. Cl.[7] .......................... A01N 63/00; A01N 65/00; C12P 21/06; C12N 1/20; C12N 15/00
(52) U.S. Cl. .................. 424/93.1; 424/93.2; 424/93.21; 435/69.1; 435/252.3; 435/320.1; 435/325
(58) Field of Search ........................ 536/23.7; 435/471, 435/69.1, 252.3, 320.1, 325; 424/93.1, 93.2, 93.21

(56) References Cited

U.S. PATENT DOCUMENTS

| | | | |
|---|---|---|---|
| 4,309,416 A | 1/1982 | Gratzek et al. | |
| 5,661,032 A | 8/1997 | Miller et al. | |
| 5,695,965 A | 12/1997 | Stuart et al. | |
| 5,780,448 A | 7/1998 | Davis | |
| 6,087,124 A | 7/2000 | Steinbrück et al. | |

FOREIGN PATENT DOCUMENTS

| | | |
|---|---|---|
| EP | 0773 295 A2 | 5/1997 |
| WO | WO 81/00812 | 4/1981 |
| WO | WO 90/14428 | 11/1990 |
| WO | WO 98/01572 | 1/1998 |

OTHER PUBLICATIONS

Endoh (JPN. J. Genet . vol. 69, No. 4, pp 377–383), 1994.*
Ellis et al. "Vaccines" Chpater 29 published by W.B. Saunders Company (Philadelphia) 1998.*
Hai et al. PNAS 1997 vol. 94 pp. 1310–1315.*
Gaertig et al. PNAS 1994 vol. 94 pp. 4549–4553.*
Nossal, "Vaccines," *Fundamental Immunology, Fourth Edition*, Ed. W. Paul, Chapter 42, pp. 1387–1425 (Lippincott–Raven, Philadelphia, 1999).
Paoletti, "Applications of pox virus vectors to vaccination: An update," *Proc. Natl. Acad. Sci. USA*, 93:11349–11353 (1996).
Sanford et al., "An Improved, Helium–Driven Biolistic Device," *Technique*, 3(1):3–16 (1991).

Alexander, "A New Immobilization Test for *Tetrahymena pyriformis*," *Trans. Amer. Microsc. Soc.*, 86(4):421–427 (1967).
Al–Qahtani et al., "A 5' untranslated region which directs accurate and robust translation by prokaryotic and mammalian ribosomes," *Nuc. Acids Res.*, 24(6):1173–1174 (1996).
Areerat, *The Immune Response of Channel Catfish, Ictalurus punctatus(Rafinesque)*, to *Ichthyophthirius multifiliis*, Master's thesis, Auburn University, 47 pages (1974).
Berg et al., "The Galvanization of Biology: A Growing Appreciation for the Roles of Zinc," *Science*, 271:1081–1085 (1996).
Blomberg et al., "Regulatory Sequences for the Amplification and Replication of the Ribosomal DNA Minichromosome in *Tetrahymena thermophila*," *Mol. Cell. Biol.*, 17(12):7237–7247 (1997).
Bolduc et al., "β–Tubulin mutants of the unicellular green alga *Chlamydomonas reinhardtii*," *Proc. Natl. Acad. Sci. USA*, 85(1):131–135 (1988).
Boothroyd et al., eds., *Molecular Approaches to Parasitology*, John Wiley & Sons, New York, Title page, publication page and table of contents only, 4 pages (1995).
Brosius et al., "Gene Organization and Primary Structure of a Ribosomal RNA Operon form *Escherichia coli*," *J. Mol. Biol.*, 148(2):107–127 (1981).
Brunk et al., "Analysis of Nuclei from Exponentially Growing and Conjugated *Tetrahymena thermophila* Using the Flow Microfluorimeter," *Exp. Cell Res.*, 162:390–400 (1986).
Brunk et al., "Characterization of the promoter region of *Tetrahymena* genes," *Nuc. Acids. Res.*, 18(2):323–329 (1990).
Brunk, "Ciliates display promise for foreign gene expression," *Nature Biotechnology*, 17:424–425 (May, 1999).
Burkart et al., "Immunization of channel catfish, *Ictalurus punctatus* Rafinesque, against *Ichthyophthirius multifiliis* (Fouquet) killed versus live vaccines," *J. Fish Dis.*, 13:401–410 (1990).
Caras et al., "Cloning of decay–accelerating factor suggests novel use of splicing to generate two proteins," *Nature*, 325:545–549 (1987).

(List continued on next page.)

*Primary Examiner*—Mark Navarro
(74) *Attorney, Agent, or Firm*—Mueting Raasch & Gebhardt

(57) ABSTRACT

The ciliated protozoan Tetrahymena exemplifies a recombinant system for the expression of heterologous nucleic acids, preferably on the plasma membrane surface. Integration of a heterologous nucleic acid into the β-tubulin gene, BTU1, of a paclitaxel-sensitive *T. thermophila* mutant that possesses btu1-1K350M β-tubulin allele allows screening for transformants using negative selection, as transformants have restored paclitaxel resistance. Transgenic ciliated protozoa of the invention can serve as live vaccines. For example, transgenic Tetrahymena expressing *Ichthyophthirius multifiliis* i-antigen protein on their surface are effective vehicles for vaccination of freshwater fish against infection by *I. multifiliis*.

44 Claims, 37 Drawing Sheets

OTHER PUBLICATIONS

Caras et al., "Signal Peptide for Protein Secretion Directing Glycophospholipid Membrane Anchor Attachment," *Science*, 243(4895):1196–1198 (1989).

Caron et al., "Molecular Basis of Surface Antigen Variation in Patramecia," *Ann. Rev. Microbiol.*, 43:23–42 (1989).

Caruthers, "New Methods for Chemically Synthesizing Deoxyoligonucleotides,," *Methods of DNA and RNA Sequencing*, Weissman, ed., Praeger Publishers, New York, Title Page, publication page and pp. 1–22 (1983).

Cassidy–Hanley et al., "Germline and Somatic Transformation of Mating *Tetrahymena thermophila* by Particle Bombardment," *Genetics*, 146:135–147 (1997).

Catterall et al., "Nucleotide sequence homology at 12 intron––exon junctions in the chick ovalbumin gene," *Nature*, 275(5680):510–513 (1978).

Chen et al., "A *Giardia duodenalis* gene encoding a protein with multiple repeats of a toxin homologue," *Parasitol.*, 111(4):423–431 (1995).

Clark et al., "In vitro response of *Ichthyophthirius multifiliis* to sera from immune channel catfish," *J. Fish Biol.*, 31(Supplement A):203–208 (1987).

Clark et al., "Immune Response of Channel Catfish to Ciliary Antigens of *Ichthyophthirius multifiliis*" *Devel. Comp. Immunol.*, 12(3):581–594 (1988).

Clark et al., "Differential Expression of Membrane Antigen Genes in *I. Multifiliis*, a Protozoan Pathogen of Fish," Abstract and Poster, Annual Meeting on Molecular Parasitology, Woods Hole, MA, Sep. 9–12, 7 pages (1990).

Clark et al., "Developmental expression of surface antigen genes in the parasitic ciliate *Ichthyophthirius multifiliis*, " *Proc. Natl. Acad. Sci. USA*, 89:6363–6367 (1992).

Clark et al., "Surface Immobilization Antigens of *Ichthyophthirius mutlifiliis*: Their Role in Protective Immunity," *Ann. Rev. Fish Dis.*, 5:113–131 (1995).

Clark et al., "Surface antigen cross–linking triggers forced exit of a protozoan parasite from its host," *Proc. Natl. Acad. Sci. USA*, 93(13):6825–6829 (1996).

Clark et al., "Antibody–meidated Effects on Parasite Behavior: Evidence of a Novel Mechanism of Immunity against a Parasitic Protist," *Parasitol. Today*, 13(12):477–480 (1997).

Clark, "Molecular Approaches to the Control of Ichthyophthirius Infection," Abstract, Grant for Oct. 25, 1997 through Jun. 30, 2002, Cooperating Schools of Veterinary Medicine GEOV, proj. No. NYCV–433–391 (Available on–line on or before Jul. 19, 1998).

Clark et al., "The gene for an abundant parasite coat protein predicts tandemly repetitive metal binding domains," *Gene*, 229(1–2):91–100 (Mar. 18, 1999).

Cohen et al., "Expression of a Ciliate Gene in *Escherichia coli* Using a Suppressor tRNA to Read the UAA and UAG Glutamine Codons," *J. Mol. Biol.*, 216:189–194 (1990).

Cross et al., "Ichthyophthiriasis in carp, *Cyprinus carpio* L: fate of parasites in immunized fish," *J. Fish Dis.*, 15:497–505 (1992).

Cupples et al., "Isolation and characterization of the actin gene from *Tetrahymena thermophila*," *Proc. Natl. Acad. Sci. USA*, 83(14):5160–5164 (1986).

Deak et al., "Sequence, codon usage and cysteine periodicity of the *SerH1* gene and in the encoded surface protein of *Tetrahymena thermophila*," *Gene*, 164:163–166 (1995).

Dempsey et al., "C3d of Complement as a Molecular Adjuvant: Bridging Innate and Acquired Immunity," *Science*, 271:348–350 (1996).

Deng et al., "Site–Directed Mutagenesis of Virtually Any Plasmid by Eliminating a Unique Site," *Anal. Biochem.*, 200:81–88 (1992).

Dickerson et al., "*Ichthyophthirius multifiliis* Has Membrane–Associated Immobilization Antigens," *J. Protozool.*, 36(2):159–164 (1989).

Dickerson et al., "Molecular Approaches to the Prevention of Ichthyophthirius Infection," Abstract, Grant for Sep. 1, 1992 through Aug. 31, 1996, Competitive Research Grants Office (NRI) GEOV, grant No. 92–37204–7838 (Available on–line on or before Jul. 19, 1998).

Dickerson et al., "Serotypic Variation Among Isolates of *Ichthyophthirius multifiliis* Based on Immobilization," *J. Euk. Microbiol.*, 40(6):816–820 (1993).

Dickerson et al., "Vaccination against Ich," *Aquaculture*, 127(2–3):278–280 (1994).

Dickerson et al., "Molecular Approaches Toward the Control of Ichthyophthirius Infection," CRIS report, NRI competitive grant No. 95–37204–2139, Sep. 1, 1995 to Aug. 31, 2000, 5 pages (1995) (Available on–line on or before Jul. 19, 1998).

Dickerson et al., "Immune Response of Fishes to Ciliates," *Ann. Rev. Fish Dis.*, 6:107–120 (1996).

Dickerson et al., "Display of an Ichthyophthirius I–Antigen on the Surface of Transformed *Tetrahymena thermophila* for Use as a Novel Vaccine in Fish," Abstract, Ann. Meeting, Conference of Research Workers in Animal Diseases, Nov. 8–10, Chicago (1998).

Englund, "The Structure and Biosynthesis of Glycosyl Phosphatidylinositol Protein Anchors," *Ann. Rev. Biochem.*, 62:121–138 (1993).

Ferguson, "What Can GPI Do for You?" *Parasitol. Today*, 10(2):48–52 (1994).

Frohman, "RACE: Rapid Amplification of cDNA Ends," *PCR Protocols: A Guide to Methods and Applications*, Innis, et al., eds., Academic Press, San Diego, Title page, publication page, table of contents and pp. 28–38 (1990).

Frohman, "RACE: Rapid Amplification of Complementary DNA Ends for Generation of Full–Length Complementary DNAs: Thermal RACE," *Meth. Enzymol.*, 218:340–356 (1993).

Gaertig et al., "Perspectives on Tubulin Isotype Function and Evolution Based on the Observation that *Tetrahymena thermophila* Microtubules Contain a Single α– and β–Tubulin," *Cell Mot. Cytoskel.*, 25:243–253 (1993).

Gaertig et al., "Electroporation–mediated replacement of a positively and negatively selectable β–tubulin gene in *Tetrahymena thermophila*," *Proc. Natl., Acad. Sci. USA*, 91:4549–4553 (1994).

Gaertig et al., "High frequency vector–mediated transformation and gene replacement in Tetrahymena," *Nuc. Acids Res.*, 22(24):5391–5398 (1994).

Gaertig et al., "Acetylation of Lysine 40 in α–tubulin is Not Essential in *Tetrahymena thermophila*," *J. Cell. Biol.*, 129(5):1301–1310 (1995).

Gaertig, "New approaches for gene knockout, transgene expression and surface display in the ciliate *Tetrahymena thermophilia*," *Jap. J. of Protozool.*, 32(1):11–19 (Mar. 13, 1999).

Gaertig et al., "Surface display of a parasite antigen in the ciliate *Tetrahymena thermophila*," *Nature Biotechnology*, 17(5):462–465 (May, 1999).

Gall, ed., *The Molecular Biology of Ciliated Protozoa*, Academic Press, Inc., Orlando, Title page, publication page and table of contents only, 4 pages (1986).

Garg et al., "Delivery by *Trypanosoma cruzi* of Proteins into the MHC Class 1 Antigen Processing and Presentation Pathway," *J. Immunol.*, 158:3293–3302 (1997).

Glover, ed., *DNA Cloning, vol. I: a practical approach*, IRL Press, Oxford, Title page, publication page and table of contents only, 8 pages (1985).

Glover, ed., *DNA Cloning, vol. II: a practical approach*, IRL Press, Oxford, Title page, publication page and table of contents only, 7 pages (1985).

Gorovsky, "Macro– and Micronuclei of *Tetrahymena pyriformis*: A Model System for Studying the Structure and Function of Eukaryotic Nuclei," *J. Protozool.*, 20(1):19–25 (1973).

Goven et al., "Protection of channel catfish, *Ictalurus punctatus* Rafinesque, against *Ichthyophthirius multifiliis* Fouquet by immunization," *J. Fish Biol.*, 17:311–316 (1980).

Gower et al., "Alternative Splicing Generates a Secreted Form of N–CAM in Muscle and Brain," *Cell*, 55(6):955–964 (1988).

Grossman et al., eds., *Methods in Enzymology vol. 65, Nucleic Acids Part I*, Academic Press Inc., New York, Title page, publication page and table of contents only, 8 pages (1980).

Gubler et al., "Second–Strand cDNA Synthesis: mRNA Fragments as Primers," *Meth. Enzymol.*, 152:330–335 (1987).

Haddad et al., "Analysis of exocytosis mutants indicates close coupling between regulated secretion and transcription activation in Tetrahymena," *Proc. Natl. Acad. Sci. USA*, 94(20):10675–10680 (1997).

Hames et al., eds., *Nucleic acid hybridization: a practical approach*, IRL Press, Oxford, Title page, publication page and table of contents only, 8 pages (1985).

He et al., "Protection of goldfish against *Ichthyophthirius multifiliis* by immunization with a recombinant vaccine," *Aquacult.*, 158:1–10 (1997).

Hedrick et al., "Passive Transfer of Sera with Antivirus Neutralizing Activity from Adult Channel Catfish Protects Juveniles from Channel Catfish Virus Disease," *Trans. Amer. Fish Soc.*, 116:277–281 (1987).

Hines et al., "Ichthyophthiriasis in the mirror carp *Cyprinus carpio* (L.) V. Acquired immunity," *J. Fish Biol.*, 6:373–378 (1974).

Hopp et al., "A Short Polypeptide Marker Sequence Useful for Recombinant Protein Identification and Purification," *Biotechnology*, 6:1204–1210 (1988).

Hünseler et al., "Genetic Characterization of the Secretory Mutant MS–1 of *Tetrahymena thermophila*: Vacuolarization and Block in Secretion of Lysosomal Hydrolases Are Caused by a Single Gene Mutation," *Dev. Genet.*, 13:167–173 (1992).

Innis et al., "Expression, Glycosylation, and Secretion of an *Aspergillus* Glucoamylase by *Saccharomyces cerevisiae*," *Science*, 228:21–26 (1985).

Jones et al., "Oral Delivery of Micro–Encapsulated DNA Vaccines," *Dev. Biol. Stand.*, 92:149–155 (1998).

Kahn et al., "Transformation of *Tetrahymena thermophila* by microinjection of a foreign gene," *Proc. Natl. Acad. Sci. USA*, 90(20):9295–9299 (1993).

Kavenoff et al., "Chromosome–Sized DNA Molecules from Drosophila," *Chromosoma*, 41:1–27 (1973).

Kiy et al., "Continuous high–cell–density fermentation of the ciliated protozoon Tetrahymena in a perfused bioreactor," *Appl. Microbiol. Biotechnol.*, 38:141–146 (1992).

Krieg et al., "CpG motifs in bacterial DNA trigger direct B–cell activation." *Nature*, 374:546–549 (1995).

Krieg et al., "The role of CpG dinucleotides in DNA vaccines," *Trends Microbiol.*, 6(1):23–27 (1998).

Krug et al., "First–Strand cDNA Synthesis Primed with Oligo(dT)," *Meth. Enzymol.*, 152:316–325 (1987).

La Flamme et al., "Expression of mammalian cytokines by *Trypanosoma cruzi* indicates unique signal sequence requirements and processing," *Mol. Biochem. Parasitol.*, 75:25–31 (1995).

Lambris et al., "Third Component of Trout Complement," *J. Immunol.*, 151(11):6123–6134 (1993).

Lee et al., "Missense Mutations at Lysine 350 in $\beta$2–Tubulin Confer Altered Sensitivity to Microtubule Inhibitors in Chlamydomonas," *Plant Cell*, 2(11):1051–1057 (1990).

Leong et al., "DNA–polycation nanospheres as non–viral gene delivery vehicles," *J. Controlled Release*, 53:183–193 (1998).

Lin et al., "Purification and Partial Characterization of Immobilization Antigens from *Ichthyophthirius multifiliis*," *J. Protozool.*, 39(4):457–463 (1992).

Lin et al., "Passive Immunization of Channel Catfish (*Ictalurus punctatus*) against the Ciliated Protozoan Parasite *Ichthyophthirius multifiliis* by Use of Murine Monoclonal Antibodies," *Infect. Immun.*, 64(10):4085–4090 (1996).

Løvlie et al., "Molecular evidence for somatic recombination in the ribosomal DNA of *Tetrahymena thermophila*," *Proc. Natl. Acad. Sci. USA*, 85:5156–5160 (1988).

MacRae, "Tubulin post–translational modifications: Enzymes and their mechanisms of action," *Eur. J. Biochem.*, 244:265–278 (1997).

Martindale, "Codon Usage in Tetrahymena and Other Ciliates," *J. Protozool.*, 36(1):29–34 (1989).

Miller, *Experiments in Molecular Genetics*, Cold Spring Harbor Laboratory, Cold Spring Harbor, New York, Title page, publication page and table of contents only, 8 pages (1972).

Nash et al., "Variant–specific surface proteins of *Giardia lamblia* are zinc–binding proteins," *Proc. Natl. Acad. Sci. USA*, 90(12):5489–5493 (1993).

Nielsen et al., "Identification of prokaryotic and eukaryotic signal peptides and prediction of their cleavage sites," *Prot. Engin.*, 10:1–15 (1996).

Old et al., *Principles of Gene Manipulation, An Introduction to Genetic Engineering*, University of California Press, Berkeley, Title page, publication page and table of contents only, 3 pages (1981).

Pan et al., "Tandem repeats of the 5' non–transcribed spacer of Tetrahymena rDNA function as a high copy number autonomous replicons in the macronucleus but do not prevent rRNA gene dosage regulation," *Nuc. Acids Res.*, 23(9):1561–1569 (1995).

Pan et al., "Replication of an rRNA Gene Origin Plasmid in the *Tetrahymena thermophila* Macronucleus is Prevented by Transcription through the Origin from an RNA Polymerase I Promoter," *Mol. Cell. Biol.*, 15(6):3372–3381 (1995).

Parker, *Studies on the Natural History of Ichthyophthirius multifiliis Fouquet 1876, an Ectoparastic Ciliate of Fish*, Ph.D. Dissertation, The University of Maryland, College Park, MD, 94 pages (1965).

Peters–Regehr et al., "Primary Structure and Origin of a Predator Released Protein that Induces Defensive Morphological Changes in Euplotes," *Europ. J. Protistol.*, 33:389–395 (1997).

Prat et al., "Nucleotide Sequence of the *Paramecium primaurelia* G Surface Protein, a Huge Protein with a Highly Periodic Structure," *J. Mol. Biol.*, 189(1):47–60 (1986).

Preer, "Surface Antigens of Paramecium," *The Molecular Biology of Ciliated Protozoa*, Gall, ed., Academic Press, Orlando, Title page, publication page, table of contents and pp. 301–339 (1986).

Prescott, "The DNA of Ciliated Protozoa," *Microbiol. Rev.*, 58(2):233–267 (1994).

Raftery et al, "Systematic alterations in the anticodon arm make $tRNA^{Glu}$–$Su_{OC}$ a more efficient suppressor," *EMBO J.*, 6(5):1499–1506 (1987).

Redeker et al., "Polyglycylation of Tubulin: A Posttranslational Modification in Axonemal Microtubules," *Science*, 266:1688–1691 (1994).

Reisner et al., "Concerning the Tertiary Structure of the Soluble Surface Proteins of Paramecium," *Biochemistry*, 8(11):4637–4644 (1969).

Reymond et al., "Anchoring of an Immunogenic *Plasmodium falciparum* Circumsporozoite Protein on the Surface of *Dictyostelium discoideum*," *J. Biol. Chem.*, 270(21):12941–12947 (1995).

Roy et al., "Oral gene delivery with chitosan–DNA nanoparticles generates immunologic protection in a murine model of peanut allergy," *Nature Med.*, 5(4):387–391 (Apr., 1999).

Rusch et al., "Protein transport via amino–terminal targeting sequences: common themes in diverse systems (Review)," *Mol. Membr. Biol.*, 12(4):295–307 (1995).

Rusconi et al., "The anticodon is the signal sequence for mitochondrial import of glutamine tRNA in Tetrahymena," *Genes Dev.*, 10(22):2870–2880 (1996).

Sambrook et al., *Molecular Cloning: A Laboratory Manual, Second Edition*Books 1–3, Cold Spring Harbor Laboratory Press, Cold Spring Harbor, New York, Title page and table of content only, 29 pages (1989).

Saraste et al., "The P–loop—a common motif in ATP– and GTP–binding proteins," *Trends Biochem. Sci.*, 15:430–434 (1990).

Schleif et al., *Practical Methods in Molecular Biology*, Springer–Verlag, New York, Title page, publication page and tabel of contents only, 7 pages (1981).

Seeber et al., "Analysis of *Toxoplasma gondii* stably transfected with a transmembrane variant of its major surface protein, SAG1," *J. Cell Sci.*, 111:23–29 (1998).

Setlow et al., eds., *Genetic Engineering: Principles and Methods, vol. 1*, Plenum Press, New York, Title page, publication page and table of contents only, 4 pages (1979).

Smith et al., "Characterization of the T, L, I, S, M and P Cell Surface (Immobilization) Antigens of *Tetrahymena thermophila*: Molecular Weights, Isoforms, and Cross–Reactivity of Antisera," *J. Protozool.*, 39(3):420–428 (1992).

Spangler et al., "The Nucleotide Sequence of the 17 S Ribosomal RNA Gene of *Tetrahymena thermophila* and the Identification of Point Mutations Resulting in Resistance to the Antibiotics Paromomycin and Hygromycin," *J. Biol. Chem.*, 260(10):6334–6340 (1985).

Stemmer et al., "Single–step assembly of a gene and entire plasmid from large numbers of oligodeoxyribonucleotides," *Gene*, 164:49–53 (1995).

Suggs et al., "Use of synthetic oligonucleotides as hybridization probes: Isolation of cloned cDNA sequences for human $\beta_2$–microglobulin," *Proc. Natl. Acad. Sci. USA*, 78(11):6613–6617 (1981).

Sundermann et al., "Recognition of Prey by Suctoria: The Role of Cilia," *J. Protozool.*, 33(4):473–475 (1986).

Sunyer et al., "Multiple forms of complement C3 in trout that differ in binding to complement activators," *Proc. Natl. Acad. Sci. USA*, 93:8546–8551 (1996).

Tobin et al., "Transfected Leishmania Expressing Biologically Active IFN–Γ," *J. Immunol.*, 150(11):5059–5069 (1993).

Tondravi et al., "Transformation of *Tetrahymena thermophila* by microinjection of ribosomal RNA genes," *Proc. Natl. Acad. Sci. USA*, 83:4369–4373 (1986).

Tondravi et al., "Molecular Characterization of SerH3, a *Tetrahymena thermophila* Gene Encoding a Temperature–Regulated Surface Antigen," *Mol. Cell. Biol.*, 10(11):6091–6096 (1990).

Viele et al., "Adoptive transfer of immunity against *Vibrio anguillarum* in rainbow trout, *Salmo gairdneri* Richardson, vaccinated by the immersion method," *J. Fish Biol.*, 17:379–386 (1980).

Williams et al., "Recombinant glycoprotein production in the slime mould *Dictyostelium discoideum*," *Curr. Opin. Biotechnol.*, 6:538–542 (1995).

Wirtz et al., "Inducible Gene Expression in Trypanosomes Mediated by a Prokaryotic Repressor," *Science*, 268:1179–1183 (1995).

Woo, "Immunization Against Parasitic Diseases of Fish," *Dev. Biol. Stand.*, 90:233–241 (1997).

Wu, ed., *Methods in Enzymology vol. 68 Recombinant DNA*, Academic Press Inc, New York, Title page, publication page and table of contents only, 6 pages (1979).

Wu et al., eds., *Methods in Enzymology vol. 100 Recombinant DNA Part B*, Academic Press Inc, New York, Title page, publication page and table of contents only, 5 pages (1983).

Wu et al., eds., *Methods in Enzymology vol. 101 Recombinant DNA Part C*, Academic Press Inc, New York, Title page, publication page and table of contents only, 6 pages (1983).

Xu et al., "Analysis of the Soluble and Membrane–bound Immobilization Antigens of *Ichthyophthirius multifiliis*," *J. Euk. Microbiol.*, 42(5):558–564 (1995).

Yao et al., "Accurate Processing and Amplification of Cloned Germ Line Copies of Ribosomal DNA Injected into Developing Nuclei of *Tetrahymena thermophila*," *Mol. Cell. Biol.*, 9(3):1092–1099 (1989).

Yao et al., "Transformation of Tetrahymena to cycloheximide resistance with a ribosomal protein gene through sequence replacement," *Proc. Natl. Acad. Sci. USA*, 88(21):9493–9497 (1991).

Young et al., "Efficient isolation of genes by using antibody probes," *Proc. Natl. Acad. Sci. USA*, 80:1194–1198 (1983).

Yu et al., "Circular ribosomal DNA plasmids transform *Tetrahymena thermophila* by homologous recombination with endogenous macronuclear ribosomal DNA," *Proc. Natl. Acad. Sci. USA*, 85:5151–5155 (1988).

Yu et al., "Transformation of *Tetrahymena thermophila* with a mutated circular ribosomal DNA plasmid vector," *Proc. Natl. Acad. Sci. USA*, 86:8487–8491 (1989).

Zhang et al., "Cysteine–Dependent Zinc Building by Membrane Proteins of *Giardia lamblia*," *Infect. Immun.*, 61(2):520–524 (1993).

* cited by examiner $Fig.\ 2a_1$ $Fig.\ 2a_2$ $Fig.\ 2a_3$ $Fig.\ 2a_4$ $Fig.\ 2a_5$ $Fig.\ 2a_6$ $Fig.\ 2a_7$ $Fig.\ 2a_8$ $Fig.\ 2a_9$ $Fig.\ 2a_{10}$ $Fig.\ 2a$

```
                     Tfi I                    Mse I           Apo I      MnI I         Alu I
                     Hinf I                     |               |          |             |
ATCCTTTACGAAGATCAAGTTGCTACTTTAATGAATAATAGAATTTGAGGTAGAGCTAAAATGAGAGATATAGTAATGCTAT  640
TAGGAAATGCTTAGTTCAACGATGAAATTACTTATTATCTTAAACTCCATCTCGATTTTACTCTCTATATCATTACGATA
              *              *              *             *              *             *
               |570                         |586           |*            |             *
               570                          586            599          605            612

Mbo II                       Mse I
                                                        Ear I                        Ase I
                                                          |                            ||
TGGATTATATTGGTTTGTATTGATGGTTTTCTTTGGTAAATGAATGATATAAATGAAGAGTGGCAATAAAATTAATTG  720
ACCTAATATAACCAAACATAACTACCAAAAGAAGAAACCATTTACTTACTATATTTACTTCTCACCGTTATTTAATTAAC
         *              *              *              *         |*|             *
                                                                 697            713
                                                                 697            714

Mbo II                                               Mse I
                    Ear I                              Mse I              Dra I         Mse I
                     |                      Apo I        |                 ||           Apo I
MseI                 |                        |          |                 ||             |
 |                   |                        |          |                 ||             |
AAATTGAATGAAAAAATGAATAAGAAGAGTATAAATTAAGAATTTATTTTTGAATTTTTAAAATTTAAAATTTTAAT  800
TTTAACTTACTTTTTTACTTATTCTTCTCATATTTAATTCTTAAATAAAAACTTAAAATTTAAAATTTTAAAAATTA
  *              |*|         *             *            *      |   |        *
                 747          775                              781  786     790   796
                 752                                                787
                 752
```

Fig. 2a₃

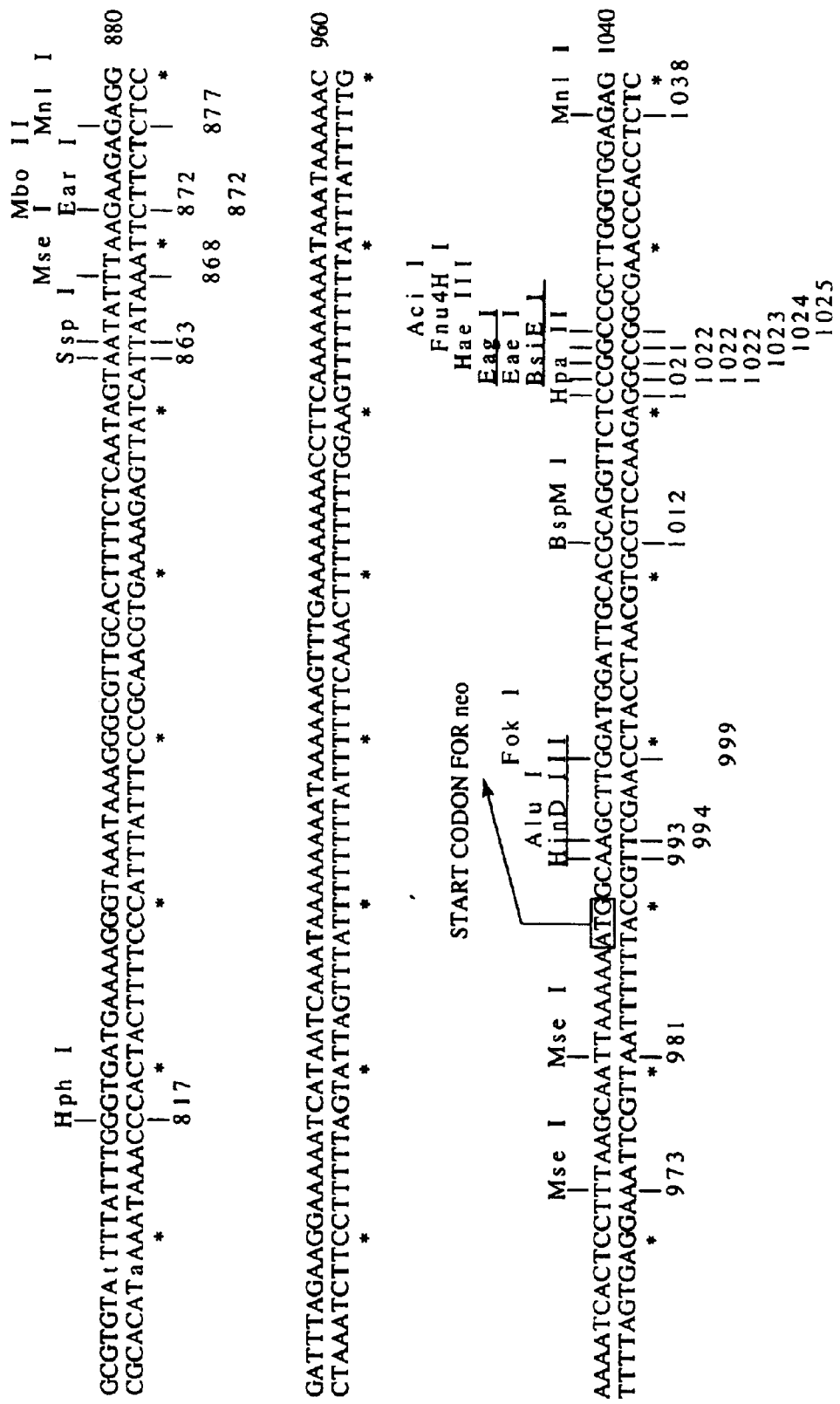
Fig. 2a₄

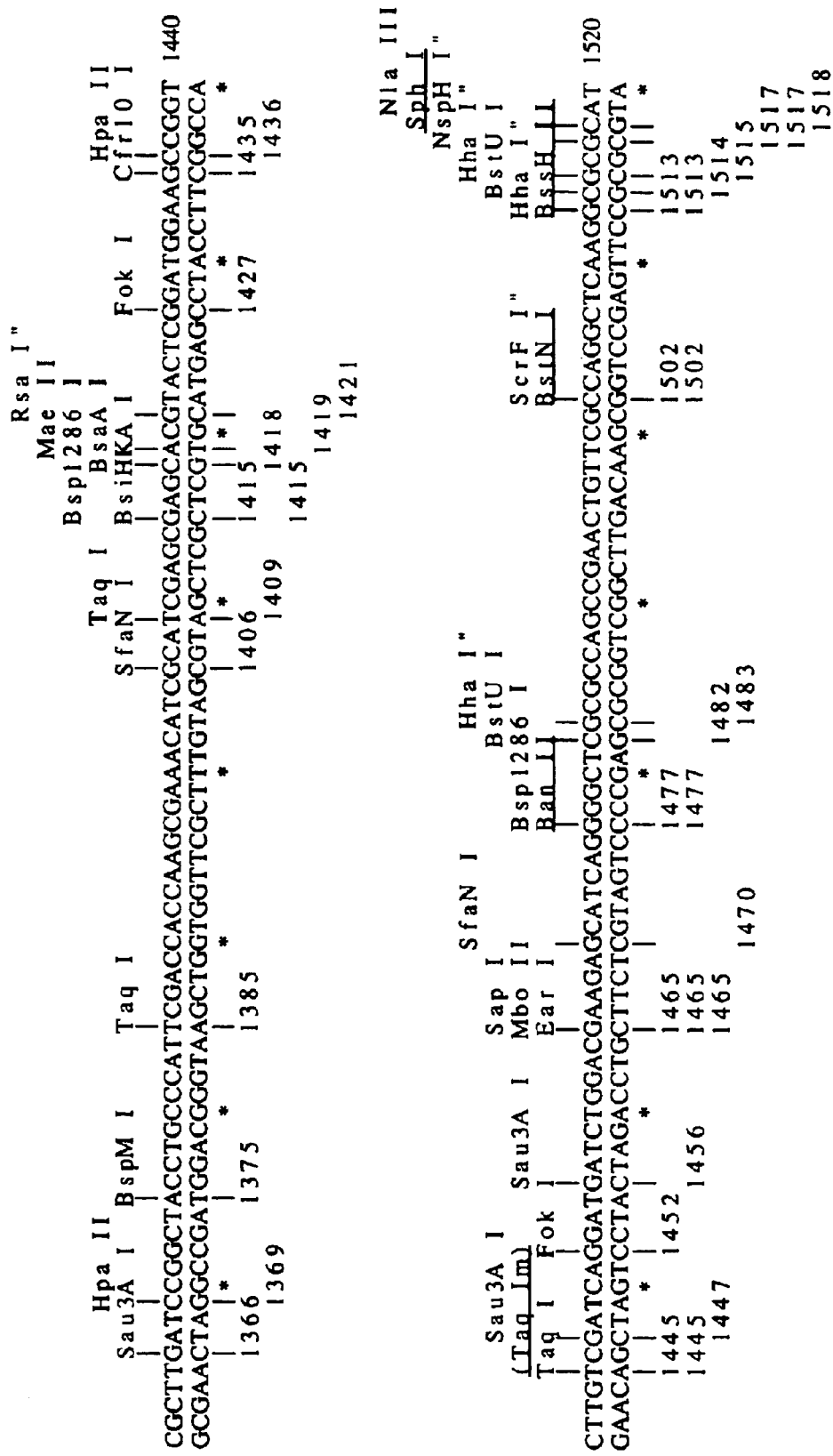
Fig. 2a₇

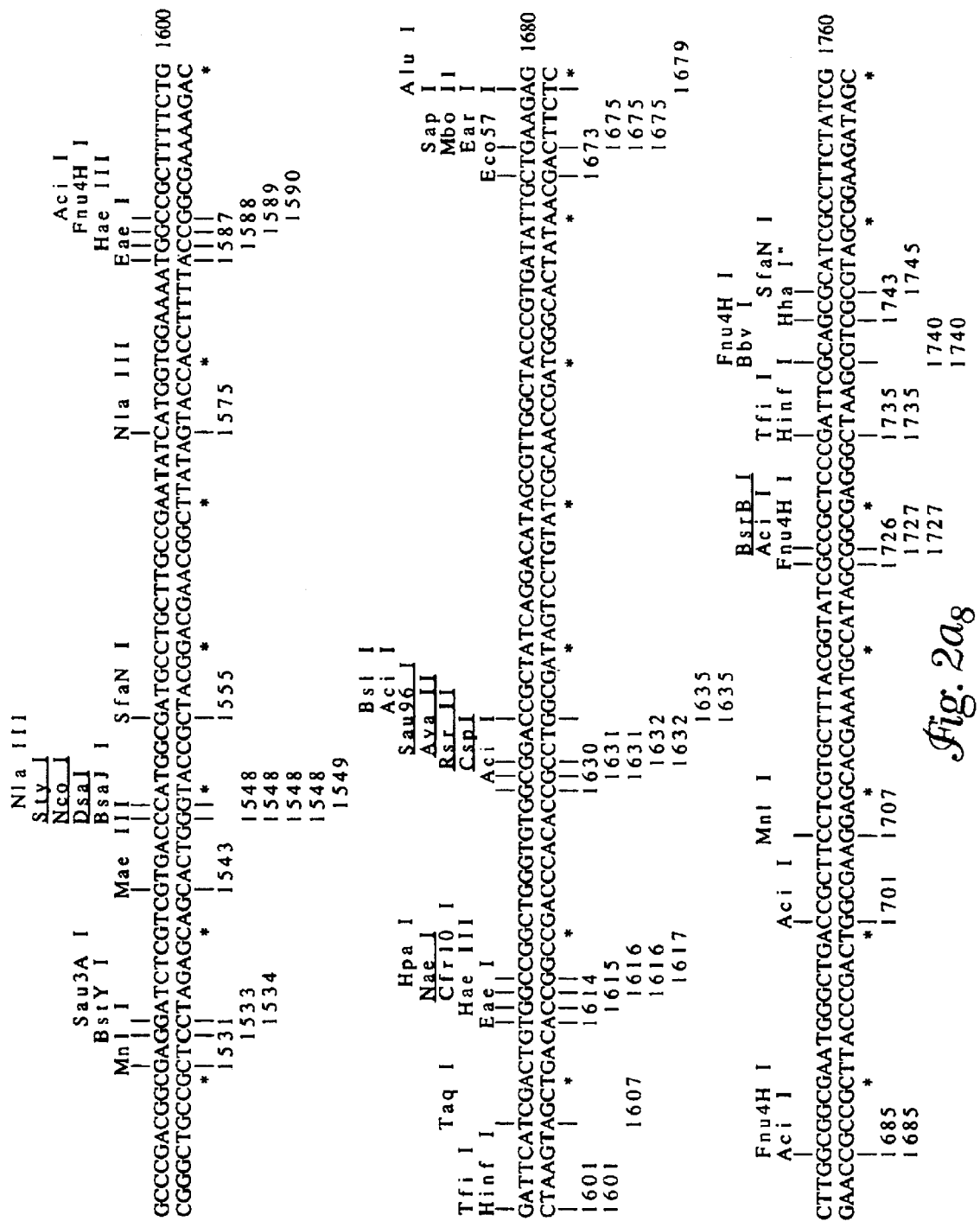
Fig. 2a₈

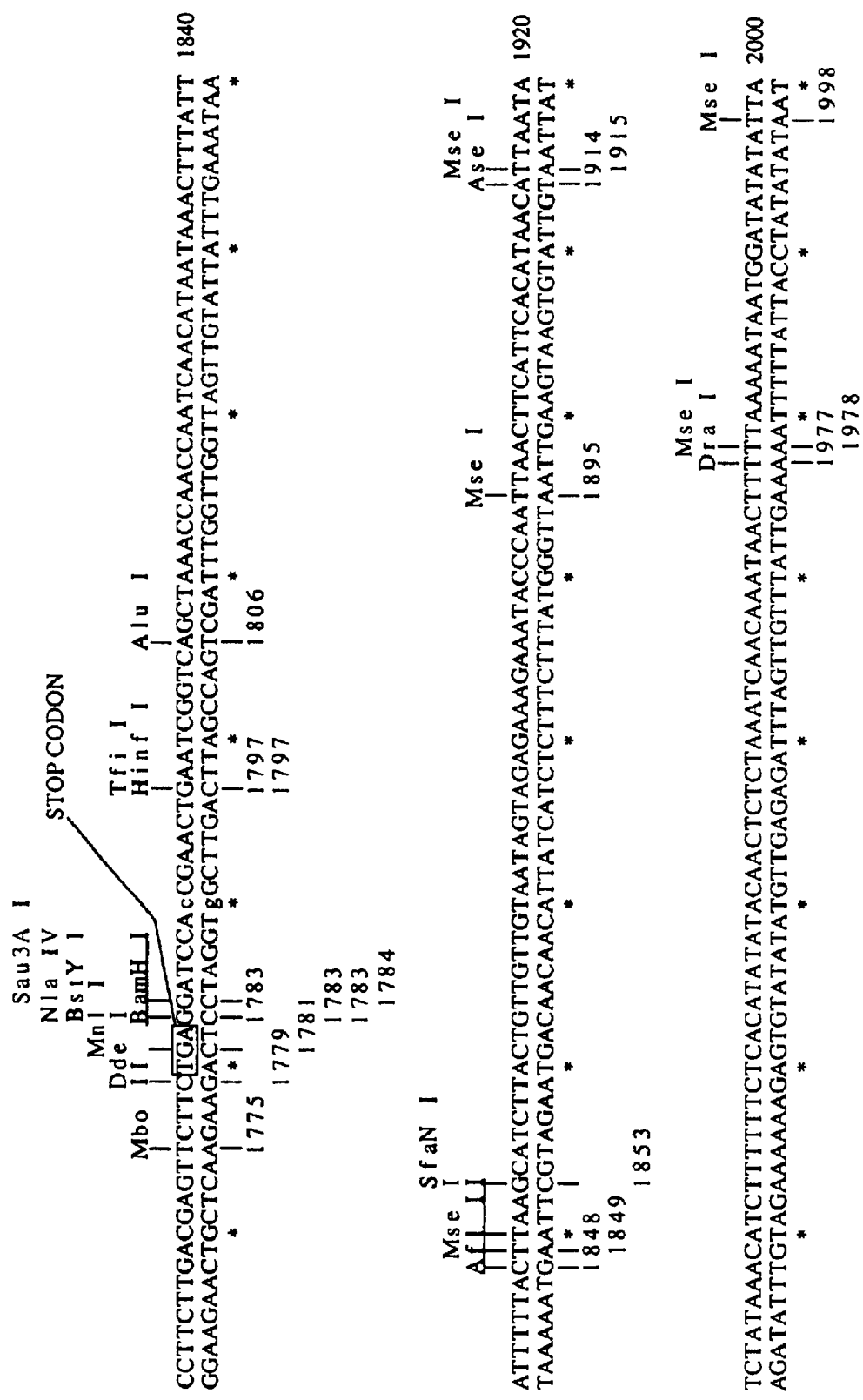
Fig. 2a₉

*Fig. 2b* pBICH3 --> Full Restriction Map

```
              Sau3A I                                                            Mse I                              SfaN I    Apo I
              BstY I                                                             |                                  |         |
SEQ ID NO:3 GGATCTCTCTCTATCGTATTTtGCAATAATAGGTATTAACTTTTATaCTGATTGTTAGTAGATgCCTTCAAATTTCTT
SEQ ID NO:4 CCTAGAGAGAGATAGCATAAAaCGTTATTATCCATAATTGAAAATAtGACTAACAATCATCTACGGAAGTTTAAAGAA
              ———                                                              ——                                  ——        ——  80
              | |                                                               |                                   |         |    *
              1 2                                                               38                                  63        72

Apo I          Mse I
                 Mse I          Dra I
                 Dra I          | |
                 Swa I          | |                                                                                  Mse I
                 | | |                                                                                 Sau3A I       |
TTTATTTAAATTCATATCTATATCTTTAAAACACtCcaCAtTTTTATTGTTGCTAACTGTGCtatGATCTTtAAGTCAAT
AAATAAATTTAAGTATAGATATAGAAATTTTGTGaGgtGTaAAATAACGATTGACACGatACTAGAAaTTCAGTTA
——————                                                                        ———                                   —— 160
||||                                                                           |                                     |    *
84 85 86 88                                                                   106 107                                146   151

Fnu4H I                                                                                    BsmA I     Apo I                                        SfaN I     PacI   Mse I
Bbv I                                                                                      |         |                                             FokI      Mse I   |
Alu I                                                                                      |         |                                             | |       |       |
AGCTGCTCATTTGTTGAACTCCACAGAGACACTaaaTTTGTTTATTTGATGgatGcTttaATtaaAgttgctaatctt
TCGACGAGTAAACAACTTGAGGTGTCTCTGTGAtttAAACAAATAAACTACctaCgAaattTAattTcaacgattagaa 240
———                                                                            ——         —— ——                                                   —— —       —       ——
| | |                                                                           |          |  |                                                    | |       |        |    *
161 162 162                                                                    187        195                                                   213 214    220     224
                                                                                                                                                            220
```

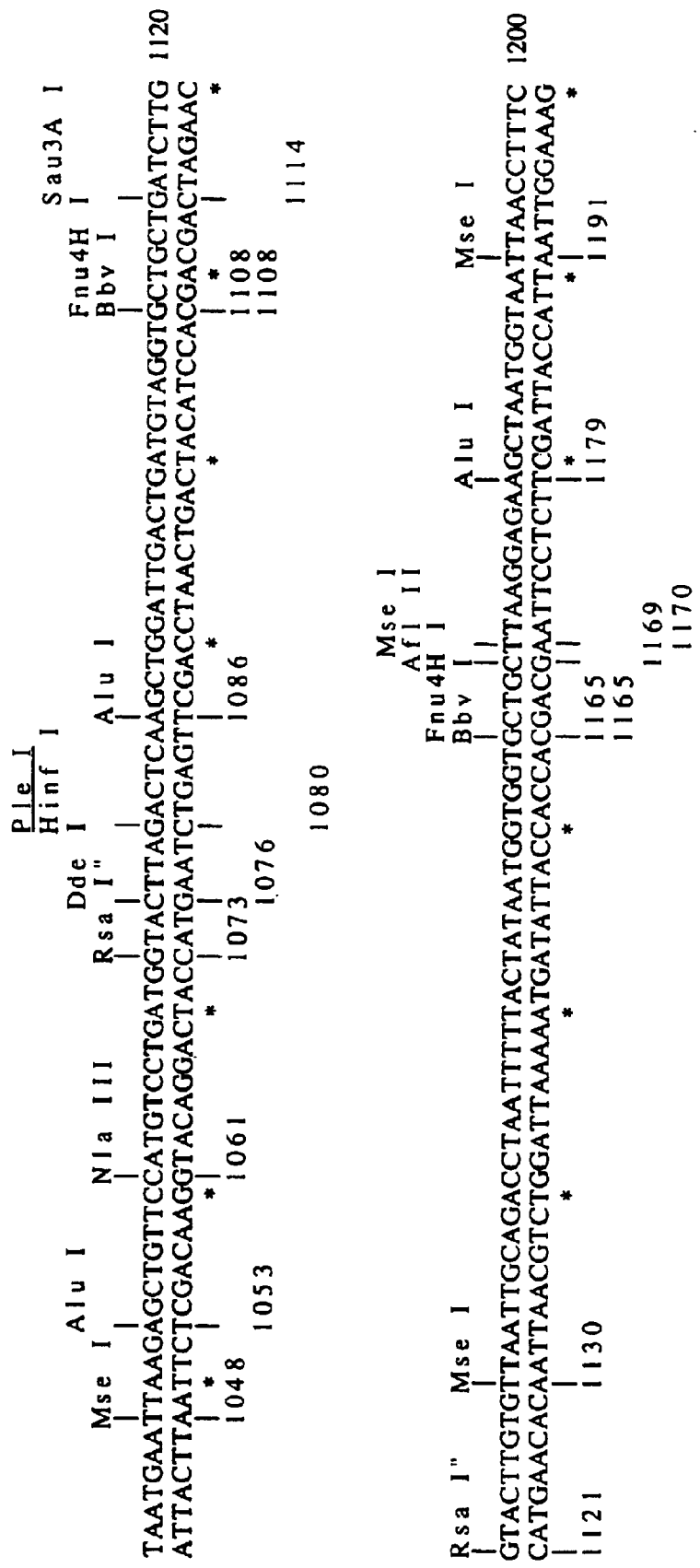
Fig. 2b₅

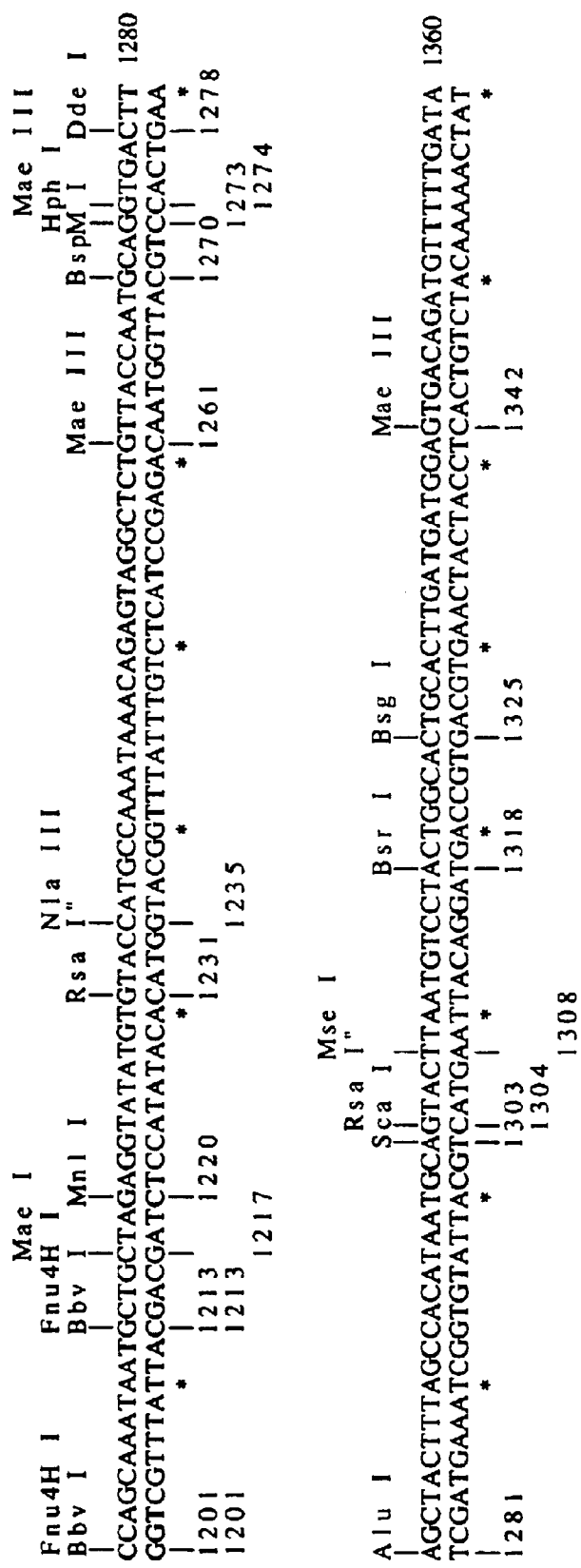
Fig. 2b₆

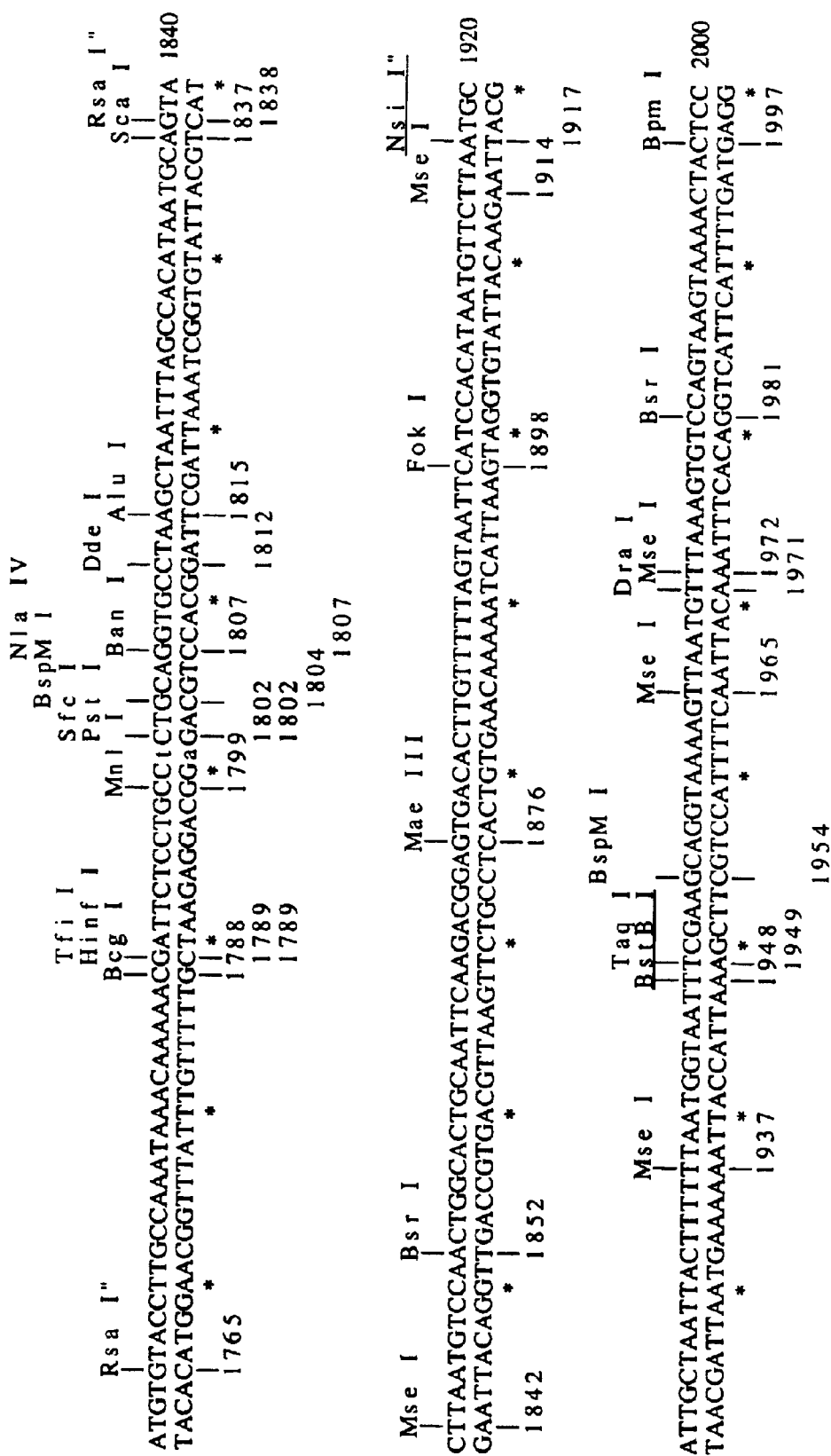
Fig. 2b₉

Fig. 2b₁₀

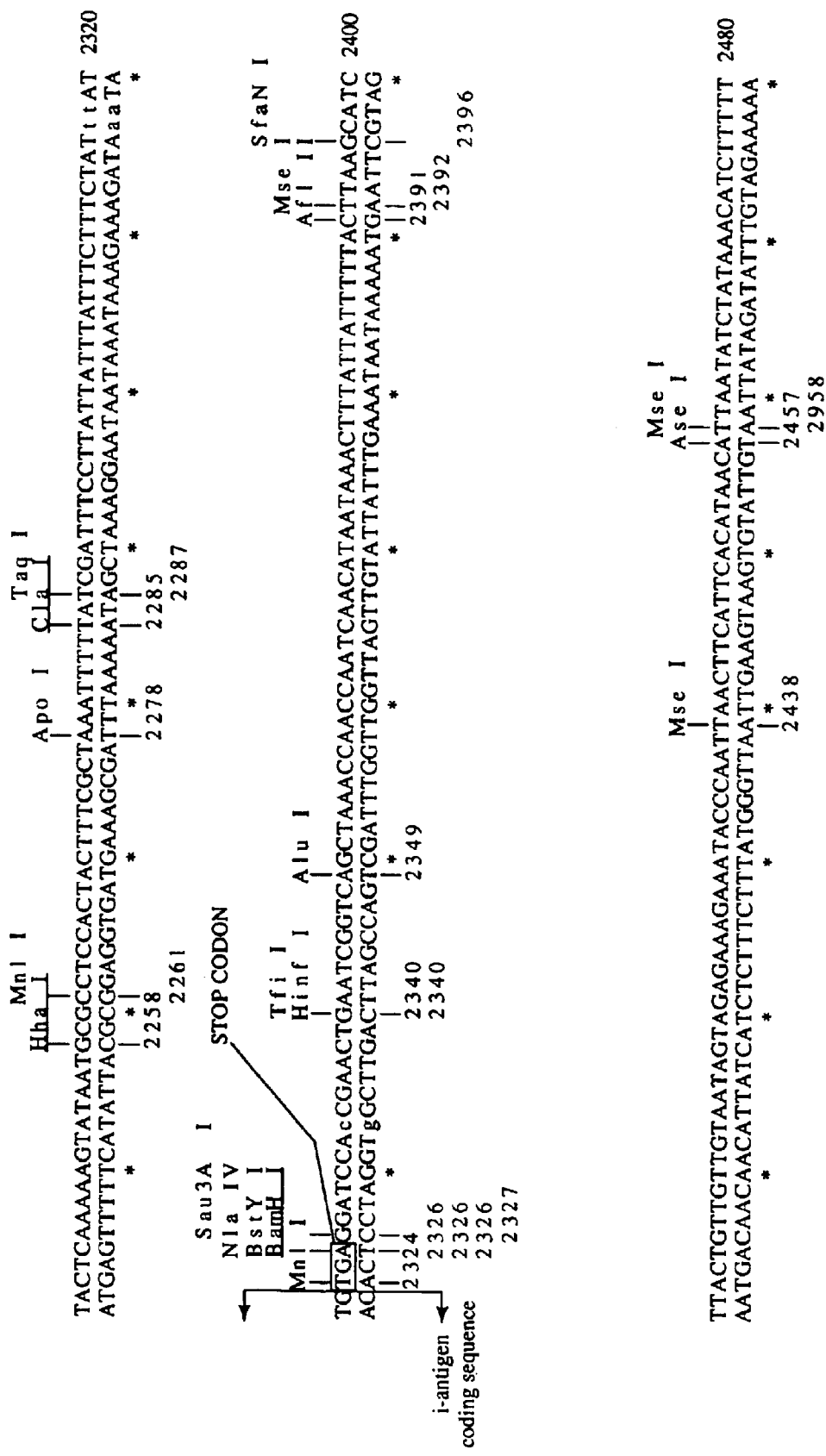
Fig. 2b₁₁

```
                                                                  Mse I
                           Mse I                                                                                     2560
                           Dra I                                                        *|
TCTCACATATATACAACTCTCTAAATCAACAACTTTTTAAAAATAATGGATATATATTAACAAAATAATATCTC
AGAGTGTATATGTTGAGAGATTTAGTTGTTGAAAAAATTTTATTACCTATATATAATTGTTTTATTATATAGAG
                                                                      2541
                                          Bsg I                                           Apo I
                                     Mae II                                                                          2640
                                     SnaB I              Hph I  Aci I                       *|
TTTTTACAAAATAGTTCTTATATAAATACGTATCTGCACTCACCCGCATTTTTCACAACAAAAACATACCAAAAAAATTC
AAAATGTTTTATCAAGAATATATTTATGCATAGACGTGAGTGGGCGTAAAAAGTGTTGTTTTTGTATGGTTTTTTAAG
                                     2587                2600  2604                         2635
                                     2587
                                     2588
                                             2594

Nla III"
    NspH I'                                                                                                          2720
    Afl III                                                                                                            *
TTACTTCTACATGTTTCCTTCTTATTATTCAAAATTATTTTATAAATAGCATAAAATAATAAATACAATAAAAAATAAACAA
AATGAAGATGTACAAAGGAAGAATAATAAGTTTTAATAAAATATTTATCGTATTTATTTATGTATTTTTTATTTGTT
    2649
    2649
    2650

Mse I       Ssp I                                                                         2800
                           Dra I                                                                                       *
AATCCTTTTTTTATTTTTGAATTATTTAAAACAAATATTTCAATCAATCAGTCAGTCAGTCAGCATAATATAAAGCAACAAAAC
TTAGGAAAAAAAATAAACTTAATAAAATTTGTTTATAAAGTTAGTTAGTCAGTCAGTCGTATTATATATTTCGTTGTTTTG
                           2744                    2753
                           2745

AAACCAAGTTG 2811
TTTGGTTCAAC
     *
```

*Fig. 2b*$_{12}$

```
SEQ ID NO: 5  G1    1   MKYNILILILISLPINELRAVPCPDGTQT-QAG-LTDVGAADLGTCVNCRPNFYYN-----
SEQ ID NO: 6  G5    1   MKNNILVILIISLPINQIKSANCPVGTETNTAGQVDDLGTP--ANCVNCQKNFYYNNAAA
                        *:: :. **.:.*** :       . *   .**    ..*****.:*****

G1   55   --GGAA------QGEANGNQP---------------------------------------
              G5   59   FVPGASTCTPCPQKKDGAGAQPNPPATANLVTQCNVKCPAGTAIAGGATDYAAIITECVNC
                          **:      *. .* *

G1   68   ---F-----AAN-NAARGICVPCQINRVGSVTNAGDLATLATQCSTQCPTGTALDDGVTDV
              G5  119   RINFYNENAPNFNAGASTCTACPVNRVGGALTAGNAATIVAQCNVACPTGTALDDGVTTD
                           *     ..* *.* .*.**:***.. *.. :*:.:** .********* *

G1  120   FDRSAAQCVKCKPNFYYNGGSSPQGEAPGVQVFAAGAAAAGVAAVTSQCVPCQLNK--NDS
              G5  179   YVRSFTECVKCRLNFYYNGNN--GNTP----FNPGK----------SQCTPCPAIKPANVA
                        : **  :****: ******.:    .*    *.               ** **.::   .

G1  178   PATAGAQANLATQCSNQCPTGTVLDDGVTLVFNTSATLCVKCRPNFYNGGSPQGEAPGV
              G5  224   QATLGNDATITAQCNVACPDGTISAAGVN-NWVAQNTECTNCAPNFYNNN-----AP--
                         ** .: **::**. .**.**: . **. * *.:.  :* ***** .     **

G1  238   QVPAAGAAAAGVAAVTSQCVPCQINKND-SPATAGAQANLATQCSTQCPTGTAIQDGVTL
              G5  275   -NFNPG--------NSTCLPCPANKDYGAEATAGGAATLAKQCNIACPDGTAIASGATN
                          :. *         .:*:  * ::  *:*:* .*.* ::**. .** *** .*.*

G1  297   VFSNSSTQCSQCIANYFFNG-NFEAGKSQCLKCPVSKTTPAHAP-GNTATQATQCLTTCP
              G5  325   -YVILQTECLNCAANFYFDGNNFPQAGSSRCKACPANKVQGAVATAGGTATLIAQCALECP
                         :. .:*.:* ** *:*::*.** :.:.*  :** . .      *.*** *:** :**

G1  355   VFSNSSTQCSQCIANFVASATECTKCSAGFFASKTTGFTAGTDTCTECTKKLTSGATAKVYAE
              G5  384   AGTVLTDGTNSTYKQAASECVKCAANPYTTKQTDWVAGIDTCTSCNKKLTSGAEANLPES
                        . **  **: .   ** ** **:*..      . :.*:*****:*.********  *  .

G1  415   ATQKVQCASTTAKFLSISLLPISFYLL
              G5  444   AKKNIQCD---FANFLSISLLLISYYLL
                        * ::: **    *::******* *:**
```

```
G1 SEQ ID NO: 7  ATGAAATATAATATTTTATTAATTTTAATTATTTCTTTATTTATTAATGAATTAAGAGCT
G5 SEQ ID NO: 8  ATGAAAAATAATATTTTAGTAATATTGATTATTTCATTATTTATCAATTAAATTAAATCT
                 *****  ********** ****  ** ********  ********  ***  **  *  *  **

G1               GTTCCATGTCCTGATGGTACTTAGACTCA---AGCTGGAT----TGACTGATGTAGGTGC
G5               GCTAATTGTCCTGTTGGAACTGAAACTAACACAGCCGGATAAGTTGA-TGATCTAGGAAC
                 *  *  *******  ***  ***  *  ***   *  ***  ****   ***  ****  ****  *

G1               TGCTGATCTTGGTACTTGTGTTAATTGC-AGACCTAATTTTTACTATAATGGTGGTGCTG
G5               TCCT------GCAAATTGTGTTAATTGTTAGAAA-AACTTTTATTATAATAATGCTGCTG
                 *  **       *  * *************  ***  **  ****** ******  **  *****

G1               CTTAAGGAGAAGCTAATGGTAATTAACCTTTCGCAGCAAATAATGCTGCTAGAGGTATAT
G5               CTT--------------------------TCGTTCC------TGGTGCTAG---TACGT
                 ***                          ***  *      **  *****   **  *

G1               GTGTACCATG-CCA-AATAAACAGA-GTAGGCTCTGTTACCAA-TGCAGGTG--ACTTAG
G5               GTACACCTTGTCCATAAAAAAAAGATGCTGGTGCT-TAACCAAATCCACCTGCTACT--G
                 **   ***  **  ***  **  ***  ***  *   *   **  *****  ***  **  ***   *

G1               CTACTTTAGCCACATAATGCAGTACTTAATGTCCTACTGGCACTGCACTTGATGATGGAG
G5               CTAATTTAGTCACATAATGTAACGTTAAATGCCCTGCTGGTACCGCAATTGCAGGTGGAG
                 ***  *****  ********* *   *  ****  ***  ****  **  ***  ***  *  *****

G1               TGACAGATGTTTTTG--ATAGATCAGCCGCATAATGTGTTAAATGCAAACCTAACTTTTA
G5               CAACAGATTATGCAGCAATA-ATCA----CAGAATGTGTTAATTGTAGAATTAATTTTTA
                 ******  *   *   ***  ****   **  ***********  **  *  *  ***  *****

G1               CTATAATGGTGGTTCTCCTTAAGGTGAAGCTCCTGGCGTTTAAGTTTTTGCTGCTGGTGC
G5               ---TAATGA-----------AA----ATGCTCC---------AAATTTTAA---------
                 *****      **  *  *****        *  ****

G1               TGCCGCTGCAGGTGTTGCTGCCGTTACTAGTTAATGTGTACCTTGCCAACTAAACAAAAA
G5               ------TGCAGGTG-----------CTAGTACATGCACAGCTTGTCCGGTAAACAGAGT
                  ********       *****  ***   *  ****  *    ******  *

G1               CGATTCTCCTGCCACTGCAGGT---GCCTAAGCTAATTTAGCCACATAATGTAGCAATTA
G5               TGGTGGTGCATTGACTGCTGGTAATGCC---GCTACCATAGTCGCATAATGTAACGTCGC
                 *  *  *  *    *****  ***   ***   ****  ***  *  *********  *
```

```
G1  ATGTCCTACTGGCACTGTACTTGATGATGGAGTGACACTTGTTTTTAATACATCAGCCAC
G5  ATGTCCTACTGGTACTGCACTTGATGATGGAGTAACTACTGATTATGTTAGATCATTCAC
    **********  ****  ***************  **  **  **  *  **  ****  ***

G1  ATTATGTGTTAAATGCAGACCTAACTTTTACTATAATGGT------GGTT---CTCCTTA
G5  AGAATGTGTTAAATGTAGACTTAACTTTTACTATAATGGTAATAATGGTAATACTCCTTT
    *  ************  ****  *********************          ***    ******

G1  ------AGGTGAA------------------------------GCTCCTGGCGTTTA
G5  CAATCCAGGTAAAAGTTAATGCACACCTTGTCCGGCAATTAAACCTGCTAATGTTGCTTA
          ****  **                                        ***  **  *  ***

G1  AG----TTT---------------------------------TTGC------TGCTGG
G5  AGCTACTTTAGGTAATGATGCTACAATAACCGCATAATGTAACGTTGCATGCCCTGATGG
    **    ***                                      ****      **  ***

G1  TGCT------GCCGCTGCAG---------GTGTTGC-----------------------
G5  TACTATAAGTGCTGCTGGAGTAAATAATTGGGTAGCACAAAACACTGAATGTACTAATTG
    *  **      **  ****  **        **  **  **

G1  ------------------------------------------TGCCGTTACTAGTTAATGTGT
G5  TGCTCCTAACTTTTACAATAATAATGCTCCTAATTTCAATCCAGGTAATAGTACATGCCT
                                              *  *  *  **  ****  ***  *

G1  ACCTTGCCAAATAAACAAAAACGATTCTCCTG---CCACTGCAGGTGCCTAAGCTAATTT
G5  ACCTTGCCCAGCAAATAAAGATTATGGTGCTGAAGCCACTGCAGGTGGTGCCGCTACTTT
    ********  *  ***  ***  *  **  *  ***  *********  ****  ***

G1  AGCCACATAATGCAGTACTTAATGTCCAACTGGCACTGCAATT-CAAGACGGAGTGACAC
G5  AGCCAAATAATGTAATATTGCATGCCCTGATGGTACTGCAATTGCTAGT-GGAGCAAC--
    *****  ******  **  *  ***  **  **  ***  **********  *  **  ****  **

G1  TTGTTTTTAGTAAT-TCATCCACATAATGTTCTTAAT-GCATTGCTAATTACTTTTTTAA
G5  -TAATTAT-GTAATATTATAAACAGAATGT-CTAAATTGTGCTGCTAACTTTTATTTTGA
     *  **  *  *****  *  **  ***  *****  **  ***  *  ******  *  *  ****  *

G1  TGGTAAT---TTCGAAGCAGGTAAAAGTTAATGTTTAAAG--TGTCCAGTAAGTAAAACT
G5  TGGTAATAATTTCTAGGCAGGAAGTAGTAGATGC--AAAGCATGTCCAGCAAATAAAGTT
    *******  ***  *  *****  *  ***  ***  ****  *******  **  ****  *

G1  A------CTCCAGCACATGCTCCAGGTAATACTGCTACTTAAGCCACATAATGT----TT
G5  TAAGGCGCTGTAGCAA---CTGCAGGTGGTACTGCTACTTTAATTGCATAATGTGCCCTT
    **  ****    **  *****  *************  *  ********  **

G1  GACCACATGTCCTGCTGGTACAGTACTTGATGATGGAACATCAACTAATTTTGTAGCTTC
G5  GA----ATGCCCTGCTGGTACTGTACTCACCGATGGAACAACATCTACTTATAAATAAGC
    **      ***  ************  *****  ********  **  ***  **  *  *  *

G1  CGCAACTGAATGTACTAAATGTTCTGCTGGCTTTTTTGCATCAAAAACAACTGGTTTTAC
G5  AGCATCTGAATGTGTTAAATGTGCTGCCAACTTTTATACTACAAAATAAACTGATTGGGT
    ***  ********  ******  ****    *****  *  **  *****  *****  **

G1  AGCAGGTACTGATACATGTACTGAATGTACTAAAAAATTAACTTCTGGTGCCACAGCTAA
G5  AGCAGGTATTGATACATGTACTAGTTGTAATAAAAAATTAACTTCTGGCGCTGAAGCTAA
    ********  ************  ****  ******************  **    ******

G1  AGTATATGCTGAAGCTACTCAAAAAG---TATAATGCGCCTCCACTACTTTCGCTAAATT
G5  TTTAC---CTGAATCTGCTAAAAAAAAATATATAATGTG---------ATTTCGCTAATTT
    **    *****  **  **  *****    ******  *          *********  **

G1  TTTATCGATTTCCTTATTATTTATTTCTTTCTATTTATTG
G5  TTTATCAATTTCCTTATTATTGATTTCTTATTATTTATTA
    ******  *************  ******  *******
```

*Fig. 3b₂* total protein from cell pellet

-gpi/G1 (50/69)　　　G1　neo medium without cells

-gpi/G1 (50/69)　　　G1　neo

Serum: anti-live TG1 (1 : 20)

Serum: anti-live Tneo (1 : 20) (negative control)

SEQUENCE LISTING

<160> NUMBER OF SEQ ID NOS: 14

<210> SEQ ID NO 1
<211> LENGTH: 2268
<212> TYPE: DNA
<213> ORGANISM: Artificial Sequence
<220> FEATURE:
<223> OTHER INFORMATION: Description of Artificial Sequence: BTU::neo1
      construct

<400> SEQUENCE: 1

```
ggatctctct ctctatcgta ttttgcaata ataggtatta acttttatac tgattgttag    60
tagatgcctt caaatttctt tttatttaaa ttcatatcta tatcttttaa aacactccac   120
attttattgt tgctaactgt gctatgatct ttaagtcaat agctgctcat tttgttgaac   180
tccacagaga cactaaattt gtttattttg atggatgctt taattaaagt tgctaatctt   240
gcttgacatt tagccaacta ttggaagatc aaaatgtagc ttaaatctca aaaaatcatc   300
ataatttact atcaaattat taagaaattc atataacacc actttattga cttttattc    360
atcttataga gtgatagtag agttgagcca aattgatact tgtttacgtt gtattatttt   420
acgttgtatt attttgaaat tttaaaaaaa tgaaaatgag agaaaaattt atttaaattt   480
gagcttagaa tctttaagga agatcaaaaa tgggctaact aaatgttaga gtacgaagac   540
tgttcttgaa ataaagtgtc atcctttacg aatcaagttg ctactttaat gaataataga   600
atttgaggta gagctaaaat gagagatata gtaatgctat tggattatat ttggtttgta   660
ttgatggttt ttcttttggta aatgaatgat ataaatgaag agtggcaata aaattaattg   720
aaattgaatg aaaaaatgaa tagaaattaa agaagagtat aattttattt tttgaaattt   780
ttaattttaa aatttttaat gcgtgtattt tatttgggtg atgaaaaggg taaataaagg   840
gcgttgcact tttctcaata gtaatattta agaagagagg gatttagaag gaaaaatcat   900
aatcaaataa aaaaaataaa aaagtttgaa aaaaaacctt caaaaaaaat aaataaaaac   960
aaaatcactc ctttaagcaa ttaaaaaatg gcaagcttgg atggattgca cgcaggttct  1020
ccggccgctt gggtggagag gctattcggc tatgactggg cacaacagac aatcggctgc  1080
tctgatgccg ccgtgttccg gctgtcagcg caggggcgcc cggttctttt tgtcaagacc  1140
gacctgtccg gtgccctgaa tgaactgcag gacgaggcag cgcggctatc gtggctggcc  1200
acgacgggcg ttccttgcgc agctgtgctc gacgttgtca ctgaagcggg aagggactgg  1260
ctgctattgg gcgaagtgcc ggggcaggat ctcctgtcat ctcaccttgc tcctgccgag  1320
aaagtatcca tcatggctga tgcaatgcgg cggctgcata cgcttgatcc ggctacctgc  1380
ccattcgacc accaagcgaa acatcgcatc gagcgagcac gtactcggat ggaagccggt  1440
cttgtcgatc aggatgatct ggacgaagag catcaggggc tcgcgccagc cgaactgttc  1500
gccaggctca aggcgcgcat gcccgacggc gaggatctcg tcgtgaccca tggcgatgcc  1560
tgcttgccga atatcatggt ggaaaatggc cgcttttctg gattcatcga ctgtggccgg  1620
ctgggtgtgg cggaccgcta tcaggacata gcgttggcta cccgtgatat tgctgaagag  1680
cttggcggcg aatgggctga ccgcttcctc gtgctttacg gtatcgccgc tcccgattcg  1740
cagcgcatcg ccttctatcg ccttcttgac gagttcttct gaggatccac cgaactgaat  1800
cggtcagcta aaccaaccaa tcaacataat aaactttatt atttttactt aagcatctta  1860
ctgttgttgt aatagtagag aaagaaatac ccaattaact tcattcacat aacattaata  1920
```

```
tctataaaca tcttttttct cacatatata caactctcta aatcaacaaa taactttta         1980 aaaataatgg atatatatta acaaaataat atatctcttt ttacaaaata gttcttatat         2040
aaatacgtat ctgcactcac ccgcattttt cacaacaaaa acataccaaa aaaattctta         2100
cttctacatg tttccttctt attattcaaa attattttat aaatagcata aaataaatac         2160
aataaaaaaa taaacaaaat ccttttttta ttttgaatta tttaaaacaa atattttcaa         2220
tcaatcagtc agtcagcata atataaagca acaaaacaaa ccaagttg                     2268

<210> SEQ ID NO 2
<211> LENGTH: 2268
<212> TYPE: DNA
<213> ORGANISM: Artificial Sequence
<220> FEATURE:
<223> OTHER INFORMATION: Description of Artificial Sequence:
      Complement of BTU::neo 1 construct

<400> SEQUENCE: 2
caacttggtt tgttttgttg ctttatatta tgctgactga ctgattgatt gaaaatattt           60
gttttaaata attcaaaata aaaaaaggat tttgtttatt tttttattgt atttattta          120 tgctatttat aaaataattt tgaataataa gaaggaaaca tgtagaagta agaatttttt         180
tggtatgttt ttgttgtgaa aaatgcgggt gagtgcagat acgtatttat ataagaacta         240
ttttgtaaaa agagatatat tattttgtta atatatatcc attattttta aaaagttatt         300
tgttgattta gagagttgta tatatgtgag aaaaaagatg tttatagata ttaatgttat         360
gtgaatgaag ttaattgggt atttctttct ctactattac aacaacagta agatgcttaa         420
gtaaaaataa taaagtttat tatgttgatt ggttggttta gctgaccgat tcagttcggt         480
ggatcctcag aagaactcgt caagaaggcg atagaaggcg atgcgctgcg aatcgggagc         540
ggcgataccg taaagcacga ggaagcggtc agcccattcg ccgccaagct cttcagcaat         600
atcacgggta gccaacgcta tgtcctgata gcggtccgcc acacccagcc ggccacagtc         660
gatgaatcca gaaaagcggc cattttccac catgatattc ggcaagcagg catcgccatg         720
ggtcacgacg agatcctcgc cgtcgggcat gcgcgccttg agcctggcga acagttcggc         780
tggcgcgagc ccctgatgct cttcgtccag atcatcctga tcgacaagac cggcttccat         840
ccgagtacgt gctcgctcga tgcgatgttt cgcttggtgg tcgaatgggc aggtagccgg         900
atcaagcgta tgcagccgcc gcattgcatc agccatgatg gatactttct cggcaggagc         960
aaggtgagat gacaggagat cctgccccgg cacttcgccc aatagcagcc agtcccttcc        1020
cgcttcagtg acaacgtcga gcacagctgc gcaaggaacg cccgtcgtgg ccagccacga        1080
tagccgcgct gcctcgtcct gcagttcatt cagggcaccg gacaggtcgg tcttgacaaa        1140
aagaaccggg cgcccctgcg ctgacagccg gaacacggcg gcatcagagc agccgattgt        1200
ctgttgtgcc cagtcatagc cgaatagcct ctccacccaa gcggccggag aacctgcgtg        1260
caatccatcc aagcttgcca ttttttaatt gcttaaagga gtgattttgt ttttatttat        1320 ttttttttgaa ggtttttttt caacttttt tatttttttt atttgattat gattttttcct       1380 tctaaatccc tctcttctta aatattacta ttgagaaaag tgcaacgccc tttatttacc        1440
cttttcatca cccaaataaa atacacgcat taaaaattttt aaaattaaaa atttcaaaaa       1500
ataaaattat actcttcttt aatttctatt cattttttca ttcaatttca attaattta         1560 ttgccactct tcatttatat cattcattta ccaaagaaaa accatcaata caaaccaaat        1620
ataatccaat agcattacta tatctctcat tttagctcta cctcaaattc tattattcat        1680
```

-continued

```
taaagtagca acttgattcg taaaggatga cactttattt caagaacagt cttcgtactc    1740
taacatttag ttagcccatt tttgatcttc cttaaagatt ctaagctcaa atttaaataa    1800 attttctct catttcatt tttaaaat ttcaaaataa tacaacgtaa aataatacaa         1860
cgtaaacaag tatcaatttg gctcaactct actatcactc tataagatga ataaaaagtc    1920
aataaagtgg tgtttatga atttcttaat aatttgatag taaattatga tgatttttg      1980 agatttaagc tacattttga tcttccaata gttggctaaa tgtcaagcaa gattagcaac    2040
tttaattaaa gcatccatca aaataaacaa atttagtgtc tctgtggagt tcaacaaaat    2100
gagcagctat tgacttaaag atcatagcac agttagcaac aataaaatgt ggagtgtttt    2160
aaaagatata gatatgaatt taaataaaaa gaaatttgaa ggcatctact aacaatcagt    2220
ataaaagtta atacctatta ttgcaaaata cgatagagag agagatcc                 2268
```

<210> SEQ ID NO 3
<211> LENGTH: 2811
<212> TYPE: DNA
<213> ORGANISM: Artificial Sequence
<220> FEATURE:
<223> OTHER INFORMATION: Description of Artificial Sequence: pBICH3 construct

<400> SEQUENCE: 3

```
ggatctctct ctctatcgta ttttgcaata ataggtatta acttttatac tgattgttag      60
tagatgcctt caaatttctt tttatttaaa ttcatatcta tatcttttaa aacactccac     120
attttattgt tgctaactgt gctatgatct ttaagtcaat agctgctcat tttgttgaac     180
tccacagaga cactaaattt gtttattttg atggatgctt taattaaagt tgctaatctt     240
gcttgacatt tagccaacta ttggaagatc aaaatgtagc ttaaatctca aaaaatcatc     300
ataatttact atcaaattat taagaaattc ataacacc actttattga cttttattc        360 atcttataga gtgatagtag agttgagcca aattgatact tgtttacgtt gtattatttt     420
acgttgtatt atttttgaaat tttaaaaaaa tgaaaatgag agaaaatttt atttaaattt    480
gagcttagaa tctttaagga agatcaaaaa tgggctaact aaatgttaga gtacgaagac     540
tgttcttgaa ataaagtgtc atcctttacg aatcaagttg ctactttaat gaataataga    600
atttgaggta gagctaaaat gagagatata gtaatgctat tggattatat ttggtttgta     660
ttgatggttt ttctttggta aatgaatgat ataaatgaag agtggcaata aaattaattg    720
aaattgaatg aaaaaatgaa tagaaattaa agaaagagt aatttttattt tttgaaattt     780 ttaattttaa aatttttaat gcgtgtattt tatttgggtg atgaaaaggg taaataaagg     840
gcgttgcact tttctcaata gtaatatta agaagagagg gattttagaag gaaaaatcat     900 aatcaaataa aaaaaataaa aaagtttgaa aaaaaaccctt caaaaaaaaa t aaataaaaac  960 aaaatcactc ctttaagcaa ttaaaaaatg gcaagcttga aatataatat tttattaatt    1020
ttaattattt ctttatttat taatgaatta agagctgttc catgtcctga tggtacttag    1080
actcaagctg gattgactga tgtaggtgct gctgatcttg gtacttgtgt taattgcaga    1140 cctaatttt actataatgg tggtgctgct taaggagaag ctaatggtaa ttaaccttc      1200 gcagcaaata atgctgctag aggtatatgt gtaccatgcc aaataaacag agtaggctct    1260
gttaccaatg caggtgactt agctacttta gccacataat gcagtactta atgtcctact    1320
ggcactgcac ttgatgatgg agtgacagat gttttgata gatcagccgc ataatgtgtt    1380
aaatgcaaac ctaacttta ctataatggt ggttctcctt aaggtgaagc tcctggcgtt     1440
```

-continued

```
taagtttttg ctgctggtgc tgccgctgca ggtgttgctg ccgttactag ttaatgtgta      1500
ccttgccaac taaacaaaaa cgattctcct gccactgcag gtgcctaagc taatttagcc      1560
acataatgta gcaattaatg tcctactggc actgtacttg atgatggagt gacacttgtt      1620
tttaatacat cagccacatt atgtgttaaa tgcagaccta acttttacta taatggtggt      1680
tctccttaag gtgaagctcc tggcgtttaa gttttgctg ctggtgctgc cgctgcaggt      1740
gttgctgccg ttactagtta atgtgtacct tgccaaataa acaaaaacga ttctcctgcc      1800
tctgcaggtg cctaagctaa tttagccaca taatgcagta cttaatgtcc aactggcact      1860
gcaattcaag acggagtgac acttgttttt agtaattcat ccacataatg ttcttaatgc      1920
attgctaatt acttttttaa tggtaatttc gaagcaggta aaagttaatg tttaaagtgt      1980
ccagtaagta aaactactcc agcacatgct ccaggtaata ctgctactta agccacataa      2040
tgtttgacca catgtcctgc tggtacagta cttgatgatg aacatcaac taattttgta       2100 gcttccgcaa ctgaatgtac taaatgttct gctggctttt ttgcatcaaa acaactggt       2160 tttacagcag gtactgatac atgtactgaa tgtactaaaa aattaacttc tggtgccaca      2220
gctaaagtat atgctgaagc tactcaaaaa gtataatgcg cctccactac tttcgctaaa      2280 ttttatcga tttccttatt atttattct ttctatttat tgtgaggatc caccgaactg         2340
aatcggtcag ctaaaccaac caatcaacat aataaacttt attatttta cttaagcatc       2400 ttactgttgt tgtaatagta gagaaagaaa tacccaatta acttcattca cataacatta     2460
atatctataa acatcttttt tctcacatat atacaactct ctaaatcaac aaataacttt     2520
ttaaaaataa tggatatata ttaacaaaat aatatatctc tttttacaaa atagttctta    2580
tataaatacg tatctgcact cacccgcatt tttcacaaca aaaacatacc aaaaaaattc     2640
ttacttctac atgtttcctt cttattattc aaaattattt tataaatagc ataaaataaa   2700
tacaataaaa aaataaacaa aatccttttt ttattttgaa ttatttaaaa caaatatttt    2760
caatcaatca gtcagtcagc ataatataaa gcaacaaaac aaaccaagtt g              2811
```

<210> SEQ ID NO 4
<211> LENGTH: 2811
<212> TYPE: DNA
<213> ORGANISM: Artificial Sequence
<220> FEATURE:
<223> OTHER INFORMATION: Description of Artificial Sequence:
      Complement of pBICH 3 vector construct

<400> SEQUENCE: 4

```
caacttggtt tgttttgttg ctttatatta tgctgactga ctgattgatt gaaatatttt       60
gttttaaata attcaaaata aaaaaaggat tttgtttatt ttttattgt atttatttta       120 tgctatttat aaaataattt tgaataataa gaaggaaaca tgtagaagta agaatttttt      180
tggtatgttt ttgttgtgaa aaatgcgggt gagtgcagat acgtatttat ataagaacta     240
ttttgtaaaa agagatatat tattttgtta atatatatcc attattttta aaaagttatt    300
tgttgattta gagagttgta tatatgtgag aaaaaagatg tttatagata ttaatgttat    360
gtgaatgaag ttaattgggt atttctttct ctactattac aacaacagta agatgcttaa    420
gtaaaaataa taagtttat tatgttgatt ggttggttta gctgaccgat tcagttcggt     480
ggatcctcac aataaataga aagaaataaa taataaggaa atcgataaaa atttagcgaa    540
agtagtggag gcgcattata cttttttgagt agcttcagca tatactttag ctgtggcacc   600
agaagttaat ttttttagtac attcagtaca tgtatcagta cctgctgtaa aaccagttgt   660
```

-continued

| | |
|---|---|
| ttttgatgca aaaaagccag cagaacattt agtacattca gttgcggaag ctacaaaatt | 720 |
| agttgatgtt ccatcatcaa gtactgtacc agcaggacat gtggtcaaac attatgtggc | 780 |
| ttaagtagca gtattacctg gagcatgtgc tggagtagtt ttacttactg gacactttaa | 840 |
| acattaactt ttacctgctt cgaaattacc attaaaaaag taattagcaa tgcattaaga | 900 |
| acattatgtg gatgaattac taaaaacaag tgtcactccg tcttgaattg cagtgccagt | 960 |
| tggacattaa gtactgcatt atgtggctaa attagcttag gcacctgcag aggcaggaga | 1020 |
| atcgtttttg tttatttggc aaggtacaca ttaactagta acggcagcaa cacctgcagc | 1080 |
| ggcagcacca gcagcaaaaa cttaaacgcc aggagcttca ccttaaggag aaccaccatt | 1140 |
| atagtaaaag ttaggtctgc atttaacaca taatgtggct gatgtattaa aaacaagtgt | 1200 |
| cactccatca tcaagtacag tgccagtagg acattaattg ctacattatg tggctaaatt | 1260 |
| agcttaggca cctgcagtgg caggagaatc gttttgttt agttggcaag gtacacatta | 1320 |
| actagtaacg gcagcaacac ctgcagcggc agcaccagca gcaaaaactt aaacgccagg | 1380 |
| agcttcacct taaggagaac caccattata gtaaagtta ggtttgcatt taacacatta | 1440 |
| tgcggctgat ctatcaaaaa catctgtcac tccatcatca agtgcagtgc cagtaggaca | 1500 |
| ttaagtactg cattatgtgg ctaaagtagc taagtcacct gcattggtaa cagagcctac | 1560 |
| tctgtttatt tggcatggta cacatatacc tctagcagca ttatttgctg cgaaaggtta | 1620 |
| attaccatta gcttctcctt aagcagcacc accattatag taaaaattag gtctgcaatt | 1680 |
| aacacaagta ccaagatcag cagcacctac atcagtcaat ccagcttgag tctaagtacc | 1740 |
| atcaggacat ggaacagctc ttaattcatt aataaataaa gaaataatta aaattaataa | 1800 |
| aatattatat ttcaagcttg ccatttttta attgcttaaa ggagtgattt tgttttatt | 1860 |
| tatttttttt gaaggttttt tttcaaactt ttttatttt tttatttgat tatgattttt | 1920 |
| ccttctaaat ccctctcttc ttaaatatta ctattgagaa aagtgcaacg ccctttattt | 1980 |
| acccttttca tcacccaaat aaaatacacg cattaaaaat tttaaaatta aaaatttcaa | 2040 |
| aaaataaaat tatactcttc tttaatttct attcattttt tcattcaatt tcaattaatt | 2100 |
| ttattgccac tcttcattta tatcattcat ttaccaaaga aaaccatca atacaaacca | 2160 |
| aatataatcc aatagcatta ctatatctct cattttagct ctacctcaaa ttctattatt | 2220 |
| cattaaagta gcaacttgat tcgtaaagga tgacactta tttcaagaac agtcttcgta | 2280 |
| ctctaacatt tagttagccc atttttgatc ttccttaaag attctaagct caaatttaaa | 2340 |
| taaattttc tctcattttc attttttaa aatttcaaaa taatacaacg taaaataata | 2400 |
| caacgtaaac aagtatcaat ttggctcaac tctactatca ctctataaga tgaataaaaa | 2460 |
| gtcaataaag tggtgttata tgaatttctt aataatttga tagtaaatta tgatgatttt | 2520 |
| ttgagattta agctacattt tgatcttcca atagttggct aaatgtcaag caagattagc | 2580 |
| aactttaatt aaagcatcca tcaaaataaa caaatttagt gtctctgtgg agttcaacaa | 2640 |
| aatgagcagc tattgactta agatcatag cacagttagc aacaataaaa tgtggagtgt | 2700 |
| tttaaaagat atagatatga atttaataa aagaaatttt gaaggcatct actaacaatc | 2760 |
| agtataaaag ttaatacccta ttattgcaaa atacgataga gagagagatc | 2811 |

<210> SEQ ID NO 5
<211> LENGTH: 442
<212> TYPE: PRT
<213> ORGANISM: Ichthyophthirius multifiliis

<400> SEQUENCE: 5

```
Met Lys Tyr Asn Ile Leu Leu Ile Leu Ile Ser Leu Phe Ile Asn
 1               5                  10                  15

Glu Leu Arg Ala Val Pro Cys Pro Asp Gly Thr Gln Thr Gln Ala Gly
            20                  25                  30

Leu Thr Asp Val Gly Ala Ala Asp Leu Gly Thr Cys Val Asn Cys Arg
        35                  40                  45

Pro Asn Phe Tyr Tyr Asn Gly Gly Ala Gln Gly Glu Ala Asn Gly
     50                  55                  60

Asn Gln Pro Phe Ala Ala Asn Asn Ala Ala Arg Gly Ile Cys Val Pro
 65                  70                  75                  80

Cys Gln Ile Asn Arg Val Gly Ser Val Thr Asn Ala Gly Asp Leu Ala
                85                  90                  95

Thr Leu Ala Thr Gln Cys Ser Thr Gln Cys Pro Thr Gly Thr Ala Leu
                100                 105                 110

Asp Asp Gly Val Thr Asp Val Phe Asp Arg Ser Ala Ala Gln Cys Val
            115                 120                 125

Lys Cys Lys Pro Asn Phe Tyr Tyr Asn Gly Gly Ser Pro Gln Gly Glu
130                 135                 140

Ala Pro Gly Val Gln Val Phe Ala Ala Gly Ala Ala Ala Gly Val
145                 150                 155                 160

Ala Ala Val Thr Ser Gln Cys Val Pro Cys Gln Leu Asn Lys Asn Asp
                165                 170                 175

Ser Pro Ala Thr Ala Gly Ala Gln Ala Asn Leu Ala Thr Gln Cys Ser
                180                 185                 190

Asn Gln Cys Pro Thr Gly Thr Val Leu Asp Asp Gly Val Thr Leu Val
                195                 200                 205

Phe Asn Thr Ser Ala Thr Leu Cys Val Lys Cys Arg Pro Asn Phe Tyr
                210                 215                 220

Tyr Asn Gly Gly Ser Pro Gln Gly Glu Ala Pro Gly Val Gln Val Phe
225                 230                 235                 240

Ala Ala Gly Ala Ala Ala Gly Val Ala Ala Val Thr Ser Gln Cys
                245                 250                 255

Val Pro Cys Gln Ile Asn Lys Asn Asp Ser Pro Ala Thr Ala Gly Ala
                260                 265                 270

Gln Ala Asn Leu Ala Thr Gln Cys Ser Thr Gln Cys Pro Thr Gly Thr
                275                 280                 285

Ala Ile Gln Asp Gly Val Thr Leu Val Phe Ser Asn Ser Ser Thr Gln
                290                 295                 300

Cys Ser Gln Cys Ile Ala Asn Tyr Phe Phe Asn Gly Asn Phe Glu Ala
305                 310                 315                 320

Gly Lys Ser Gln Cys Leu Lys Cys Pro Val Ser Lys Thr Thr Pro Ala
                325                 330                 335

His Ala Pro Gly Asn Thr Ala Thr Gln Ala Thr Gln Cys Leu Thr Thr
                340                 345                 350

Cys Pro Ala Gly Thr Val Leu Asp Asp Gly Thr Ser Thr Asn Phe Val
                355                 360                 365

Ala Ser Ala Thr Glu Cys Thr Lys Cys Ser Ala Gly Phe Phe Ala Ser
                370                 375                 380

Lys Thr Thr Gly Phe Thr Ala Gly Thr Asp Thr Cys Thr Glu Cys Thr
385                 390                 395                 400

Lys Lys Leu Thr Ser Gly Ala Thr Ala Lys Val Tyr Ala Glu Ala Thr
                405                 410                 415
```

```
Gln Lys Val Gln Cys Ala Ser Thr Thr Phe Ala Lys Phe Leu Ser Ile
            420                 425                 430

Ser Leu Leu Phe Ile Ser Phe Tyr Leu Leu
            435                 440

<210> SEQ ID NO 6
<211> LENGTH: 468
<212> TYPE: PRT
<213> ORGANISM: Ichthyophthirius multifiliis

<400> SEQUENCE: 6

Met Lys Asn Asn Ile Leu Val Ile Leu Ile Ser Leu Phe Ile Asn
 1               5                  10                  15

Gln Ile Lys Ser Ala Asn Cys Pro Val Gly Thr Glu Thr Asn Thr Ala
            20                  25                  30

Gly Gln Val Asp Asp Leu Gly Thr Pro Ala Asn Cys Val Asn Cys Gln
            35                  40                  45

Lys Asn Phe Tyr Tyr Asn Ala Ala Ala Phe Val Pro Gly Ala Ser
    50                  55                  60

Thr Cys Thr Pro Cys Pro Gln Lys Lys Asp Ala Gly Ala Gln Pro Asn
 65                 70                  75                  80

Pro Pro Ala Thr Ala Asn Leu Val Thr Gln Cys Asn Val Lys Cys Pro
                85                  90                  95

Ala Gly Thr Ala Ile Ala Gly Gly Ala Thr Asp Tyr Ala Ala Ile Ile
                100                 105                 110

Thr Glu Cys Val Asn Cys Arg Ile Asn Phe Tyr Asn Glu Asn Ala Pro
            115                 120                 125

Asn Phe Asn Ala Gly Ala Ser Thr Cys Thr Ala Cys Pro Val Asn Arg
    130                 135                 140

Val Gly Gly Ala Leu Thr Ala Gly Asn Ala Ala Thr Ile Val Ala Gln
145                 150                 155                 160

Cys Asn Val Ala Cys Pro Thr Gly Thr Ala Leu Asp Asp Gly Val Thr
                165                 170                 175

Thr Asp Tyr Val Arg Ser Phe Thr Glu Cys Val Lys Cys Arg Leu Asn
            180                 185                 190

Phe Tyr Tyr Asn Gly Asn Asn Gly Asn Thr Pro Phe Asn Pro Gly Lys
    195                 200                 205

Ser Gln Cys Thr Pro Cys Pro Ala Ile Lys Pro Ala Asn Val Ala Gln
    210                 215                 220

Ala Thr Leu Gly Asn Asp Ala Thr Ile Thr Ala Gln Cys Asn Val Ala
225                 230                 235                 240

Cys Pro Asp Gly Thr Ile Ser Ala Ala Gly Val Asn Asn Trp Val Ala
                245                 250                 255

Gln Asn Thr Glu Cys Thr Asn Cys Ala Pro Asn Phe Tyr Asn Asn Asn
            260                 265                 270

Ala Pro Asn Phe Asn Pro Gly Asn Ser Thr Cys Leu Pro Cys Pro Ala
    275                 280                 285

Asn Lys Asp Tyr Gly Ala Glu Ala Thr Ala Gly Ala Ala Thr Leu
    290                 295                 300

Ala Lys Gln Cys Asn Ile Ala Cys Pro Asp Gly Thr Ala Ile Ala Ser
305                 310                 315                 320

Gly Ala Thr Asn Tyr Val Ile Leu Gln Thr Glu Cys Leu Asn Cys Ala
                325                 330                 335

Ala Asn Phe Tyr Phe Asp Gly Asn Asn Phe Gln Ala Gly Ser Ser Arg
            340                 345                 350
```

```
Cys Lys Ala Cys Pro Ala Asn Lys Val Gln Gly Ala Val Ala Thr Ala
            355                 360                 365
Gly Gly Thr Ala Thr Leu Ile Ala Gln Cys Ala Leu Glu Cys Pro Ala
        370                 375                 380
Gly Thr Val Leu Thr Asp Gly Thr Thr Ser Thr Tyr Lys Gln Ala Ala
385                 390                 395                 400
Ser Glu Cys Val Lys Cys Ala Ala Asn Phe Tyr Thr Thr Lys Gln Thr
                405                 410                 415
Asp Trp Val Ala Gly Ile Asp Thr Cys Thr Ser Cys Asn Lys Lys Leu
            420                 425                 430
Thr Ser Gly Ala Glu Ala Asn Leu Pro Glu Ser Ala Lys Lys Asn Ile
            435                 440                 445
Gln Cys Asp Phe Ala Asn Phe Leu Ser Ile Ser Leu Leu Leu Ile Ser
        450                 455                 460
Tyr Tyr Leu Leu
465

<210> SEQ ID NO 7
<211> LENGTH: 1326
<212> TYPE: DNA
<213> ORGANISM: Ichthyophthirius multifiliis

<400> SEQUENCE: 7
atgaaatata atattttatt aattttaatt atttctttat ttattaatga attaagagct     60
gttccatgtc ctgatggtac ttagactcaa gctggattga ctgatgtagg tgctgctgat    120
cttggtactt gtgttaattg cagacctaat ttttactata atggtggtgc tgcttaagga    180
gaagctaatg gtaattaacc tttcgcagca ataatgctg ctagaggtat atgtgtacca    240
tgccaaataa acagagtagg ctctgttacc aatgcaggtg acttagctac tttagccaca    300
taatgcagta cttaatgtcc tactggcact gcacttgatg atggagtgac agatgttttt    360
gatagatcag ccgcataatg tgttaaatgc aaacctaact tttactataa tggtggttct    420
ccttaaggtg aagctcctgg cgtttaagtt tttgctgctg gtgctgccgc tgcaggtgtt    480
gctgccgtta ctagttaatg tgtaccttgc caactaaaca aaacgattc tcctgccact    540
gcaggtgcct aagctaattt agccacataa tgtagcaatt aatgtcctac tggcactgta    600
cttgatgatg gagtgacact tgtttttaat acatcagcca cattatgtgt aaatgcaga     660
cctaactttt actataatgg tggttctcct taaggtgaag ctcctggcgt ttaagttttt    720
gctgctggtg ctgccgctgc aggtgttgct gccgttacta gttaatgtgt accttgccaa    780
ataaacaaaa acgattctcc tgccactgca ggtgcctaag ctaatttagc acataatgc     840
agtacttaat gtccaactgg cactgcaatt caagacggag tgacacttgt tttagtaat     900
tcatccacat aatgttctta atgcattgct aattactttt taatggtaa tttcgaagca     960
ggtaaaagtt aatgtttaaa gtgtccagta agtaaaacta ctccagcaca tgctccaggt   1020
aatactgcta cttaagccac ataatgtttg accacatgtc ctgctggtac agtacttgat   1080
gatggaacat caactaattt tgtagcttcc gcaactgaat gtactaaatg ttctgctggc   1140
ttttttgcat caaaaacaac tggttttaca gcaggtactg atacatgtac tgaatgtact   1200
aaaaaattaa cttctggtgc cacagctaaa gtatatgctg aagctactca aaaagtataa   1260
tgcgcctcca ctactttcgc taaattttta tcgatttcct tattatttat ttctttctat   1320
ttattg                                                             1326
```

<210> SEQ ID NO 8
<211> LENGTH: 1404
<212> TYPE: DNA
<213> ORGANISM: Ichthyophthirius multifiliis

<400> SEQUENCE: 8

| | | | | | |
|---|---|---|---|---|---|
| atgaaaaata | atattttagt | aatattgatt | atttcattat | ttatcaatta | aattaaatct | 60 |
| gctaattgtc | ctgttggaac | tgaaactaac | acagccggat | aagttgatga | tctaggaact | 120 |
| cctgcaaatt | gtgttaattg | ttagaaaaac | ttttattata | ataatgctgc | tgctttcgtt | 180 |
| cctggtgcta | gtacgtgtac | accttgtcca | taaaaaaaag | atgctggtgc | ttaaccaaat | 240 |
| ccacctgcta | ctgctaattt | agtcacataa | tgtaacgtta | aatgccctgc | tggtaccgca | 300 |
| attgcaggtg | gagcaacaga | ttatgcagca | ataatcacag | aatgtgttaa | ttgtagaatt | 360 |
| aatttttata | atgaaaatgc | tccaaatttt | aatgcaggtg | ctagtacatg | cacagcttgt | 420 |
| ccggtaaaca | gagttggtgg | tgcattgact | gctggtaatg | ccgctaccat | agtcgcataa | 480 |
| tgtaacgtcg | catgtcctac | tggtactgca | cttgatgatg | gagtaactac | tgattatgtt | 540 |
| agatcattca | cagaatgtgt | taatgtaga | cttaactttt | actataatgg | taataatggt | 600 |
| aatactcctt | tcaatccagg | taaaagttaa | tgcacacctt | gtccggcaat | taaacctgct | 660 |
| aatgttgctt | aagctacttt | aggtaatgat | gctacaataa | ccgcataatg | taacgttgca | 720 |
| tgccctgatg | gtactataag | tgctgctgga | gtaaataatt | gggtagcaca | aaacactgaa | 780 |
| tgtactaatt | gtgctcctaa | cttttacaat | aataatgctc | ctaatttcaa | tccaggtaat | 840 |
| agtacatgcc | taccttgccc | agcaaataaa | gattatggtg | ctgaagccac | tgcaggtggt | 900 |
| gccgctactt | tagccaaata | atgtaatatt | gcatgccctg | atggtactgc | aattgctagt | 960 |
| ggagcaacta | attatgtaat | attataaaca | gaatgtctaa | attgtgctgc | taactttttat | 1020 |
| tttgatggta | ataatttcta | ggcaggaagt | agtagatgca | aagcatgtcc | agcaaataaa | 1080 |
| gtttaaggcg | ctgtagcaac | tgcaggtggt | actgctactt | taattgcata | atgtgccctt | 1140 |
| gaatgccctg | ctggtactgt | actcaccgat | ggaacaacat | ctacttataa | ataagcagca | 1200 |
| tctgaatgtg | ttaaatgtgc | tgccaacttt | tatactacaa | aataaactga | ttgggtagca | 1260 |
| ggtattgata | catgtactag | ttgtaataaa | aaattaactt | ctggcgctga | agctaattta | 1320 |
| cctgaatctg | ctaaaaaaaa | tatataatgt | gatttcgcta | atttttatc | aatttcctta | 1380 |
| ttattgattt | cttattattt | atta | | | | 1404 |

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: primer

<400> SEQUENCE: 9
agccagtccc ttcccgcttc agtgacaa                                         28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 10
cgggatccag cgaactgaat cggtcagct                                        29

```
<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 11
cccagcttga aatataatat tttattaatt ttaatt                               36

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
agggatcctc acaataaata gaaagaaata a                                    31

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 13
aaaaaataaa agtttgaaaa aaa                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 14
gtttagctga ccgattcagt tcg                                             23
```

RECOMBINANT EXPRESSION OF HETEROLOGOUS NUCLEIC ACIDS IN PROTOZOA

This application claims the benefit of U.S. Provisional Application Ser. No. 60/131,121, filed Apr. 27, 1999; U.S. Provisional Application No. 60/118,634, filed Feb. 4, 1999; U.S. Provisional Application No. 60/122,372, filed Mar. 2, 1999; and U.S. Provisional Application No. 60/124,905, filed Mar. 17, 1999, each of which is incorporated herein by reference in its entirety.

CROSS REFERENCE TO RELATED APPLICATION

This application incorporates the content of U.S. patent application Ser. No. 09/497,967, entitled "Diagnostic and Protective Antigen Gene Sequences of Ichthyophthirius," filed Feb. 4, 2000.

STATEMENT OF GOVERNMENT RIGHTS

This invention was made with government support under grants from the National Institutes of Health (GM-54017-03) and the United States Department of Agriculture National Research Initiative Competitive Grants Program (NRICGP) (95-37204-2139). The U.S. government has certain rights in this invention.

FIELD OF THE INVENTION

The present invention relates to the field of recombinant protein production, particularly recombinant protein production in nonpathogenic protozoa, such as the ciliate Tetrahymena.

BACKGROUND OF THE INVENTION

Efficient and high-level recombinant production of heterologous proteins is an important alternative to chemical synthesis and the isolation of proteins from native sources. Recombinant protein production is especially useful when the native protein is normally produced in limited amounts or by sources which are impossible, expensive and/or dangerous to obtain or propagate. Although a number of recombinant expression systems have proven useful for production of various heterologous proteins, none of these systems is universally applicable for the production of all proteins. For instance, *E. coli* appears to lack the ability to provide many post-translational modifications to heterologous proteins. Yeast can provide only some post-translational modifications (e.g., glycosylation patterns), and rapid degradation of heterologous proteins in yeast is common. Additionally, heterologous proteins secreted by yeast may contain long, untrimmed oligosaccharide chains, which sometimes results in biologically inactive or antigenically altered proteins. Moreover, a replacement of the natural mammalian signal peptide with a yeast signal peptide is almost always required for efficient secretion of mammalian proteins by yeast. Expression of heterologous eukaryotic proteins in insect or mammalian cells can be more reliable but both require expensive media for cell propagation. Moreover, cultured insect cells and mammalian cells have a relatively long doubling time compared to conventional bacterial systems such as *E. coli* and certain protozoa such as Tetrahymena.

Protozoa represent an alternative for the recombinant production of heterologous proteins, however few protozoa have been characterized to the extent necessary for routine heterologous protein expression. Well-characterized pathogenic protozoa that have been genetically engineered to express heterologous proteins include *Trypanosoma cruzi, Trypanosoma brucei,* and *Leishmania* spp. A number of shuttle vectors designed for episomal replication and coding region expression in pathogenic protozoa have been developed. An inducible coding region expression system has been established for pathogenic *T. brucei* (Wirtz, E., et al., *Science*, 268, 1179–1183 (1995)). Vectors that allow efficient coding region expression in different hosts like *E. coli* and mammalian cells have also been developed (Al-Qahtani, A., et al., *Nucleic Acids Res.*, 24, 1173–1174 (1996)).

Protozoa are characterized by a glycosylphosphatidylinositol (GPI) anchoring system that allows targeted surface expression, or "display," of various endogenous proteins. Recent experiments in the kinetoplastid *Trypanosoma cruzi* demonstrated that mammalian and protozoan signal peptides function in *T. cruzi* to target a heterologous protein to different cellular compartments, and further showed both secretion and GPI-anchored surface expression in *T. cruzi* of a heterologous protein (Garg et al., *J. Immunol.*, 158: 3293–3302 (1997)). Surface display in *T. cruzi* of chicken ovalbumin (OVA) was achieved using a construct comprising the signal sequence of *T. cruzi*glycoprotein, gp-72, that targets the protein to the endoplasmic reticulum, followed by a coding region for OVA, followed by 45 amino acids of amastigote surface protein I of *T. cruzi* which provided a C-terminal hydrophobic tail containing GPI anchor cleavage/attachment site. The protein thus anchored to the surface of the protozoan via a GPI structure was found to be readily presented in association with class I MHC by parasite-infected host cells.

Heterologous proteins have also been expressed in the slime mold *Dictyostelium discoideum*. A number of proteins have been expressed in this system including surface expression of the malaria circumsporozoite antigen (CSP) (Reymond et al., *J. Biol. Chem.* 1995, 270: 12941–12947); see Williams et al., *Current Opin. Biotechnol.*, 1995, 6:38–542, for a review).

Bioactive cytokines (IL-2 and IFN-γ) have also been produced in both *T. cruzi* and Leishmania (La Flamme et al., *Mol. Biochem. Parasitol.*, 75:25–31 (1995), and Tobin et al., *J. Immunol.*, 150:5059–5069 (1993)) in experiments that suggest that mammalian signal peptides are recognized and processed by these protozoa. However, pathogenic protozoa have not been exploited as a general purpose protein expression system, presumably because they are difficult or expensive to grow in large numbers and/or are infectious to human beings.

The nonpathogenic ciliate protozoan Tetrahymena has also been explored as a vehicle for expression of heterologous genes, but with limited success to date. *T. thermophila* has been successfully transformed using self-replicating palindromic ribosomal DNA (rDNA) purified from macronuclei (Tondravi et al., *Proc. Natl. Acad. Sci. USA* 83:4369–4373 (1986)). Selection of transformants relied on a dominant paromomycin-resistance mutation in the 17S rRNA. rDNA-based shuttle vectors capable of autonomously replicating in Tetrahymena as well as in *E. coli* have also been developed; these plasmids contained a replication origin (ori) from the *T. thermophila* rDNA minichromosome (Yu et al., *Proc. Natl. Acad. Sci. USA* 86:8487–8491 (1989)).

rDNA vectors are usually circular vectors containing both regulatory regions and "coding" regions for Tetrahymena rRNA. A typical somatic rDNA vector contains a 5' non-transcribed sequence (5'-NTS), followed by a "coding" region for rRNA, followed by a 3' nontranscribed sequence (3'-NTS). A transgene is inserted into the 3' NTS. Somatic rDNA vectors contain the macronuclear version of rDNA and transform either by replacement of the macronuclear rDNA gene via homologous recombination or by autonomous replication as an extrachromosomal element. Processing rDNA vectors, on the other hand, contain additional processing signals upstream and downstream from the 5'-NTS and the 3'-NTS, respectively, obtained from the micronuclear version of rDNA. Processing rDNA vectors mimic what happens to the micronucleus rDNA in the newly developing macronucleus. After introduction of the vector into the developing new macronucleus during the sexual process of ciliates known as conjugation, the vector-borne micronuclear rDNA undergoes excision and is maintained as an rDNA minichromosome (Yao et al., Mol. Cell. Biol. 9:1092–1099 (1 989)).

Both somatic and processing rDNA vectors have been used to insert a heterologous nucleic acid into a 3' nontranscribed spacer region of rDNA. For example, M.-C. Yao et al. (Proc. Nat'l. Acad. Sci. USA 88:9493–9497 (1991)) expressed cycloheximide resistance in Tetrahymena using an rDNA vector having the rpl29 cycloheximide resistant gene from T. thermophila inserted into the 3' nontranscribed spacer region (NTS) of the rDNA sequence. Similarly, P. Blomberg et al. expressed neomycin resistance in T. thermophila using an rDNA vector having the neo gene inserted into the 3' NTS, under control of rpl29 flanking sequences (Mol. Cell. Biol., 17:7237–7247 (1997)).

Gaertig et al. described an rDNA-based shuttle vector, E. coli vector pH4T2, that contains two replication origin (ori) fragments, followed by a 300 base pair 5' untranslated region obtained from the HHF1 gene of Tetrahymena, followed by the prokaryotic gene for neomycin resistance, neo, followed by a 3' untranslated region from BTU2 from Tetrahymena (J. Gaertig et al., Nucleic Acids Res. 22:5391–5398 (1994)). Haddad et al. reported a small circular rDNA-based vector containing a repeat of the replication origin of rDNA (i.e., a 5' NTS), a neo2 gene cassette (consisting of the neo gene under the control of histone HHF1 promoter and the BTU2 transcription terminator) as a selectable marker, and a green fluorescent protein (GFP) cassette (also under control of HHF1 promoter and BTU2 terminator) (A. Haddad et al., Proc. Nat'l. Acad. Sci. USA 94:10675–10680 (1997)). Rusconi et al. reported a circular vector containing the rDNA replication origin, neo2 cassette, and a tRNA gene (Genes Dev. 10:2870–2880, 1996)).

A typical rDNA-based vector is a circular bacterial vector that contains a 5' NTS comprising two or more of ori sequences from Tetrahymena rDNA, followed by a selectable cassette marker such as the neo 2 cassette (Gaertig et al., Nucleic. Acids Res. 22:5391–5398 (1994). A nucleic acid fragment containing a heterologous coding region such as a transgene, flanked by a 5' untranslated region of a Tetrahymena gene (most often the ~30 bp 5' untranslated region of the HHF1 gene of Tetrahymena) and a 3' untranslated region of a Tetrahymena gene (most often ~300 bp of the 3' untranslated region of the Tetrahymena gene BTU2), is typically inserted downstream of the selectable marker.

An rDNA construct that contains relatively short 5' and 3' untranslated sequences from two different protein coding genes of Tetrahymena, such as HHF1 and BTU2, is unlikely to integrate into the Tetrahymena genome via homologous recombination at the corresponding protein-coding loci. It is more likely to insert into Tetrahymena rDNA as a result of a single crossover event which involves the replication origin fragment. In addition, an rDNA-based vector can be maintained as an extrachromosomal element; the ori from Tetrahymena rDNA is known to support extrachromosomal replication. The marker gene (e.g., neo), and the transgene, if present, are therefore most likely expressed from the transforming rDNA-based plasmid and/or as a result of insertion into genomic rDNA, and not by recombination with endogenous genes other than rDNA.

Due to frequent and unpredictable integration of sequences from rDNA vector and rDNA-based vectors into the native rDNA, however, levels of expression of recombinant gene products are presumed to be highly variable. See J. Gaertig et al., Nucleic Acids Res. 22:5391–5398 (1994); R. W. Kahn et al., Proc. Natl. Acad. Sci. USA 90:9295–9299 (1993); W. J. Pan et al., Nucleic Acids Res. 23:1561–1569 (1995); and W. J. Pan et al., Mol. Cell Biol., 15:3372–3381 (1995). When relying on rDNA vectors for transformation, there is no way to control the level of integration into the host chromosome, hence no way to control copy number and, as a result, the expression level of a heterologous protein. Tetrahymena contain about 45 copies of each protein coding gene in the macronucleus, and each copy contains about 10,000 pallindromic copies per macronucleus. Thus, using either of these types of vectors, it is possible for a transgene to integrate at a similar copy number (10,000+). Overexpression of a transgene can be toxic to the protozoan host cell. Moreover, the loss of transgenes using these vectors cannot be prevented since this recombinant method generally lacks a reliable and sustainable means for selection. For example, a vector can contain both a transgene and a selectable marker, and both may initially integrate into the protozoan host genome. However, subsequent cross-over events can eliminate the transgene while leaving the marker gene in the host genome, resulting in selection of cells that do not necessarily contain the transgene.

A protein expression system that provides for the efficient expression and isolation of both prokaryotic and eukaryotic heterologous proteins in a nonpathogenic protozoan host is needed. In particular, a protein expression system that could provide surface expression of a heterologous prokaryotic or eukaryotic protein would constitute a much desired advance in the art.

SUMMARY OF THE INVENTION

The invention provides a protein expression system that utilizes a protozoan for the production of eukaryotic and prokaryotic polypeptides, including proteins. In one aspect, the recombinant protein expression system of the invention includes a transgenic protozoan host cell that is resistant to paclitaxel, wherein the host cell comprises a heterologous nucleic acid encoding a polypeptide. The recombinant protozoan host cell of this aspect of the invention is selectable by negative selection using paclitaxel. The protozoan host cell that is transformed with the heterologous nucleic acid is preferably a Tetrahymena host cell containing a btu1-1K350M β-tubulin allele. In another aspect, the recombinant protein expression system of the invention includes a transgenic ciliated protozoan host cell that contains a heterologous protein displayed on the plasma membrane surface of the host cell. Preferably, the surface-displayed heterologous protein is attached to the plasma membrane by a GPI anchor derived from an Ichthyophthirius multifiliis i-antigen.

Also provided by the invention is a novel protein expression vector. The vector contains a 5' flanking region followed by a heterologous nucleic acid encoding a polypeptide comprising at least one targeting amino acid sequence encoded by a portion of an i-antigen-encoding nucleotide sequence from I. multifiliis, followed by a 3' flanking region.

At least a portion of each of the 5' flanking region and the 3' flanking region is complementary to an endogenous gene of an intended host, so as to allow for integration into endogenous gene by way of homologous recombination. In a preferred embodiment, the 5' flanking region and the 3' flanking region each contain a nucleic acid sequence selected from at least a portion of the Tetrahymena genes HHF1, rpl29, BTU1, BTU2, SerH3 and the gene encoding actin.

The invention further provides a transgenic Tetrahymena that contains at least a portion of an *I. multifiliis* i-antigen protein, preferably a portion of an *I. multifiliis* i-antigen protein that includes a targeting amino acid sequence.

Further, the invention provides a transgenic cell containing a heterologous protein that includes at least one targeting amino acid sequence encoded by an i-antigen-encoding nucleotide sequence from *I. multifiliis*. The transgenic cell is not limited and can be a bacterial cell, a fungus cell, a protozoan cell, or an animal cell, for example. The targeting amino acid sequence is an N-terminal targeting sequence, a GPI cleavage/attachment sequence, or both. Preferably, the the heterologous protein is displayed on the surface of the plasma membrane of the transgenic cell.

The invention also provides a method for making a polyclonal antibody. An antigenic polypeptide is expressed on the surface of the plasma membrane of a transgenic protozoan host cell, then the transgenic protozoan host cell is administered to an animal to generate an antibody response to the antigenic polypeptide. In another aspect of this embodiment of the invention, the antigenic polypeptide is cleaved from the surface of the host cell, isolated, then administered to an animal to generate an antibody response to the antigenic polypeptide. Optionally, the antibody is isolated from the animal.

The invention further provides a method for detecting antibodies to an antigenic polypeptide that involves expressing the antigenic polypeptide on the surface of a transgenic protozoan host cell; exposing the protozoan host cell to an antibody; and determining whether the protozoan host cell is immobilized. Immobilization of the protozoan host cell is indicative of the presence of antibodies to the antigenic polypeptide. This method can be used to detect antibodies to a pathogenic parasite in the bodily fluid of a patient suspected of being infected with the parasite.

Also provided by the invention is a method for screening drugs for the ability to bind a polypeptide. Preferably, the drug to be screened is one that has cross-linking capability, but the drug screening method of the invention is not limited to just those drugs. The polypeptide is expressed on the surface of a transgenic protozoan host cell and the host cell is exposed to the drug. Binding of the drug is evidenced by an observable change in the swimming pattern of the host cell which may, but need not, included complete immobilization of the host cell. In the case of a drug having cross-linking capability, the drug is caused to cross-link. Cross-linking of the drug will generally immobilize the host cell, indicating that the drug has bound to the polypeptide.

The invention further provides a vaccine containing a transgenic nonpathogenic immunogenic protozoan which exhibits a surface-displayed antigenic polypeptide. The vaccine can be a live vaccine or a killed vaccine. In a preferred embodiment, the nonpathogenic immunogenic protozoan is Tetrahymena and the antigenic polypeptide includes at least an antigenic portion of an *I. multifiliis* i-antigen protein.

Also provided by the invention is a method for stimulating an immune response in a vertebrate that includes delivering to the vertebrate a transgenic nonpathogenic immunogenic protozoan comprising a surface-displayed antigenic polypeptide.

The invention further includes a novel recombinant method for producing a polypeptide. A heterologous nucleic acid encoding the polypeptide is introduced into a protozoan host cell, preferably a protozoan host cell that is sensitive to paclitaxel, to yield a transgenic protozoan host cell selectable by negative selection using paclitaxel. The polypeptide is then expressed in the transgenic protozoan host cell. Optionally, the polypeptide is displayed on the plasma membrane of the transgenic protozoan host cell and cleaved to release the polypeptide. Also optionally, the polypeptide is isolated from the transgenic protozoan host cell. In another aspect, the recombinant method for producing a polypeptide includes introducing a heterologous nucleic acid encoding the polypeptide into a host cell to yield a transgenic host cell, wherein the polypeptide comprises at least one targeting amino acid sequence encoded by an i-antigen-encoding nucleotide sequence from *I. multifiliis*, then expressing the polypeptide in the transgenic host cell.

Definitions

An "expression vector" is a nucleic acid molecule containing a nucleotide sequence encoding a polypeptide that is capable of being expressed in a host cell. Generally, when the term "vector" or "vector construct" is used herein, an expression vector is intended. Typically, an expression vector is a DNA molecule that contains a gene, and expression of the gene is under the control of regulatory elements that can, but need not, include one or more constitutive or inducible promoters, tissue-specific regulatory elements, and enhancers. Such a gene or other nucleic acid fragment is said to be "operably linked" to the regulatory elements.

A "cloning vector" is a nucleic acid molecule, typically a DNA molecule, that contains one or more restriction endonuclease recognition sites at which foreign nucleic acid fragments can be inserted in a determinable fashion without loss of an essential biological function of the vector, and often contain a nucleotide sequence encoding a detectable and/or a selectable marker (i.e., "marker genes") that can be used to identify and/or select cells transformed with the cloning vector. Marker genes typically include nucleic acid fragments that encode polypeptides which can confer a phenotypic characteristic to the transformed cell, such as antibiotic resistance, test compound metabolism, and the like.

Cloning and expression vectors can include naturally occurring or modified DNA or RNA, and can take the form of a plasmid, cosmid, or bacteriophage. Vectors can be linear or circular.

The terms "exogenous" or "heterologous," which are used interchangeably herein, denote some item, typically a nucleic acid fragment or a protein, that is foreign to its surroundings. In particular, the terms apply to nucleic acid fragments that have been inserted into a host organism, but are not found in the normal genetic complement (i.e., genome) of the host organism. A nucleic acid fragment that is heterologous with respect to an organism into which it has been inserted or transferred is sometimes referred to herein as a "transgene." A "transgenic" organism (whether microorganism or an animal) is a host organism that has been genetically engineered to contain exogenous (heterologous) nucleic acid fragments, including vectors. Introduction of the heterologous nucleic acids into a host cell to create a transgenic cell is not limited to any particular mode of delivery, but includes, for example, microinjection, adsorption, electroporation, particle gun bombardment, liposome-mediated delivery and the use of viral and retroviral vectors.

Preferably, the heterologous nucleic acid fragments are stably integrated into the host genome, but they may, alternatively, be maintained extrachromosomally. The heterologous nucleic acid fragments may but need not be inheritable.

A nucleic acid fragment is "excised" from genomic DNA by isolating genomic DNA from the host, as by cutting the nucleic acid fragment at one or more predetermined sites, for example at a restriction enzyme recognition site.

An excised nucleic acid fragment can be ligated into a vector and assayed for recombination. Successful recombination can be detected, either directly or indirectly, as by using a laboratory assay or other detection procedure. Preferably, the presence or absence of a recombinant nucleic acid fragment is detectable by way of a chemical or biological assay. Detection can be mediated through the use of "reporter" nucleic acid fragments typically contained in the vector, such as a particular nucleic acid fragment that can confer metabolic pathways for particular nutrient utilization or antibiotic resistance. For example, in a lac operon-based mutation detection system commonly used in *E. coli*, a mutation in a lacI mutation target gene affects the expression of the lacZ reporter gene, and expression of the reporter gene is detectable in an *E. coli* host by assaying the ability of the host to produce the lacZ gene product (β-galactosidase) and thus metabolize a chromogenic substrate.

An "immunogenic" or "immune system stimulating" polypeptide, also referred to as a polypeptide antigen or an antigenic polypeptide, is one that activates at least one cell type of the immune system of an animal, including phagocytic cells such as macrophages, as well as T cells and B cells. An example of an immune-stimulating ciliated protozoan is one that displays a polypeptide antigen on its cell surface such that an immune response to the antigen is elicited in an animal exposed to the immune-stimulating protozoan. Likewise, an immunogenic composition comprises an immunogenic polypeptide and optionally contains a pharmaceutically acceptable buffer, such as phosphate buffered saline (PBS) or another buffer, recognized in the art as suitable and safe for introduction of proteins into a host to stimulate the immune system.

As used herein, the term "effective amount" refers to an amount of a substance that is effective to produce a desired result. For instance, an effective amount of an immune-stimulating composition is one that is effective to activate cells of the immune system, including phagocytic cells such as macrophages, as well as T cells and B cells. The actual amount varies depending upon the health and physical condition of a subject's immune system, i.e., to synthesize antibodies, the degree of protection desired, the formulation prepared and other relevant factors. It is expected that the amount will fall in a relatively broad range that can be determined through routine trials.

As used herein, the term "polypeptide" refers to a chain of amino acids linked through peptide bonds between an α-carboxyl carbon of one amino acid residue and the α-nitrogen of the next amino acid. The term polypeptide is used herein as a general term that includes polypeptides of any length, including what are commonly referred to in the art as peptides, oligopeptides, and proteins. A "protein" contains one or more polypeptide chains that fold to adopt a particular conformation that has some type of biological activity or function. The properties and function of any particular protein are generally determined by the physical and chemical properties of the molecule. The order of the nucleotides in a nucleic acid fragment determines the order of amino acid residues in a polypeptide and protein, i.e., the nucleic acid fragment "encodes" the polypeptide (protein).

BRIEF DESCRIPTION OF THE DRAWINGS

FIG. 2A–2B show full restriction maps of (a) BTU1::neo1 construct (SEQ ID NO:1 and its complement, SEQ ID NO:2) and (b) pBICH3 vector construct (SEQ ID NO:3), as shown in as shown in FIG. 1 (and its complement, SEQ ID NO:4); positions of restriction endonucleases sites are shown, with unique sites underlined; translation start and stop sites are boxed.

FIG. 3A–3B show (a) an alignment of the deduced amino acid sequences of 48 kD (SEQ ID NO:5, upper line) and 55 kD (SEQ ID NO:6, lower line) i-antigens of *I. multifiliis*, where asterisks indicate identities between the two deduced protein sequences, double dots indicate highly homologous amino acids, and single dots indicate moderately homologous amino acids; boxes indicate conserved regions; (b) an alignment of the nucleotide sequences of the coding regions of the IAG48 [G1] gene (SEQ ID NO:7, upper line) and the IAG55 [G5] gene (SEQ ID NO:8, lower line) of *I. multifiliis*, where asterisks indicate identities between the two nucleotide sequences.

FIG. 5 is a Western blot analysis identifying a putative 48 kD *I. multifiliis* i-antigen expressed by transgenic *T. thermophila.*

FIG. 6A–6D are photomicrographs using immunofluorescence for detection of surface expression of a putative 48 kD *I. multifiliis* i-antigen in transgenic *T. thermophila.*

FIGS. 7A–7B show Western blots of (a) total protein extracts of transformant cells; and (b) total culture medium from which transformed cells were removed, probed using anti- *I. multifiliis* i-antigen antibodies; the load of the medium shown in (b) is about 1/30 th of the load of the cells shown in (a).

FIG. 8 shows a Western blot of a total protein extract from Tetrahymena transformed with chicken ovalbumin, probed with anti-chicken ovalbumin antibodies.

FIG. 9 is Western blot showing expression and secretion from a transformed Tetrahymena of a G1 i-antigen with C-terminal truncation.

FIG. 10A–10B show ELISA results for fish vaccinated with Tetrahymena expressing (a) membrane associated G1 i-antigen and (b) secretary form of G1 i-antigen.

FIG. 11 is a 10× magnification of serotype A *I. multifiliis* an immobilization test conducted using sera (1:20 dilution) from (a) fish vaccinated with live Tetrahymena expressing neo ("anti-live Tneo," the negative control) and (b) fish vaccinated with live Tetrahymena expressing the full-length 48 kD i-antigen protein from a G1 *I. multifiliis* isolate ("anti-live TG1")

DETAILED DESCRIPTION

Figure 1:
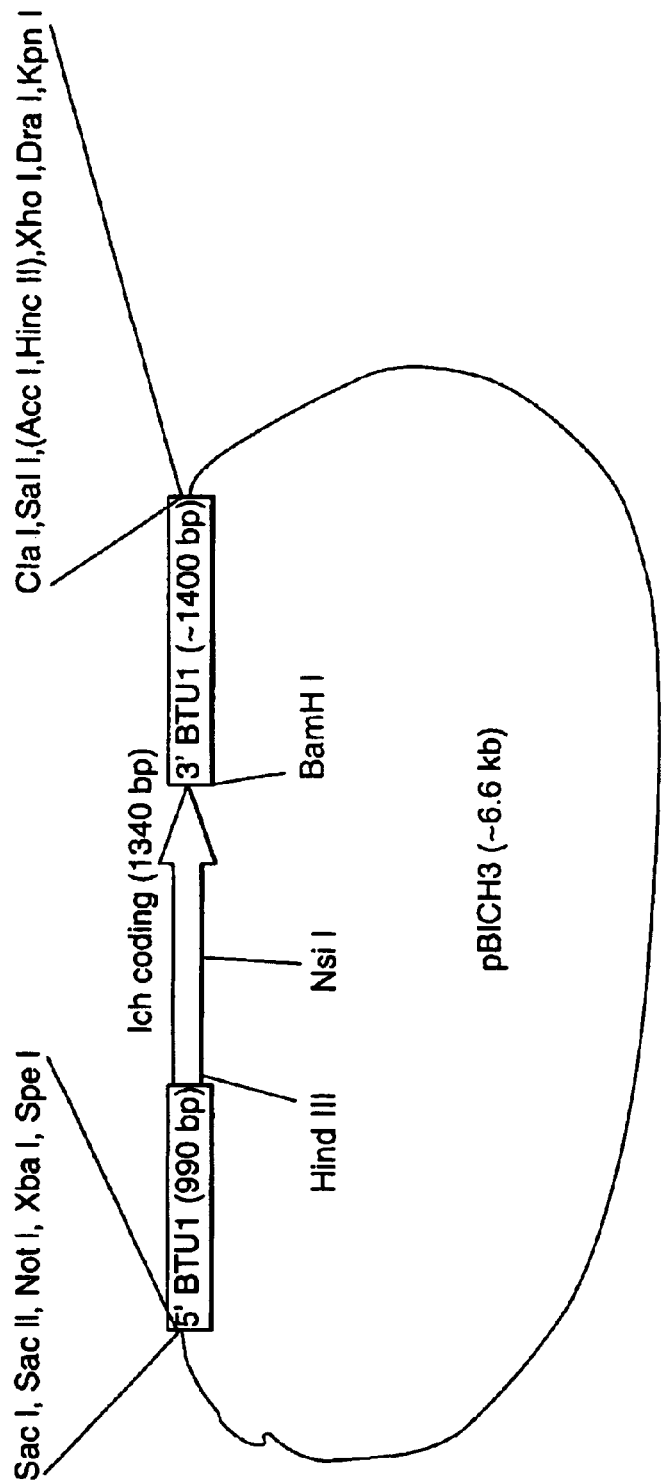
FIG. 1 is a schematic of the vector pBICH3.
Figure 4:
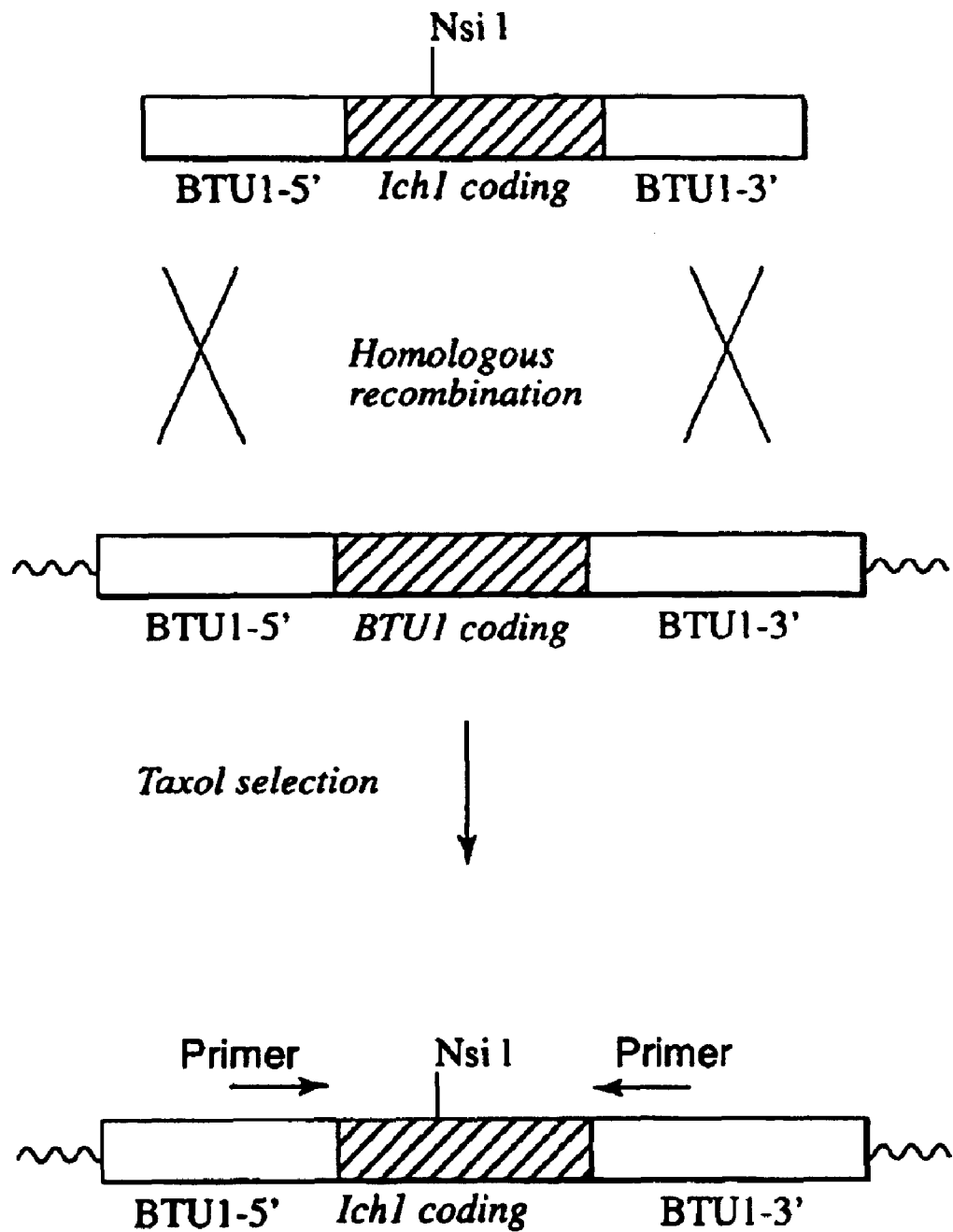
FIG. 4 is a schematic showing the experimental design used to introduce the Ichthyophthirius i-antigen into the BTU1 locus of *T. thermophila*. A hybrid gene composed of the *I. multifiliis* i-antigen coding sequence inserted between regulatory sequences of BTU1 is integrated into the endogenous paclitaxel-sensitive BTU1 locus by homologous recombination.

The invention provides a protein expression system that utilizes a protozoan, preferably a nonpathogenic ciliate, more preferably Tetrahymena, for the production of eukaryotic and prokaryotic polypeptides, including proteins. The protein expression system of the invention is useful to produce virtually any polypeptide for any purpose. It is suited to both large scale and analytical scale production of recombinant polypeptides, and is particularly useful for expression of polypeptides that are difficult to produce in conventional recombinant protein expression systems.

Ciliated Protozoa

Protozoa, particularly nonpathogenic protozoa, are well-suited for use as recombinant protein expression systems. Not only are many protozoa capable of secreting proteins, but they often contain an anchoring system (known as a GPI anchor) that allows surface expression, or "display," of various endogenous proteins without secretion. Some protozoa, like Tetrahymena, have major membrane proteins that are GPI-anchored; they in essence contain a GPI-anchored coat of surface-displayed proteins on the plasma membrane. These displayed proteins can often be cleaved from the cell surface of a protozoan by phospholipase C (typically isolated from *B. thuringiensis*). Many nonpathogenic protozoa are fast-growing and inexpensive to culture. Nonpathogenic ciliated protozoa can be environmentally friendly if the desired genetic modifications are performed within their somatic genomes localized to the macronucleous; heterologous nucleic acids that have integrated into the macronucleus, such as those that disrupt the BTU1 gene in Tetrahymena, are lost when the protozoan undergoes the sexual process of conjugation. The old macronucleus disintegrates, and the new macronucleus is formed as a result of differentiation of the zygotic micronucleus. As a result, a nucleic acid that had integrated into the macronucleus is not inherited or otherwise perpetuated, a feature which enhances environmental safety by preventing heterologous nucleic acids from entering the gene pool.

Protozoa are also more effective than yeast in providing post-translational modifications to certain eukaryotic proteins. For example, yeast apparently lacks a number of post-translational modifications typically found on tubulins, such as acetylation of Lys40 in α-tubulin, polyglutamylation and polyglycylation of α- and β-tubulin (T. MacRae et al., *Eur. J. Biochem.* 244:265–278 (1997)). On the other hand, these tubulin modifications were found in Tetrahymena and other ciliates like Paramecium (J. Gaertig et al., *J. Cell Biol.* 129:1301–1310 (1995)); V. Redeker et al., *Science* 266:1688–1691 (1994)). Ciliates, in particular, are excellent candidates for heterologous polypeptide expression; the presence of cilia vastly increases cell surface area, providing more opportunity for expression of GPI-anchored polypeptides.

A transgenic nonpathogenic ciliated protozoan of the invention is preferably a free-living ciliate; that is, it can propagate without a host. Examples of nonpathogenic free-living ciliates include Tetrahymena, Paramecium, Blepharisma, Colpidium, Euplotes, Stylonichia and Oxytricha. More preferably, the free-living transgenic nonpathogenic ciliate is Tetrahymena. Tetrahymena can be grown in large volume cultures using a variety of inexpensive media including skimmed milk powder. Generation time is short (1.5–3 hr) and cells attain remarkably high density given their size (~50 μm in length). Indeed, it has been reported that fermentation in perfused bioreactors has permitted growth to concentrations as high as $2.2 \times 10^7$ cells/ml, equivalent to a dry weight of 48 g/l. See, e.g., T. Kiy et al., *Appl. Microbiol. & Biotech.*, 38:141–146 (1992). Further, Tetrahymena has the ability to secrete proteins into the growth medium, and mutant strains defective in the release of hydrolytic enzymes have been isolated (P. Hunseler et al., *Dev. Genet.* 13:167–173 (1992). Mutant strains lacking or exhibiting reduced levels of secreted hydrolytic proteases are preferred for surface expression or secretion of a heterologous polypeptide that is sensitive to proteolysis by hydrolytic enzymes. Finally, a large part of the cell metabolism is devoted to the production of abundant surface membrane proteins known as immobilization antigens (i-antigens), whose expression is tightly regulated by environmental conditions. This feature makes Tetrahymena a preferred host because expression of a heterologous protein containing an endogenous GPI anchor can potentially be controlled by changes in temperature. J. R. Preer, *The Molecular Biology of Ciliated Protozoa*, pp. 301–339 (ed. J. G. Gall), Academic Press, New York (1986).

Tetrahymena, which has genomic DNA generally on the order of 75% A-T, offers additional advantages as a host system for the cloning and expression of genes from other organisms with AT-rich genomes. For example, a number of human pathogens (for example, malarial plasmodia, mycoplasmas, etc.) have extremely AT-rich genomes. Genomic DNA contains four bases (A, T, C, G), and DNA duplexes typically hybridize by means of A-T and G-C base pairing. In the genomes of many organisms, the amounts of A, T, C, and G are relatively equal, thus their genomic DNA contains roughly the same number of A-T and G-C base pairs. "AT-rich" genomes or nucleic acids are genomes or nucleic acids that have an AT content of more than about 50% of the total bases in the fragment, preferably about 65% or more, and more preferably about 70% or more. Notably, AT-rich fragments are inherently unstable in conventional systems such as *E. coli*, making cloning genes from AT-rich organisms into conventional systems difficult. As an AT-rich host, however, *T. thermophila* is expected to stably maintain heterologous nucleic acid fragments having "AT rich" sequences.

Tetrahymena, like other ciliates, utilizes UAA and UAG as codons for the amino acid glutamine, while most other organisms recognize those as termination codons. Thus, Tetrahymena is particularly useful to express heterologous genes that are derived from other ciliates. Expression of ciliate genes in conventional (eukaryotic and prokaryotic) protein expression systems often requires that the ciliate gene be mutated so as to utilize the conventional nucleic acid code in order to produce a full-length protein.

Furthermore, immobilization of Tetrahymena in culture with specific antibodies offers a potential bioassay for detection of specific antibodies in biological samples that would shorten the time and lower the cost for screening, and would obviate the need for chemical detection substrates used in more standard diagnostic tests.

Transformation of the Protozoan Host With a Heterologous Nucleic Acid

The protozoan host is transformed with a heterologous nucleic acid, which can be either integrated into the host's genome or maintained extrachromosomally on an autonomous plasmid or other construct. The heterologous nucleic acid encodes a polypeptide that is expressed by the resulting transgenic host. There is no limitation on the type of heterologous polypeptide that can be expressed in the protozoan host. The polypeptide coding region of the vector construct can, for example, be a coding region derived from a pathogenic protozoan, or from another eukaryotic or prokaryotic organism. As already noted, a protozoan host such as Tetrahymena is especially useful as a vehicle for creating an expression library for organisms with AT-rich genomes, particularly pathogenic organisms, such as Plasmodium (the protozoan agent of malaria). Genomic fragments from these organisms are difficult to clone and stably maintain in E. coli. Another example of a preferred heterologous nucleic acid sequence is one that encodes at least a portion of an antigenic polypeptide in that is capable of stimulating an immune response in an animal upon exposure to the polypeptide. In a particularly preferred embodiment of the invention, a transgenic ciliated protozoan displays an antigenic polypeptide on its cell surface.

The location of the expressed polypeptide is determined by the protein targeting sequences, if any, encoded by the heterologous nucleic acid and thereby incorporated into the resulting polypeptide. The heterologous polypeptide can accumulate in the cytosol, can be secreted from the host cell, or can be embedded in or anchored to the host cell plasma membrane, as is further described below.

Preferably, the heterologous nucleic acid is introduced into the ciliate host on an expression vector that is capable of integrating into the host's genome. In a particularly preferred embodiment of the invention, expression vectors operate by way of homologous recombination with a highly expressed gene that is endogenous to the protozoan host, such as a β-tubulin gene as described below. On the other hand, an expression vector that does not rely on the regulatory sequences of an endogenous gene for expression can, optionally, be maintained extrachromosomally in the ciliated protozoan host cell. An expression vector maintained as an extrachromosomal element is preferably an rDNA-based vector containing ori from Tetrahymena rDNA, which is known to support extrachromosomal replication. Such a vector further includes a 5' regulatory region from an endogenous Tetrahymena gene containing a promoter region operably linked to the heterologous coding region and, optionally, a 3' regulatory region from the same or, preferably, a different Tetrahymena gene. For example, expression vectors can contain regulatory regions from ciliate genes such as HHF1, rpl29, BTU1, BTU2, SerH3, and those encoding actin.

Expression Vectors

Expression vectors useful for transforming protozoa in accordance with the invention can be generally classified into three types: replacement vectors, rDNA vectors, and rDNA-based vectors. Replacement vectors accomplish DNA-mediated transformation by replacing or altering endogenous genes using homologous recombination. Integration of the heterologous nucleic acid into the host's genome at the targeted site is accomplished via homologous recombination involving a double crossover event with the vector containing the heterologous nucleic acid. An example of an expression vector useful for genomic incorporation of a heterologous nucleic acid by replacement is one that includes a heterologous coding sequence flanked by portions of the endogenous BTU1 gene of Tetrahymena.

A replacement vector thus preferably includes a 5' region, followed by a heterologous coding region, followed by a 3' region, wherein at least a portion of each of the 5' and 3' regions is complementary to 5' and 3' regions on an endogenous gene of the host, to allow for genomic integration of the heterologous coding region via homologous recombination. The 5' and 3' regions of the vector optionally contain regulatory elements, such as a promoter and a terminator; alternatively, the necessary regulatory elements are supplied by the endogenous gene into which the heterologous coding region integrates. Preferably, the 5' and 3' regions of an expression vector useful in Tetrahymena include sequences complementary to the BTU1, BTU2, SerH3 or HHF1 genes of Tetrahymena. Optionally, a replacement vector further includes a nucleotide sequence encoding a selectable marker, such as neo. Preferably the marker sequence is under the control of its own promoter, thus another regulatory region is included 5' to the sequence encoding the selectable marker; and example is the neo2 cassette.

β-Tubulin is a cytosolic protein in Tetrahymena that is a monomeric constituent of cytoskeletal elements known as microtubules. An α/β tubulin dimer is the building block of microtubules, and both α-tubulin and β-tubulin are essential proteins. T. thermophila expresses two major β-tubulin genes, BTU1 and BTU2, which encode identical β-tubulin proteins (J. Gaertig et al., Cell Mot. Cytoskel., 25:245–253 (1993)). It was determined that either of these two genes (but not both at once) can be disrupted without a detectable change in the cell phenotype.

Substitution of lysine (K) 350 by methionine (M) in the BTU1 gene to yield the Btu1-1K350M allele confers increased resistance to several microtubule-depolymerizing drugs (oryzalin, colchicine, vinblastin), and increased sensitivity to a microtubule-stabilizing agent, paclitaxel (J. Gaertig et al., Proc. Nat'l. Acad. Sci. USA 91:4549–4553 (1994)). The phenotype of the Btu1-1K350M allele is expressed even in the presence of wild-type copies of the second β-tubulin gene, BTU2. Cells carrying the btu1-1K350Mallele can be transformed to paclitaxel resistance by gene replacement of btu1-1K350M with a wild-type BTU1 gene fragment, thus eliminating the need to incorporate a means for positive selection. Because the BTU1 gene is not essential for survival, any loss-of-function mutation of btu1-1K350M in the presence of wild-type BTU2 gene confers paclitaxel resistance.

It has been discovered as part of this invention that heterologous nucleic acids can be inserted into a β-tubulin gene of T. thermophila for successful cell-surface expression that is advantageously maintained by way of negative selection. Expression of a heterologous protein in T. thermophila is preferably accomplished using a transgenic T. thermophila that contains the negatively selectable Btu1-1K350M allele of the β-tubulin gene (BTU1) to direct heterologous nucleic acid fragments to this highly expressed locus by homologous recombination. A transformed cell line can thus be readily identified by paclitaxel selection, in that successful transformation restores paclitaxel resistence.

Accordingly, a preferred expression vector in accordance with the present invention preferably includes a nucleic acid fragment capable of integration into either the BTU1 or BTU2 gene of T. thermophila, preferably the BTU1 gene, more preferably the Btu1-1K350M allele of the BTU1 gene. The BTU1 gene contains 5' and 3' regulatory regions that flank the coding region; hence the preferred expression vector contains at least a portion of each of these regulatory regions, which portions are sufficient to allow for homologous recombination with the endogenous gene. The flanking sequences of BTU1 that are included in the vector (e.g., FIGS. 1 and 2) allow for targeting of the heterologous coding region into the endogenous BTU1 gene via homologous recombination with the endogenous gene.

The protozoan host to be transformed with the vector is preferably T. thermophila which contains a β-tubulin gene (BTU1) wherein lysine 350 is substituted by methionine (btu1-1K350M). The expression vector disrupts the btu1-1K350M gene by homologous recombination-mediated insertion of a heterologous nucleic acid, thereby restoring resistence to paclitaxel in the resulting transgenic host.

Homologous recombination can take place at sites within the coding region of the highly expressed target gene or at sites that flank the gene target, which include but are not limited to flanking regulatory regions; all that is required is that the expression of the target gene be disrupted. When BTU1 is the target gene, a second β-tubulin gene (BTU2) remains available to provide the essential function of β-tubulin in vivo, such that BTU1 can be fully replaced with btu1-1K350M (or heterologous nucleic acid sequence) without adverse effects to the organism. When T. thermophila having the btu1-1K350M allele of the BTU1 gene is used as the host, transformants can be maintained by negative selection, since transformed mutants are not sensitive to paclitaxel while nontransformed mutants are. Transformants are this readily identified by negative selection by growth on in media containing paclitaxel; there is no need to engineer drug-resistance or other means of selection into the genome of the transgenic host. Additionally, there is no limitation on the nature of the heterologous nucleic acid sequence that can be targeted to the BTU1 locus of T. thermophila.

The heterologous nucleic acid sequence that is incorporated into the host genome in accordance with the present invention optionally encodes a selectable marker. For example, an expression vector can include a BTU1 derivative, BTU1-2::noe1 (see FIG. 2) which substitutes the coding region of a prokaryotic gene, noe1, for that of BTU1, to provide a means for positive selection of transformants. The noe1 gene confers resistance to paromomycin in T. thermophila, and a BTU1-2::noe1 fragment can then be used to generate BTU1 gene knockouts by homologous recombination and positive selection with paromomycin. Of course, when the host organism is a T. thermophila mutant containing the btu1-1K350M allele of BTU1, transformants are identified with negative selection and a positive selection is not necessary.

Optionally, a replacement vector for use in Tetrahymena includes a temperature-regulatable promoter region to facilitate controlled expression of the heterologous coding region. The temperature-regulatable promoter can be supplied instead of or in addition to another promoter, such as the promoter region of the endogenous BTU1 gene. The temperature-regulatable promoter is preferably positioned within the 5' untranslated region of the vector, more preferably between a 5' BTU region and the heterologous coding region. Because Tetrahymena SerH3 encodes an i-antigen whose expression is temperature dependent, the 5' regulatory region of the SerH3 gene of Tetrahymena may include a temperature-regulatable promoter that is useful in the invention.

Also optionally, the replacement vector contains a second promoter region, in addition to the promoter region supplied by the endogenous target gene, for enhanced expression of the heterologous protein.

In a representative example of the invention, the expression vector (pBICH3, FIG. 1) includes the entire coding sequence of the i-antigen gene inserted in a correct translational frame between the regulatory sequences of the BTU1 gene. This vector contains a complete plasmid sequence commercially available under the trade designation pBLUE-SCRIPT SK (+), from Stratagene, La Jolla, Calif., and is generally useful for integration of any heterologous coding region into the β-tubulin gene of T. thermophilis. One skilled in the art will recognize that other plasmids may be equally suitable, such as those commercially available under the trade designation pCRScript, from Stratagene, La Jolla, Calif.; pGEM from Promega, Madison, Wis.; and pCRII, from Invitrogen, Carlsbad, Calif.

Figure 2A:
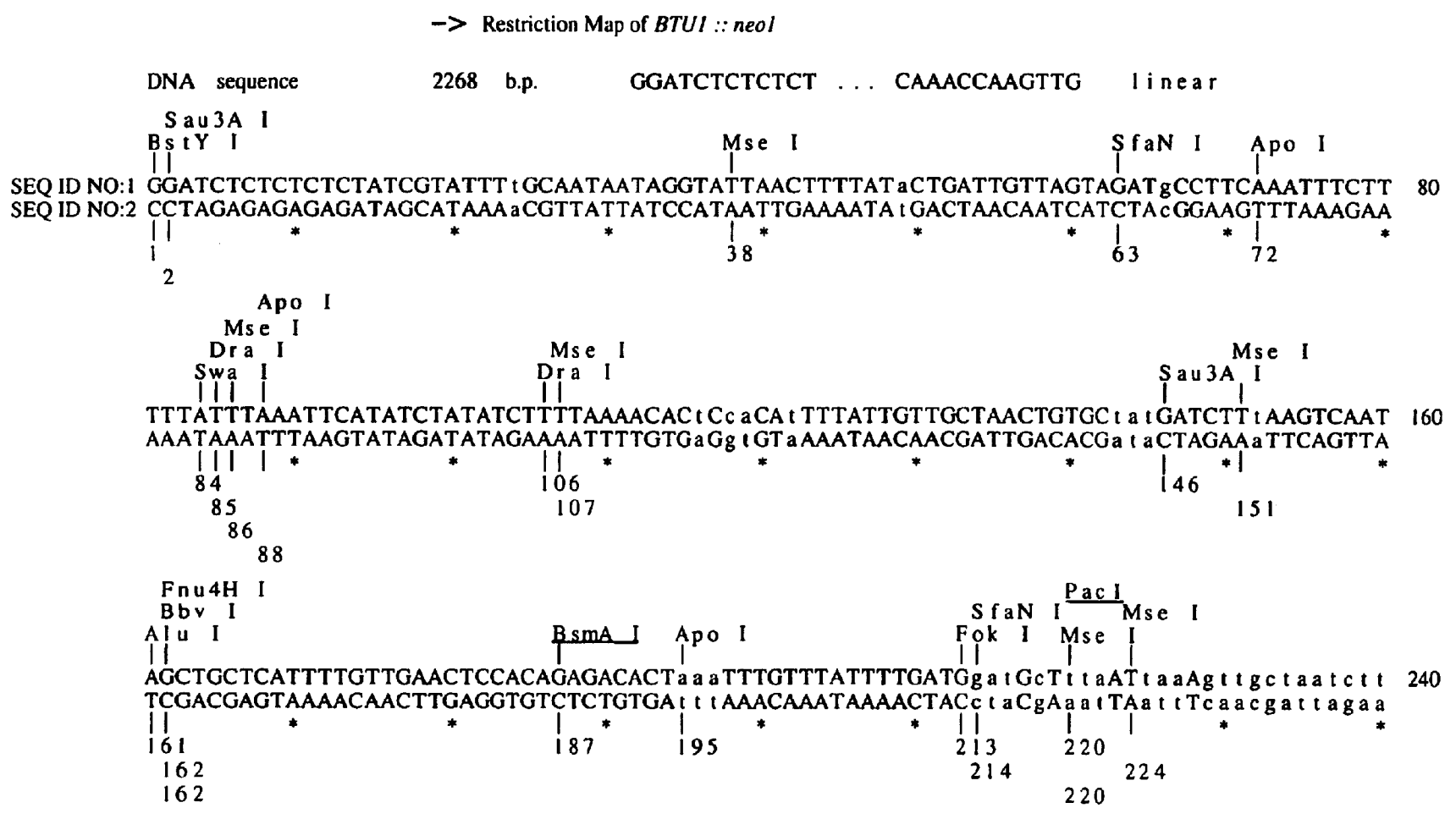
Figure 2A:
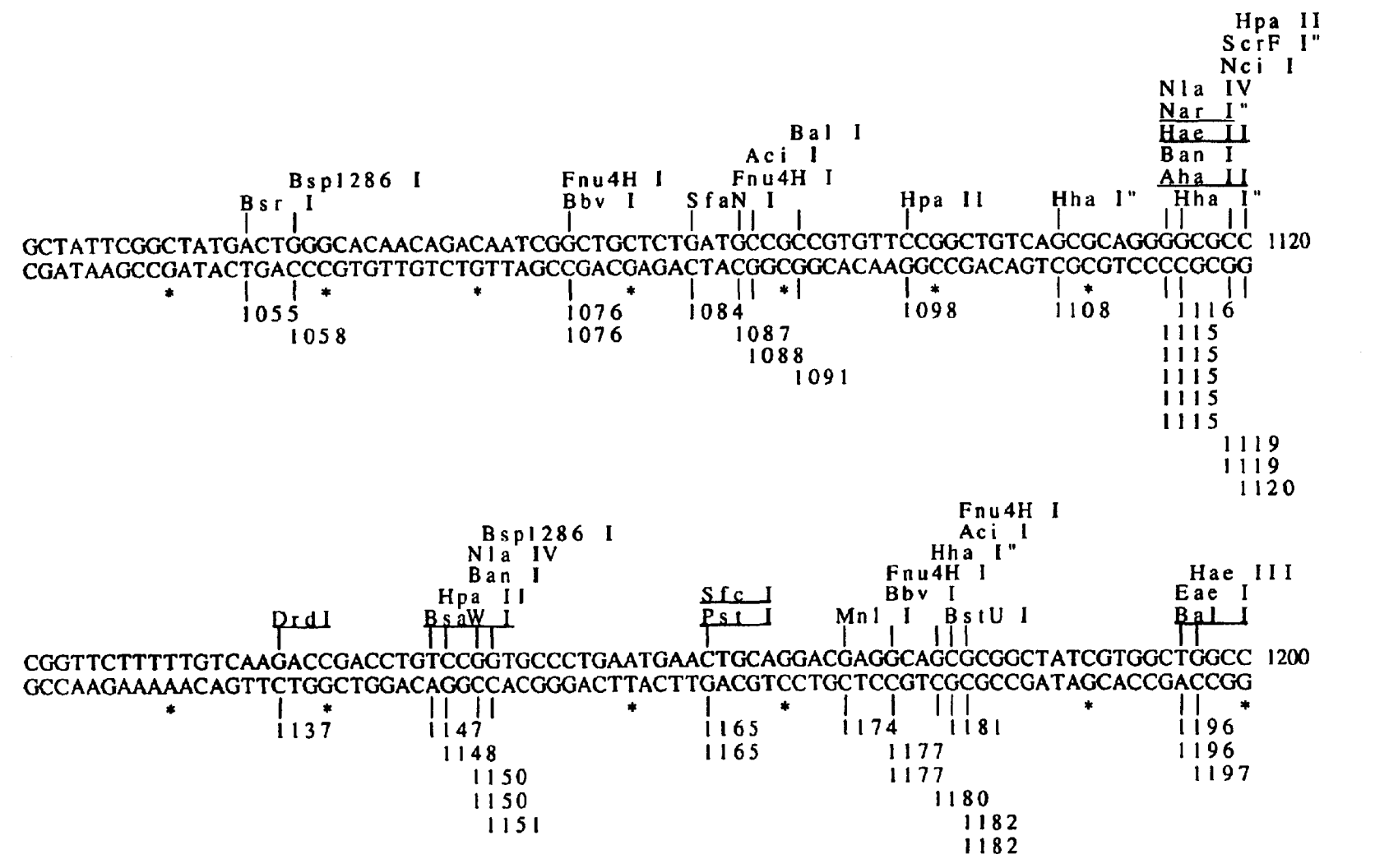
Figure 2A:
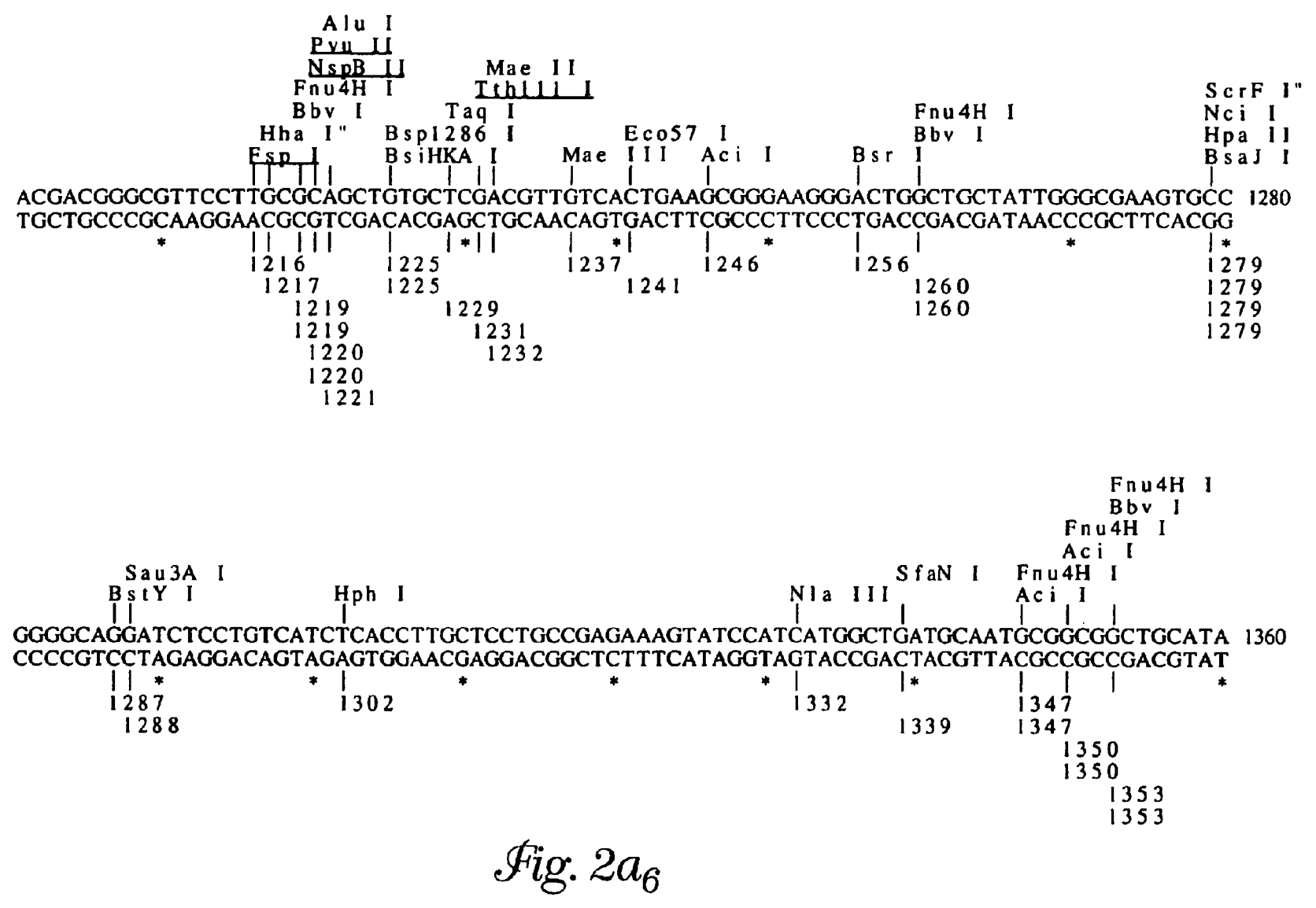
Figure 2B:
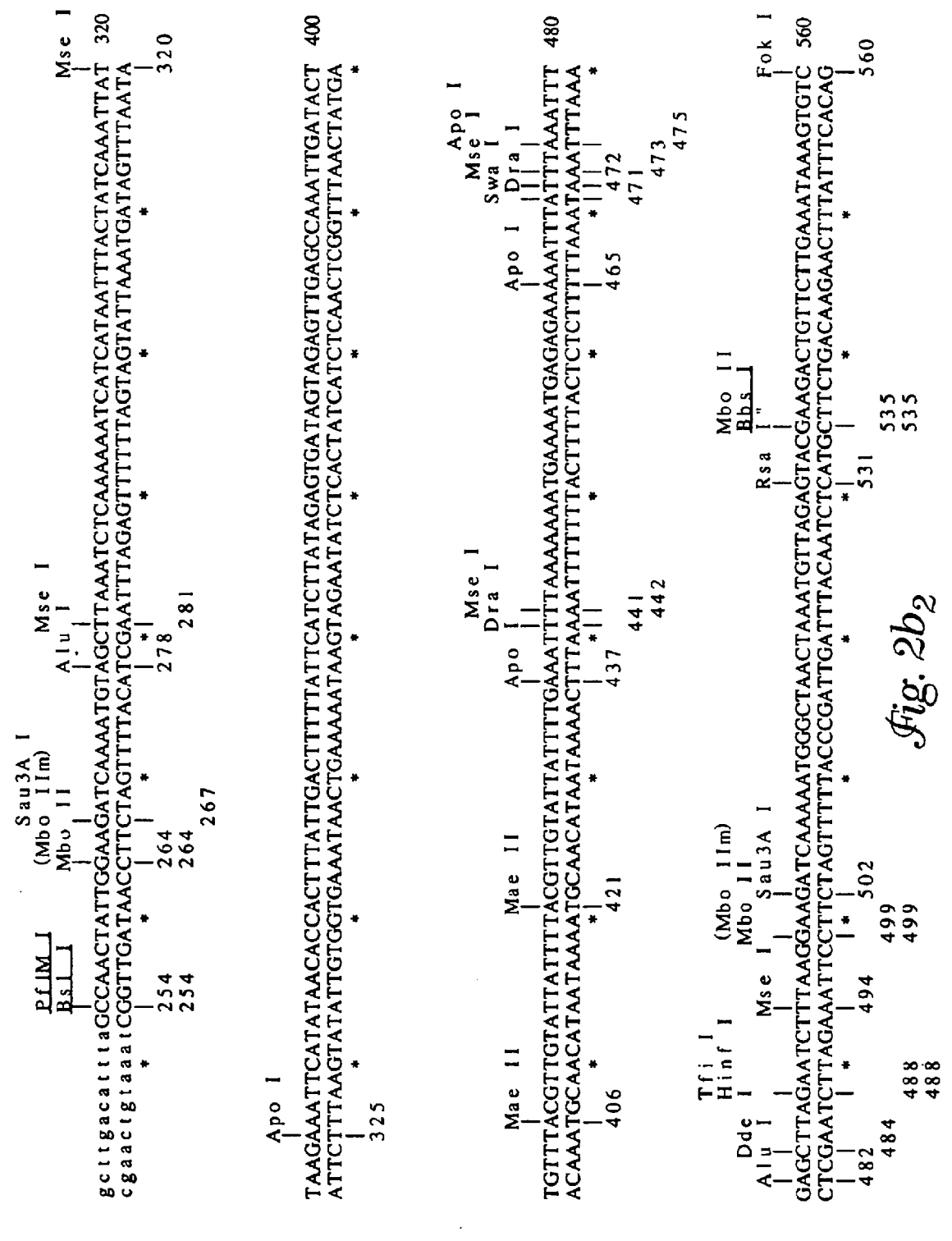
Figure 2B:
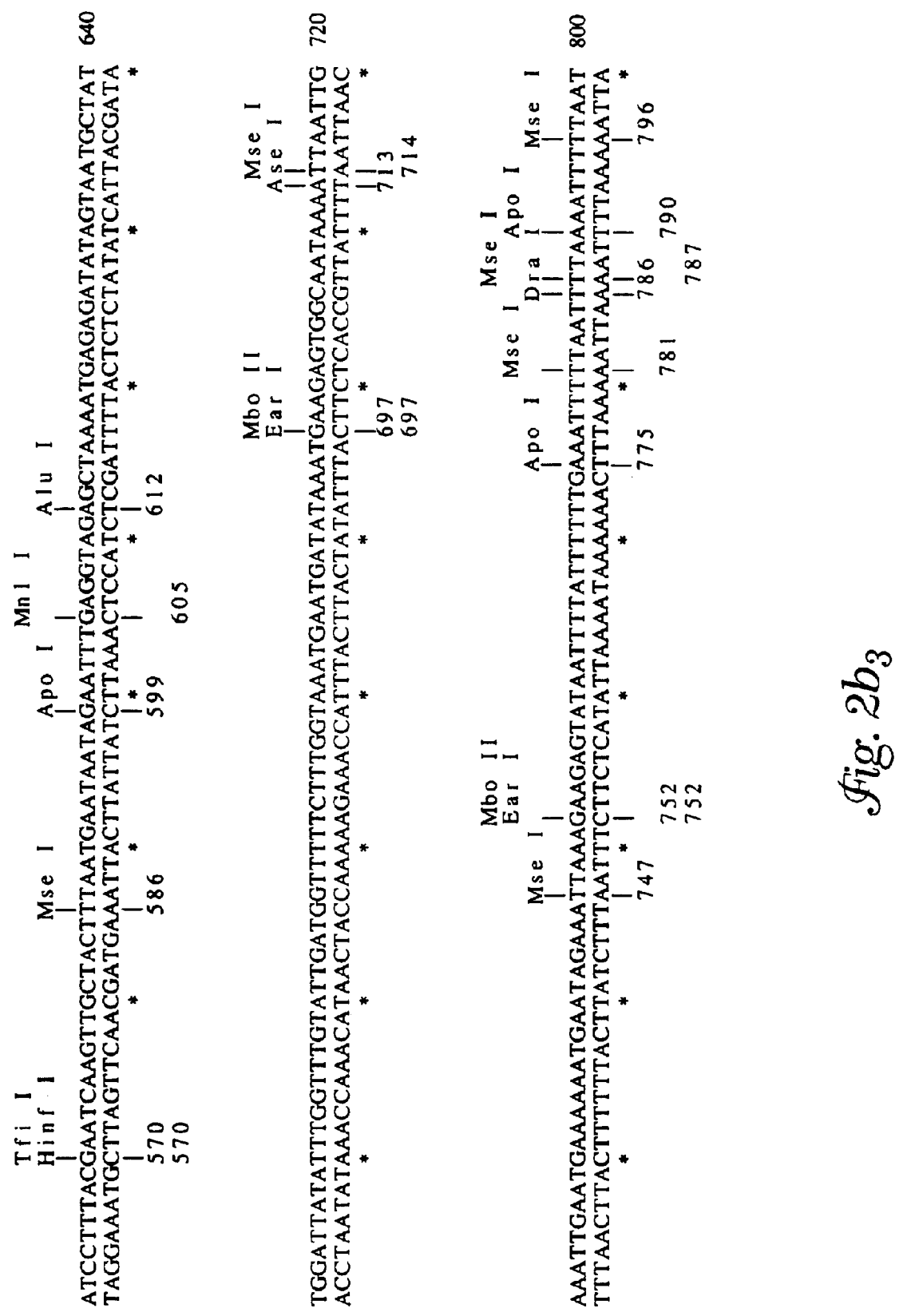
Figure 2B:
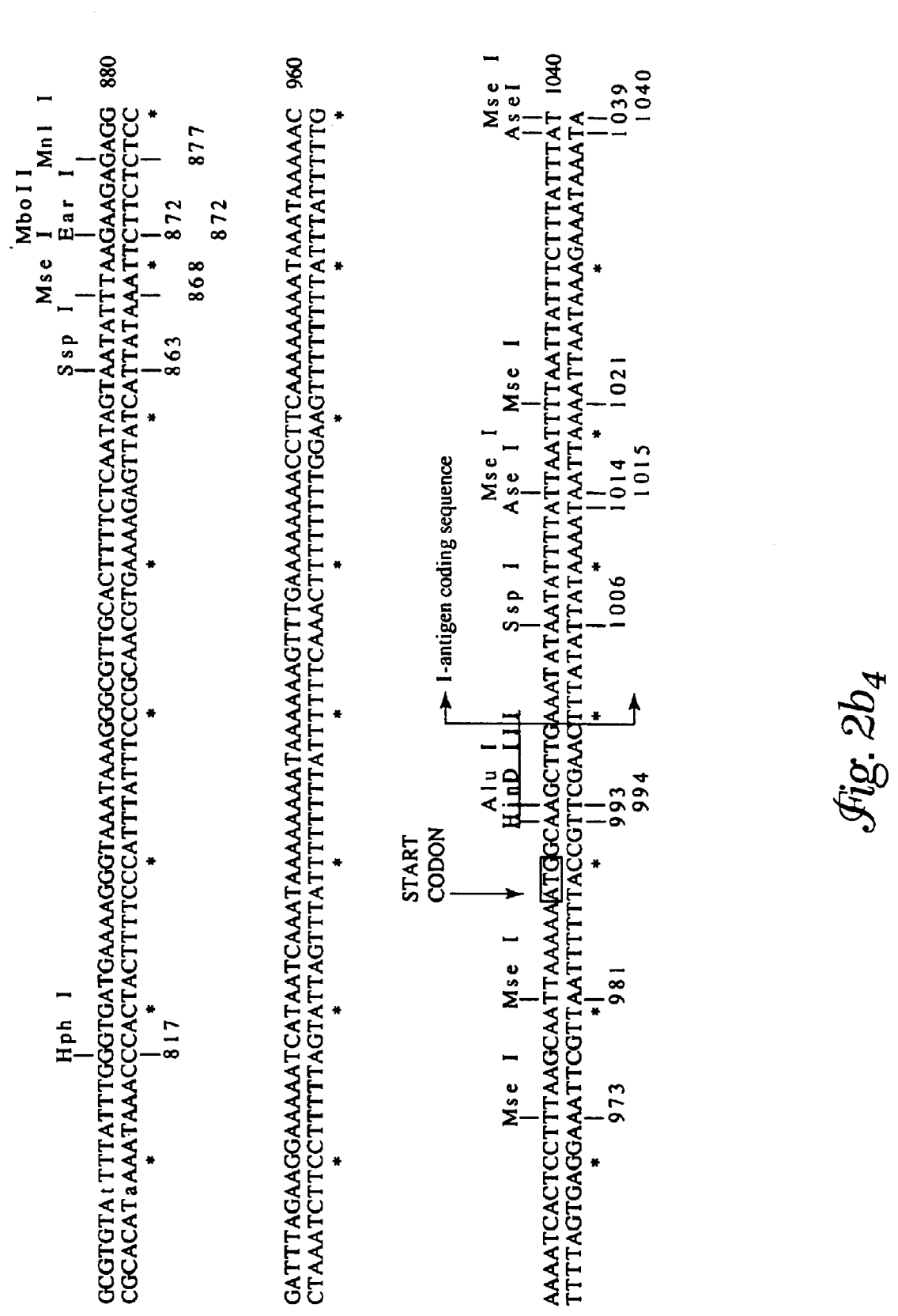
Figure 2B:
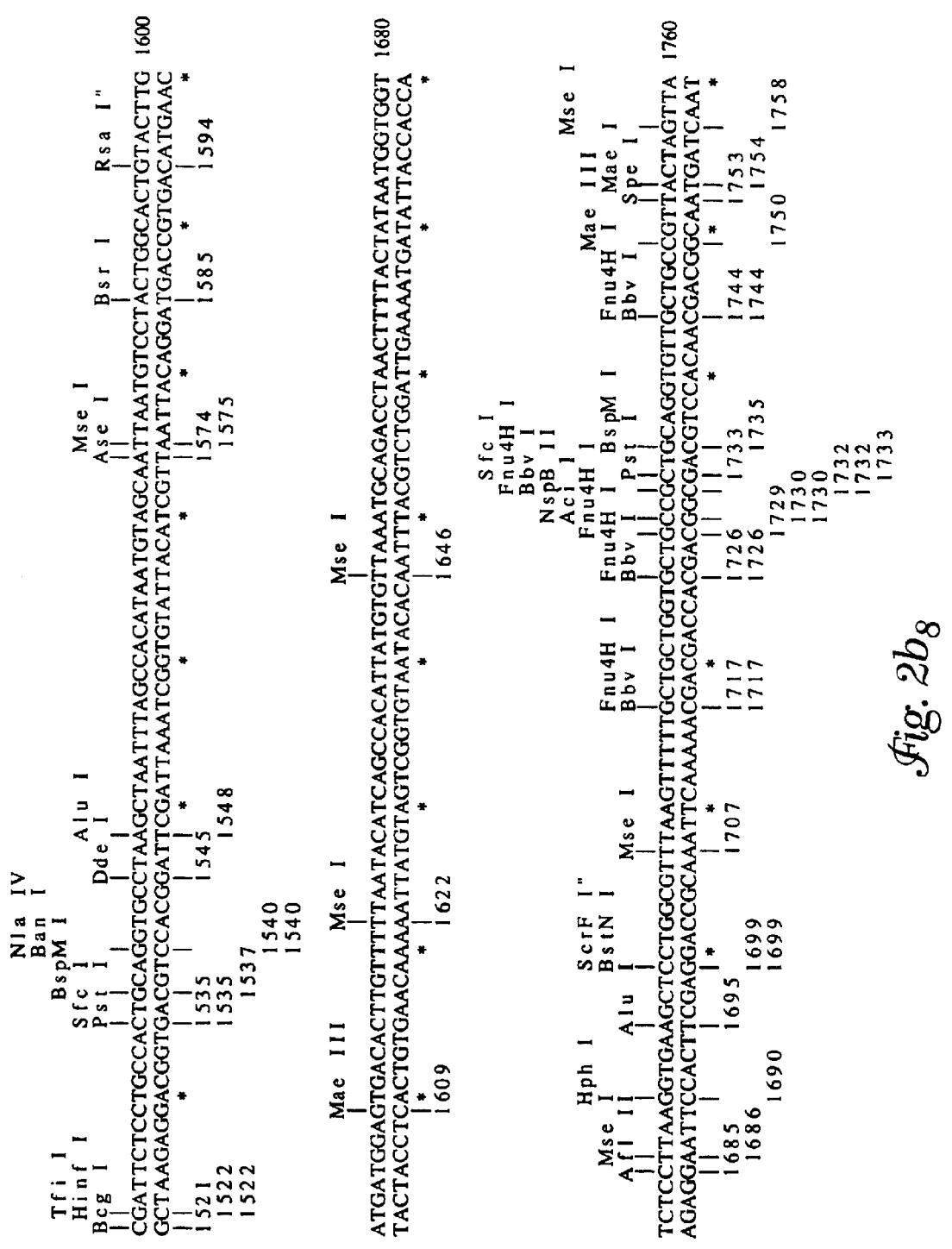
Figure 3B:
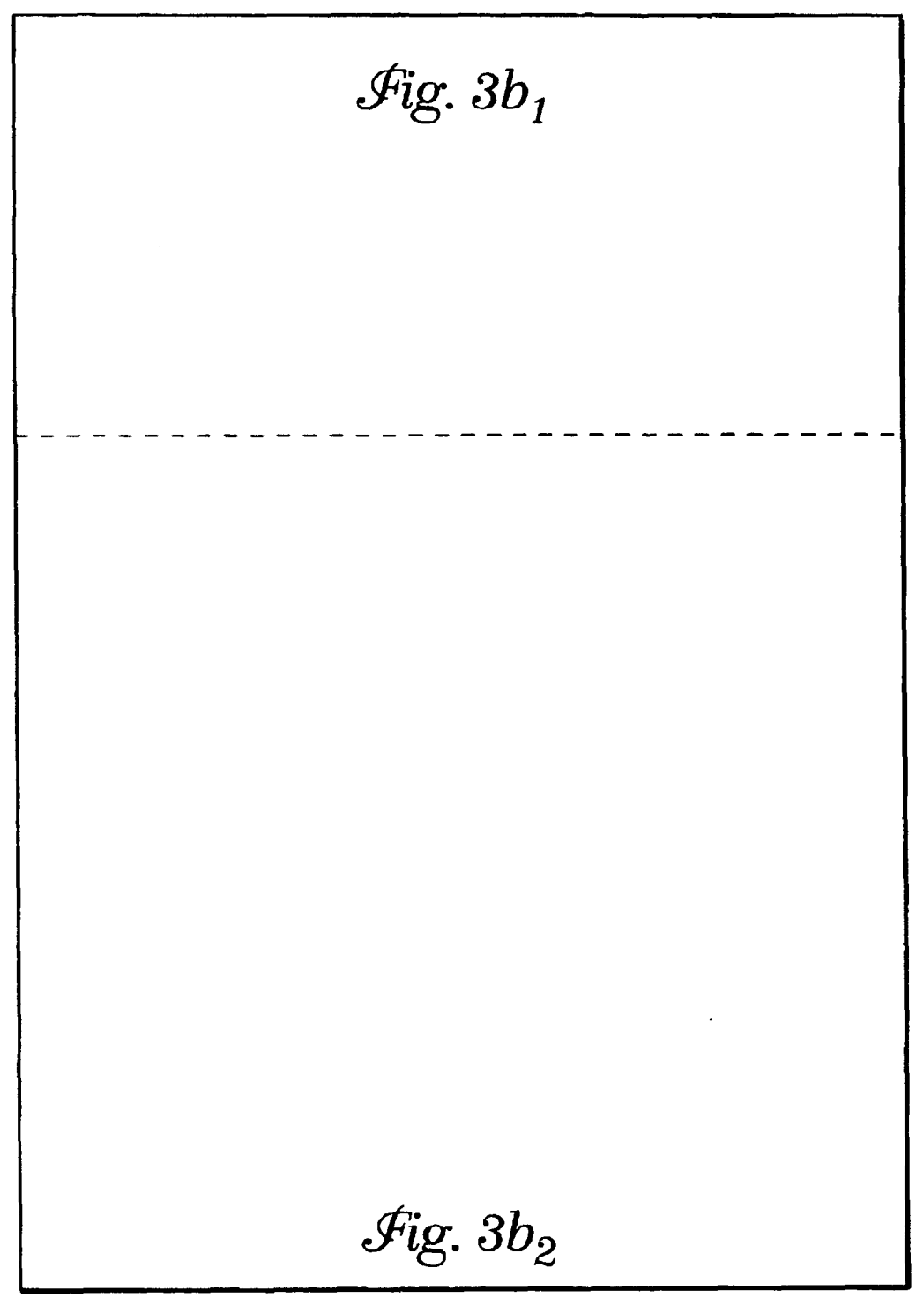

FIG. 2(b) shows the full restriction map of pBICH3, represented by SEQ ID NOs:3 and 4. The complete nucleic acid sequence (SEQ ID NO:7) and deduced amino acid sequence (SEQ ID NO:5) of the DNA encoding the 48 kD Ich i-antigen is presented in FIG. 3. Nucleic acid sequence SEQ ID NO:7 of FIG. 3(b) is included in pBICH3 at base pair 1000 to base pair 2325 as shown in FIG. 2(b). The fragment GCAAGCTTG at base pair 991 to 999, which follows the start codon ATG and immediately precedes the i-antigen coding sequence, is a cloning residual from the parent construct, HHF1::neo (R. Kahn et al., Proc. Nat'l. Acad. Sci. USA 90:9295–9299 (1993)). The resulting vector construct can be propagated in E. coli as a shuttle vector as well.

Gene regulatory elements useful in such transformation systems include both upstream (5') and downstream (3') regulatory elements. For example, in prokaryotic and eukaryotic genes, the upstream region contain promoter elements that specify correct initiation of mRNA synthesis. Although classical promoters have not yet been identified in ciliates, examination of the upstream regions of various ciliate genes shows the presence of sequence elements that are highly conserved, and which are known to be required for gene expression in a wide variety of other eucaryotic systems. For example, TATA sequences that play a critical role in transcription initiation in most eukaryotes, are present in the 5' flanking regions of a number of ciliate genes (for example, Cupples et al. (1986) Proc. Natl. Acad. Sci. USA 83:5160–5164; Brunk et al. (1990) Nucl. Acids Res. 18:323–329; Tondravi et al. (1990) Mol. Cell. Biol. 10:6091–6096, Prat et al. (1986) J. Mol. Biol. 189:47–60). Less common eucaryotic promoter elements (consisting of CCAAT sequences) are also present. The upstream regions of ciliate genes contain information that is both necessary and sufficient for promoter function.

Because promoter elements are subject to differential regulation and have profound effects on RNA transcription levels in vivo, different promoters can be used for the expression of the heterologous nucleic acid. These include the promoters from the actin, histone H4 and SerH3 i-antigen genes from Tetrahymena thermophila (Cupples et al. (1986) Proc. Natl. Acad. Sci. USA 83:5160–5164; Brunk et al. (1990) Nucl. Acids Res. 18:323–329; and Tondravi et al. (1990) Mol. Cell. Biol. 10:6091–6096). Expression from the actin promoter is typically constitutive, while expression from the histone and SerH3 promoters are cell-cycle and temperature-dependent, respectively. Expression vectors capable of autonomous replication must include a promoter element; however, when the heterologous nucleic acid is genomically integrated, inclusion of a heterologous promoter element in the construct is optional, as the 5' regulatory region of the endogenous gene can be utilized instead.

The sequences required for correct 3' processing of mRNA transcripts in ciliates (that is, transcription termination and polyadenylation) lie in close proximity to (and approximately 100 bp on either side of) the 3' terminus of most ciliate RNA transcripts. For example, an additional region from the 3' end of the SerH3 i-antigen gene from T. thermophila can be added to the heterologous nucleic acid prior to cloning and expression.

rDNA vectors and rDNA-based vectors, including the typical components of each, were discussed in detail in the background. Although not preferred embodiments of the invention, these vectors can nevertheless be effectively used to express heterologous proteins in Tetrahymena. Depending upon the vector design, rDNA vectors and rDNA-based vectors can integrate into the host genome, for example via homologous recombination or a single cross-over event, or they can be maintained extrachromosomally. Either type of vector can be constructed to include a heterologous protein containing an N-terminal targeting sequence, a C-terminal targeting sequence (i.e., a GPI anchor) or both, for targeted expression of a heterologous protein in Tetrahymena and other ciliates. Preferably, the N-terminal targeting sequence and/or the C-terminal targeting sequence is derived from an i-antigen of *I. multifiliis*.

Targeted Protein Production

Advantageously, the invention allows the recombinant production of a heterologous polypeptide to be targeted within or outside of a cell. The targeting mechanism is not limited to protozoan hosts but can be used in any type of cell, for example a mammalian cell, a yeast cell, a protozoan cell, or a bacterial cell. Preferably, however, the cell is a cell of a ciliated protozoan. Optionally, therefore, a recombinant genetic construct of the invention (i.e., expression vector or transgenic organism) contains a heterologous nucleic acid that encodes a protein comprising an N-terminal protein targeting sequence or a C-terminal protein targeting sequence, or both. An N-terminal targeting sequence directs a protein to the endoplasmic recticulum (ER), and as a result can cause the protein to embed in the plasma membrane or to be secreted out of the cell. A C-terminal targeting sequence, specifically a GPI anchor, can cause the protein to be displayed on the membrane surface of the host cell. These targeting sequences can be either endogenous to the host cell, as where the heterologous nucleic acid is introduced into the host's genome by way of homologous recombination with a native coding sequence, or heterologous to the host cell.

Thus, to direct a heterologous polypeptide to the plasma membrane surface ("surface display"), the vector construct preferably encodes a heterologous polypeptide comprising (1) an amino terminal signal peptide and (2) a GPI cleavage/attachment sequence (i.e., a "GPI anchor"). The expression system of the invention is thus uniquely suited for expression of membrane proteins such as receptor proteins or proteins that utilize a GPI anchor. In other applications in which secretion of a heterologous polypeptide is intended, the vector construct preferably encodes a heterologous polypeptide comprising an amino terminal signal peptide but not a GPI cleavage/attachment sequence. Finally, for intracellular production of the heterologous polypeptide, the heterologous polypeptide encoded by the vector construct preferably includes neither an amino terminal signal peptide nor a GPI cleavage/attachment sequence.

Surprisingly, surface display of heterologous proteins in Tetrahymena is not limited to the use of a GPI anchor modification domain that is native to Tetrahymena. It has been discovered, for example, that proteins that contain a GPI anchor derived from an immobilization antigen ("i-antigen") of *Ichthyophthirius multifiliis* are displayed on the membrane surface of Tetrahymena (Example II). Likewise, it is not necessary to use N-terminal signal peptides derived from Tetrahymena; it is shown in Example VI that the N-terminal signal peptides of both *I. multifiliis* i-antigen and *T. cruzi* gp-72 protein work well in Tetrahymena.

Thus, protein targeting sequences can be derived, for example, from *I. multifiliis, T. cruzi*, Paramecium, Dictyostelium, Leishmania, Toxoplasma, Crithidia, Plasmodium and Chlamydomonas. An example of an N-terminal protein targeting sequence from *T. cruzi* is the N-terminal signal peptide of the gp-72 surface protein. Heterologous protein targeting sequence obtained from *I. multifiliis* are described in T. Clark et al., *Proc. Nat. Acad. Sci. USA*, 89:6363–6367 (1992) and T. Clark et al., *Gene* 229:91–100 (1999); additional exemplary N-terminal and C-terminal targeting sequences, derived from the 48 kD and 55 kD *I. multifiliis* i-antigens (SEQ ID NOs:5 and 6, FIG. 3(a)), are described in provisional U.S. patent application Ser. No. 60/124,905, filed Mar. 17, 1999. The coding sequence of an *I. multifiliis* i-antigen includes two putative signal elements. For example, the N-terminal portions (i.e., about the first 20 amino acids) of the 48 kD i-antigen (SEQ ID NO:5, FIG. 3(a)) and the 55 kD i-antigen (SEQ ID NO:6, FIG. 3(a)) form highly hydrophobic domains which are similar to the signal peptides required in other organisms for translocation of newly translated polypeptides into the endoplasmic reticulum (ER). The C-terminal portions (i.e., about the last 20 to 23 amino acids) of the 48 kD i-antigen (SEQ ID NO:5, FIG. 3(a)) and the 55 kD i-antigen (SEQ ID NO:6, FIG. 3(a)) contain sequences that are homologous to the signals required for addition of a glycosylphosphatidylinositol (GPI) anchor and membrane anchoring of surface-displayed polypeptides. Surprisingly, the targeting signals of the *I. multifiliis* 48 kD i-antigen have been discovered according to the invention to be fully functional in Tetrahymena, causing surface display on the Tetrahymena plasma membrane of the i-antigen of *I. multifiliis*. Heterologous fusion proteins comprising one or both of these *I. multifiliis* signal sequences are therefore fully expected to be targeted correctly in Tetrahymena. For example, the targeting sequences of the *I. multifiliis* i-antigen can be used for surface display in Tetrahymena of heterologous surface membrane proteins such as surface antigens or receptors. Moreover, these targeting sequences are also expected to allow surface display or secretion of a polypeptide that is not normally expressed on a cell surface. For example, the protein expression system of the invention can be used for surface display of proteins that may be toxic to the cell when expressed intracellularly, such as proteases that can degrade Tetrahymena's own essential cytosolic proteins.

It should be understood that this aspect of the invention involving protein targeting using, for example, N-terminal and C-terminal targeting sequences from *I. multifiliis* and other protozoa applies not just to protein targeting in protozoa but in other cells such as bacterial cells, fungus cells and animal cells including vertebrate cells such as mammalian cells.

Further, other types of targeting sequences are well-known and can be used in the practice of the invention. For example, targeting to the surface of a ciliate can also be achieved if the protein includes a known transmembrane domain, such as the C-terminal 80 amino acids of human membrane cofactor, in place of a GPI anchor (see e.g., J. Seeber et al., *J. Cell Sci.*, 111:23–29 (1998)). In this embodiment, the protein can be partially embedded in the membrane and partially exposed on the outside of the cell.

It should also be understood that recombinant genetic constructs of the invention encode proteins that preferably do, but need not, contain N-terminal and/or C-terminal targeting sequences; a protein without such signaling sequences will simply remain in the cytosol of the host cell.

Cell Surface Expression of Antigens

The ability to express polypeptides on a protein surface, in particular, gives this system advantages over others known in the art for many purposes. For example, antigens, including haptens, can be expressed on the cell surface as fusion proteins, cleaved, isolated, and injected into laboratory animals to generate antibodies for further use. Alternatively, antigens expressed on the surface of a host cell can be used to identify antibodies directly using a in vitro immobilization reaction or chemokinesis of swimming cells. Antisera directed against the i-antigens of hymenostomatid ciliates (including Paramecium, Tetrahymena and Ichthyophthirius spp.) cross-link cilia and cause rapid immobilization of corresponding cell types in culture (J. Preer, "Surface Antigens of Paramecium" in J. Gall, ed., *Molecular Biology of Ciliated Protozoa*, Academic Press, London, 301–339 (1986); F. Caron et al., *Ann. Rev. Microbiol.* 43:23–42 (1989); Clark et al., *Ann. Rev. Fish Dis.* 5:113–131 (1995)). For example, an immobilization assay can be conducted on the transgenic cells to detect antibody in serum samples of a parasite-infected patient. A positive reaction is detected by immobilization of the live transgenic protozoan cells, due to cross-linking of antibodies bound to surface-displayed parasitic proteins. This method can be extended to detect serum antibodies to other bacterial, parasitic, or fungal infections or diseases, using a live transgenic protozoan genetically engineered in accordance with the invention to display the appropriate antigen on its surface. Likewise transgenic cells of the invention that display antigens on their surface can be used to isolate and purify antibodies. Screening of chemical agents (drugs) for the ability to bind to polypeptides, and purification of drugs thus identified, can also be readily accomplished using the invention, as long as the candidate drugs possess cross-linking capability. Cross-linking capabilities include the provision of multiple potential binding sites on the candidate drugs, or the addition of chemical or radiation-dependent cross-linking sites on the candidate drugs. In the latter case, cross-linking is initiated after binding of the drug to the live ciliate, and the mechanism for cross-linking must be selected such that it does not itself cause immobilization of the transgenic ciliate. For example, the protein expression system could be used for screening multivalent ligands that bind to human neurotransmitter receptors expressed on the surface of transgenic Tetrahymena according to the invention.

Preparative Protein Production

The invention includes a method for producing a polypeptide that involves introducing into a ciliated protozoan host an expression vector containing a heterologous nucleotide sequence encoding a polypeptide, then expressing the polypeptide. After the vector is introduced into the ciliate host, the host is cultured under conditions that allow expression of the coding region such that the polypeptide encoded by the coding region is produced. The polypeptide can be present within the host cell, secreted from the host cell or is anchored to the surface of the host cell. Optionally, the method further includes isolating the polypeptide. The amino acid sequence of the heterologous polypeptide encoded by the coding region of the vector used to transform the ciliate host optionally includes protein targeting sequences. The polypeptide produced by the transformed host preferably includes either an amino terminal signal peptide or a GPI cleavage/attachment site or both. More preferably, the polypeptide includes both an amino terminal signal peptide and a GPI cleavage/attachment site.

Transgenic Ciliate

The present invention also provides a ciliated protozoan, preferably a nonpathogenic ciliated protozoan, more preferably Tetrahymena, that has been genetically engineered to express a heterologous polypeptide, preferably on its cell surface. A surface-expressed heterologous protein is attached by way of a "GPI anchor" that is encoded by a GPI cleavage/attachment sequence. Preferably, the ciliate contains a vector containing a coding region that encodes the heterologous protein, wherein the coding region is integrated into the BTU1 gene of *T. thermophila*.

Live and Killed Vaccines

Success in expressing polypeptides on the surface of a ciliated protozoan has immediate implications for vaccine development. Surface antigens are important targets of the humoral immune response against a wide range of microbial pathogens. Accordingly, the present invention provides a system for vaccination that makes use of surface expression of heterologous antigenic polypeptides encoded by heterologous nucleic acid fragments in a ciliated protozoan.

A vaccine effective for the prevention of infection in an organism is one that elicits the production of a protective immune response in an organism exposed to the vaccine. The immune response can be a cellular response and/or involve the production of antibodies. The goal of vaccination is to elicit a population of lymphocytes, which upon subsequent exposure to the disease causing agent, such as a parasite, proliferate and produce antibodies and/or effector cells specific to the parasite, resulting in protection against lethal infections.

The vaccine of the invention can be either a live vaccine or a killed vaccine. It is useful to prevent disease in vertebrates, including humans, dogs, cats, reptiles, poultry, cattle, swine and fish. Preferably, the vaccine of the invention is effective to prevent disease in fish, more preferably it is effective to prevent parasitic infection in fish. The vaccine preferably comprises a live or killed host ciliated protozoan having, attached to its plasma membrane and displayed on it surface, a heterologous antigenic polypeptide. The heterologous protein is preferably GPI-anchored to the plasma membrane. In a particularly preferred embodiment of the vaccine, the heterologous antigenic polypeptide that is surface expressed comprises all or an immunogenic portion of an immobilization antigen ("i-antigen") of a pathogenic ciliated protozoan. I-antigens are surface protein that are generally abundant on the surface of a ciliate; an antibody that is specific for an i-antigen causes a loss of protozoan motility, and can cause agglutination of the cilia. Use of a whole cell vaccine, whether live or killed, has the additional advantage of potentially serving as an adjuvant, thus further stimulating the immune system of the recipient.

White spot disease, also called "Ich," is a disease caused by the parasite *I. multifiliis*, a holotrichous ciliated protozoan which is an obligate parasite of freshwater fish. Under conditions of intensive aquaculture, Ich frequently has a high morbidity and mortality, resulting in significant financial losses to fish producers. Attempts to control or prevent *I. multifiliis* infections have met with only limited success. Killed *I. multifiliis* cells and *I. multifiliis* cilia alone do not elicit protective immunity. Nor has vaccination of fish with the cells or cilia of other ciliates, such as *T. thermophila* cells or cilia, generated protective immunity against Ich infection (Gratzek et al., U.S. Pat. No. 4,309,416). Chemical treatments are likewise unsatisfactory because carcinogenicity and/or toxicity are typically associated with these therapeutic agents. See Burkart et al., *J. Fish Dis.*, 13:401–410 (1990), for a summary. Moreover, *I. multifiliis* can only be grown in association with its host, and efforts to produce i-antigens in conventional protein expression systems are inconvenient at best.

Significantly, Tetrahymena is nonpathogenic and is normally present in freshwater ecosystems. It thus represents an ideal vehicle for vaccination against *I. multifiliis* infection and other fish diseases. The use of *T. thermophila* for the expression and delivery of the antigens will make possible large-scale, cost-effective fish vaccination programs.

A vaccine against *I. multifiliis* infection preferably comprises live or killed *T. thermophila* that have been engineered according to the invention to express all or an immunogenic portion of an i-antigen from *I. multifiliis* on its surface. Preferably, the i-antigen used in the live or killed *T. thermophila* vaccine of the invention is encoded by i-antigen encoding sequences of either IAG48[G1] or IAG55[G5] (FIG. 3(*b*)). In a particularly preferred embodiment, the vaccine comprises transgenic *T. thermophila* wherein expression of the *I. multifiliis* i-antigen is achieved by insertion of the i-antigen into the endogenous btu1-1K350M locus. Because this transformant can be maintained by negative selection, a selectable drug-resistance gene does not need to be introduced into the transgenic host, eliminating the possible introduction of antimicrobial resistance genes into the environment upon release of transgenic Tetrahymena.

In the ciliated protozoan genetic code, TAA and TAG encode glutamine, whereas they serve as stop codons in the "universal" genetic code. The presence of glutamine-encoding TAA and TAG codons in the native coding sequence of the i-antigen creates barriers to expression of this sequence in conventional bacterial gene expression systems. Advantageously, *T. thermophila* recognizes UAA and UAG codons as glutamine codons as does *I. multifiliis*. In addition, post-translational modifications, particularly glycosylation, are expected to occur more normally in organisms related to Ichthyophthirius (for example, Tetrahymena) than in prokaryotes such as *E. coli*, or more distantly related eukaryotes. Because such modifications can play a critical role in immune recognition, Tetrahymena is particularly advantageous in accordance with the present invention.

As shown in the following Examples describing the surface localization of Ichthyophthirius proteins in Tetrahymena IAG48[G1] transformants, the N-terminal and C-terminal protein targeting peptides associated with *I. multifiliis* i-antigen function appropriately in Tetrahymena, i.e., the antigenic protein is expressed on the surface of transgenic Tetrahymena. Moreover, the overall distribution of *I. multifiliis* antigens in transformed Tetrahymena cells bear a striking resemblance to the pattern seen in the parasite itself where they are found in ciliary and plasma membrane, and in the cell cortex in association with secretory mucocysts.

The invention further includes a method for vaccinating an animal that includes contacting the animal with a genetically engineered nonpathogenic ciliated protozoan, preferably Tetrahymena, so as to elicit a protective immune response in the animal to the heterologous antigen displayed on the surface of the protozoan host. For example, an animal can be exposed to an ingestable composition, such as food, water, or both, that contains an immunogenic genetically engineered nonpathogenic ciliate of the invention. Alternatively, an animal can be immersed in or sprayed with an aqueous solution that includes the immunogenic ciliate. For example, fish can be vaccinated in accordance with the invention by exposing the fish to a composition including transgenic *T. thermophila* expressing an antigenic polypeptide (e.g., the *I. multifiliis* i-antigen to vaccinate against white spot disease). The fish can be immersed in an aqueous solution comprising transgenic *T. thermophila* expressing the *I. multifiliis* i-antigen. Because the antigenic proteins are presented to the immune system, probably through the lateral line and gills, the fish can begin to produce protective antibodies to at least a portion of the *I. multifiliis* i-antigen.

The vaccine can also be administered by injecting the animal with live or killed genetically engineered nonpathogenic immunogenic ciliated protozoa, by injecting the animal with a purified or partially purified membrane fraction of cells of the genetically engineered nonpathogenic immunogenic ciliated protozoa, or by injecting the animal with cilia from cells of the genetically engineered nonpathogenic immunogenic ciliated protozoa. Additionally, genetically engineered protozoa that display an antigen on the surface according to the present invention can also be used to generate monoclonal antibodies directed to the surface-expressed polypeptide.

EXAMPLES

The following examples are provided for illustrative purposes only and are not intended to limit the scope of the invention.

The examples utilize many techniques well-known and accessible to those skilled in the arts of molecular biology, and in the transformation of Tetrahymena. Enzymes are obtained from commercial sources and are used according to the vendors' recommendations or other variations known in the art. Reagents, buffers and culture conditions are also known to the art. References containing standard molecular biological procedures include Sambrook et al. (1989) *Molecular Cloning*, Second Edition, Cold Spring Harbor Laboratory Press, Cold Spring Harbor, N.Y.; Wu (ed.) (1979) Methods Enzymol. 68; Wu et al. (eds.) (1983) Methods Enzymol. 100 and 101; Grossman and Moldave (eds.) (1980) Methods Enzymol. 65; Miller (ed.) (1972) *Experiments in Molecular Genetics*, Cold Spring Harbor Laboratory, Cold Spring Harbor, N.Y.; Old and Primrose (1981); *Principles of Gene Manipulation*, University of California Press, Berkeley, Calif.; Schlief and Wensink (1981) *Practical Methods in Molecular Biology*; Glover (ed.) (1985) "DNA Cloning", Vols. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York, which are expressly incorporated by reference herein.

References containing molecular biological techniques, procedures and protocols that are particularly useful in ciliated protozoa include J. Boothroyd et al. (eds.) *Molecular Approaches to Parasitology*, John Wiley & Sons, New York and J. Gall (ed.) (1986) *The Molecular Biology of Ciliated Protozoa*, Academic Press, Inc., Orlando, Fla., both of which are also expressly incorporated by reference herein.

Abbreviations and nomenclature, where employed, are deemed standard in the field and commonly used in professional journals such as those cited herein.

Example I

Plasmid Construction: pBAB1 and pICH3

The pBTU1 plasmid containing a 3.7 kb BglII/HindIII fragment of the *Tetrahymena thermophila* β-tubulin gene, BTU1, was used to construct a derivative, pBAB1, in which the entire coding sequence was replaced with the coding sequence of the neomycin resistance gene, noe1 (R. Kahn et al., *Proc. Nat'l. Acad. Sci. USA* 90:9295–9299 (1993)). Thus, the expression of noe1 gene on pBAB1 is driven by the flanking sequences of the BTU1 gene. The plasmid pBAB1 was used to construct another derivative in which the neo coding region was replaced with the entire coding sequence of the Ichthyophthirius i-antigen (isolate G1) pre-protein. T. G. Clark et al., *Proc. Natl. Acad. Sci. USA*, 89: 6363–6367 (1992). To this end, the pBAB1 plasmid was amplified with the NEO257 primer (5'-

AGCCAGTCCCTTCCCGCTTCAGTGACAA-3' (SEQ ID NO:9) (provided by J. Bowen and M. Gorovsky, University of Rochester, N.Y.) whose sequence encodes the antisense strand of the noe1 gene, and primer BTN3 (5'-CGGGATCCAGCGAACTGAATCGGTCAGCT-3') (SEQ ID NO:10), corresponding to the 3' noncoding region of BTU1 located immediately downstream from the stop codon, TGA, and running in the same direction as the sense coding strand. The BTN3 primer contains a BamHI restriction site sequence at its 5' end, positioned immediately downstream from the stop codon, TGA. The product of PCR amplification of pBAB1 using NEO257 and BTN3 primers contained the noncoding sequences of BTU1, an N-terminal half of the noe1 gene coding region and the vector sequence. A single HindIII site is located almost immediately downstream from the translation initiation codon, ATG, of the noe1 gene. The amplified product was digested with BamHI and HindIII to obtain a smaller fragment containing the entire flanking sequences of BTU1 and the plasmid vector. A plasmid carrying a 2 kb EcoRI genomic fragment of the Ichthyophthirius i-antigen gene was amplified with primers IC5 (5° CCCAGCTTGAAATATAATATTTTATTAATTTTAATT-3') (SEQ ID NO:11) and IC3 (5'-AGGGATCCTCACAATAAATAGAAAGAAATAA3') (SEQ ID NO:12). These primers amplified the entire coding sequence of the Ich i-antigen gene and introduced HindIII, and BamHI restriction sites at positions encoding the N-terminal and C-terminal end of the protein respectively and corresponding to the positions of the same restriction sites present on the amplified fragment of pBAB1. This PCR product was digested with HindIII and BamHI, and ligated to the BamHI-HindIII digest of amplified pBAB1 to give pBICH3 plasmid, which contains the entire coding sequence of the i-antigen gene inserted in a correct translational frame between the regulatory sequences of the BTU1 gene (see FIG. 1). This new hybrid gene was designated BTU1-4::IAG48[G1].

Example II

DNA-mediated Transformation of *T. thermophila*

Transformation

A *Tetrahymena thermophila* strain, CU522 (provided by Dr. Peter Bruns, Cornell University, Ithaca N.Y.) was used as a transformation host. This strain carries a single substitution (K350M) in the β-tubulin, BTU1 gene. This mutation was originally described for *Chlamydomonas reinhardtii* (Bolduc et al., Proc. Nat'l. Acad. Sci. USA 85:131–135 (1988)), and was later found to confer a similar phenotype in *T. thermophila*, namely, increased resistance to several microtubule depolymerizing drugs, such as oryzalin and colchicine, and increased sensitivity to a microtubule stabilizing agent, paclitaxel (J. Gaertig et al., Proc. Nat'l. Acad. Sci. USA 91:4549–4553 (1994)).

Cells were grown in 50 ml of SPP medium (J. Gaertig, *Proc. Nat'l. Acad. Sci. USA*, 91:4549–4553 (1994)), supplemented with 100 U/ml penicillin, 100 μg/ml streptomycin and 0.25 μg/ml amphotericin B (SPPA medium), in 250 ml Erlenmayer flasks with shaking at 150 rpm at 30° C. Prior to transformation, the CU522 cells were grown to a density of about $6 \times 10^5$ cells/ml in SPPA with shaking at 30° C. Twenty-four hrs before transformation, 50 ml of growing cells were washed and suspended in 10 mM Tris-HCl (pH 7.5) buffer in the original volume. After 4–5 hrs starving cells were counted again, cell concentration adjusted to $3 \times 10^5$ cells/ml and cells left at 30° C. without shaking for another 18–20 hrs.

To target the BTU1 gene derivatives to the endogenous BTU1 locus of *T. thermophila*, either pBAB1 or pBICH3 plasmids were digested with SacI and SalI restriction endonucleases to separate the insert (either BTU1-2::noe1 or BTU1-4::IAG48[G1]) from the plasmid. Fifty micrograms of digested DNA was purified by a single phenol/chloroform/isoamyl alcohol (25:24:1) extraction followed by chloroform/isoamyl alcohol (24:1) extraction, precipitated with an equal volume of isopropyl alcohol in the presence of 0.15 M sodium acetate, dried and resuspended at 1 mg/ml.

The transformation method used in this study targets genes into the somatic macronucleus of vegetative cells using biolistic bombardment (D. Cassidy-Hanley et al., *Genetics* 146:135–147 (1997)). Ten micrograms of linearized plasmid DNA was used to coat 60 mg of 0.6 μm gold particles (Bio-Rad) using the Sanford Large Batch DNA Coating Method, as described by J. C. Sanford et al., *Technique*, 3:3–16 (1991). An aliquot of $2.4 \times 10^7$ of starved cells was spun down at 600×g for 3 min, washed with 45 ml of 10 mM Tris (pH 7.5) and resuspended in 3 ml of Tris buffer. One ml of cells was bombarded using 10 μg of DNA-coated gold particles at 900 psi using DuPont Biolistic PDS-1000/He particle delivery system (Biorad). Bombarded cells were resuspended in 50 ml of SPPA, left for 2–3 hours at 30° C. Paclitaxel was added to the final concentration of 20 μM and cells were plated on microtiter plates using 100 μl cells per well and plates were incubated in moist boxes at 30° C. (in darkness, to prevent photobreakdown of paclitaxel). Wells containing paclitaxel-resistant transformants were apparent after 2–3 days of selection.

To identify sequences integrated into the BTU1 locus of *T. thermophila*, total genomic DNA was isolated from transformants using the fast urea method as described by J. Gaertig (*Proc. Nat'l. Acad. Sci. USA*, 91:4549–4553 (1994)) and used as a template for PCR with primers: BTU1-75 (5'-AAAAAATAAAAGTTTGAAAAAAA-3') (SEQ ID NO: 13), sequence located 53–75 bp upstream to the ATG translation initiation codon in the BTU1 5' flanking region, and primer BTU1-3, (5'-GTTTAGCTGACCGATTCAGTTCG-3') (SEQ ID NO:14), located close to the TGA stop codon in the 3' flanking region of BTU1. The resulting amplified products were digested with Nsi I restriction endonuclease and run on a TAE-agarose 0.7% gel.

Immunocytochemistry

For immunofluorescent detection of the *I. multifiliis* i-antigen in transgenic Tetrahymena cells, 10 mls of exponentially growing cultures ($2 \times 10^5$ cells/ml) were harvested, washed with 10 mls of 10 mM Tris (pH 7.5) and resuspended in 0.5 ml. Cells were fixed with 3.5 mls of 2% paraformaldehyde in PHEM buffer (60 mM Pipes, 25 mM HEPES, 10 mM EGTA, 2 mM $MgCl_2$, pH. 6.9) for 30 minutes at room temperature. Fixed cells were washed once with 3 mls of PHEM buffer and 2 times with 3 mls of modified phosphate buffered saline, PBS (130 mM NaCl, 2 mM KCl, 8 mM $Na_2HPO_4$, 2 mM $KH_2PO4$, 10 mM EGTA, 2 mM $MgCl_2$, pH. 7.2) and resuspended in 0.5 ml. For antibody labeling, 100 μl of fixed cells were washed 3 times for 10 minutes with 3 mls of PBS-BT, (3% bovine serum albumin, 0.1% Tween 20 in PBS), and concentrated in 100 μl. One μl of affinity-purified rabbit antiserum directed against Ichthyophthirius G1 i-antigen (T. L. Lin et al., *J. Protozool.*, 39:457–463 (1992)), was added, followed by incubation overnight at 4° C., three washes in PBS-BT and incubation with the detection antibodies (at 1:100 dilution) for 45 minutes at room temperature.

Secondary antibodies were goat anti-rabbit IgG coupled to FITC (Zymed). Labeled cells were washed 3 times with PBS, concentrated in 0.1 ml of PBS plus 10 µl of DABCO mounting medium (100 mg/ml 1,4-diazobicyclo-[2,2,2]-octane, Sigma Chemical Co., dissolved in 90% glycerol in PBS). To mount, 5 µl of cells were combined with 5 µl of DABCO medium, covered with a cover-slip and sealed with nail polish. Slides were examined with a Bio-Rad MRC 600 Laser Scanning Confocal Microscope at the UGA Center for Advanced Ultrastructural Research. Sets of optical sections of individual cells were processed to obtain complete 3-D reconstructions.

Immunoblotting

Protein extracts were prepared from 1–2×10$^6$ cells taken from exponentially growing cultures. Cells were spun down at 2000 rpm for 5 minutes, washed with 10 mls of ice-cold 10 mM Tris, pH 7.5, and resuspended in 125 µl of ice-cold Tris buffer supplemented with a mixture of protease inhibitors which included 0.5 µg/ml leupeptin, 10 µg/ml E-64, 10 µg/ml chymostatin and 12.5 µg/ml antipain (A. Turkewitz, personal communication, all inhibitors from Sigma), combined with 125 µl of boiling 2×SDS-PAGE sample buffer and boiled for 5–10 min. Ten µl of extracts were loaded on a 10% SDS-PAGE minigel and proteins transferred on nitrocellulose using semi-dry transfer system (Biorad). The filter was blocked for 2 hr in PBS-T buffer containing 5% dried milk, followed by incubation with the anti-*I. multifiliis* i-antigen antibodies (1:10000) overnight at 4° C. The filter was washed extensively with PBS with 0.1% Tween-20 (PBST) and incubated in the same buffer containing the goat-anti-rabbit IgG antibodies conjugated to alkaline phosphatase (Bio-Rad) for 1 hr at room temperature. The membrane was washed in PBST and developed using NBT/BCIP (Bio-Rad) as described by M. Gorovsky, *J. Protozool.*, 20:19–25 (1973)

Immobilization Assay

Growing Tetrahymena cells were washed with 10 mM Tris, pH 7.5 and resuspended at 2000 cells/ml. Cells were incubated with a series of dilutions of monospecific rabbit polyclonal antiserum against the parasite i-antigen 48 kD protein on microtiter plates at 1000 cells/ml in 100 microliter/well aliquots. After 15–60 minutes wells were scored under a dissecting scope. The behaviors of both BTU1-4::IAG48[G1] transformants and controls (noe1 transformants) were examined, and the percentage of immobilized cells was estimated.

Results

Cells were selected for resistance to either paclitaxel (30 µM) or paromomycin (120 µg/ml). As shown in Table I, transformants were readily obtained following selection with either drug, but were not detected in a mock transformation experiment. Furthermore, random clones that had been selected for growth in paclitaxel were all found to be cross-resistant to paromomycin (n=40), and nearly all transformants originally selected with paromomycin, produced clones resistant to 30 µM paclitaxel (89%, n=71). Thus, acquisition of the transformed phenotype (in most, if not all cases) resulted from disruption of the host btu1-1K350M gene, and negative paclitaxel selection based on BTU1 gene loss-of-function was nearly as effective as a positive selection based on paromomycin resistance conferred by the transgene.

TABLE I

Transformation of *T. thermophila* using biolistic bombardment

| Targeting Fragment | Selection method | Frequency (transf./µg DNA) |
|---|---|---|
| BTU1-2::neo1 | tx* | 115 |
| BTU1-2::neo1 | pm¶ | 204 |
| No DNA | tx | 0 |
| No DNA | pm | 0 |
| BTU1-2::neo1 | tx | 37 |
| BTU1-4::IAG[G1] | tx | 31 |
| No DNA | tx | 0 |

*30 µM paclitaxel.
¶120 µg/ml paromomycin.

Figure 5:
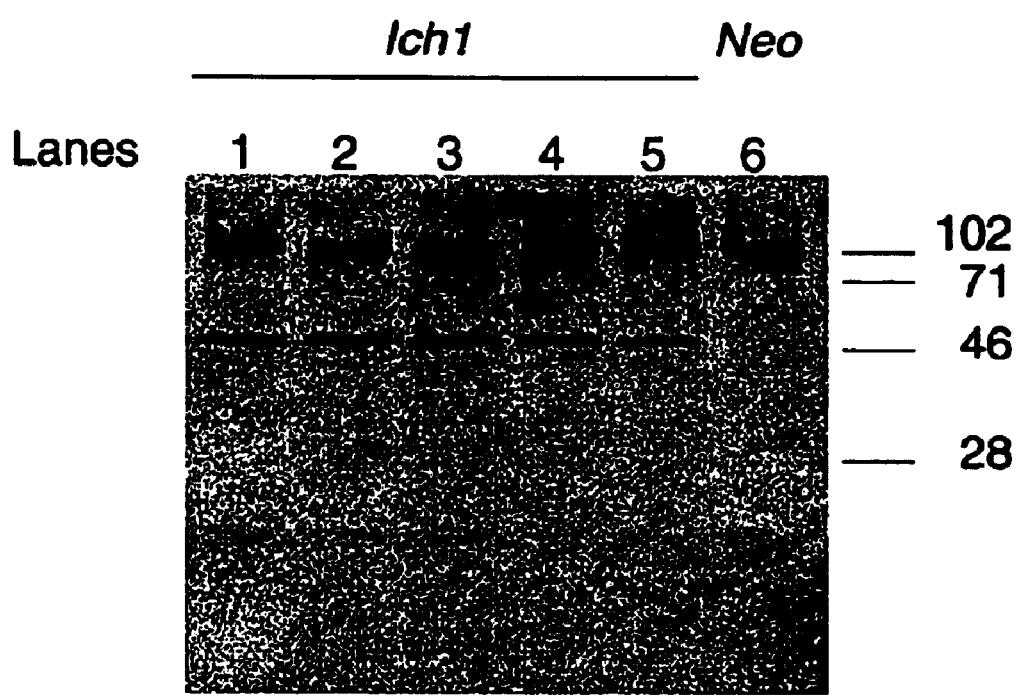

Unlike the bacterial neo gene, the product of the i-antigen gene of *I. multifiliis* is not inherently selectable. Nonetheless, as shown in Table I, paclitaxel-resistant transformants were obtained with a frequency comparable to that seen with the control BTU1-2::noe1 gene construct. Western blotting studies (FIG. 5) using polyclonal antiserum against affinity purified i-antigens of Ichthyophthirius showed that a protein of apparent MW of 50 kDa was detected in all transformants carrying the IAG48[G1] gene (lanes 1–5), but not in a control cell line transformed with noe1 (lane 6). The size of the detected protein was in close agreement with the MW of the corresponding surface antigen of chthyophthirius. An additional band of about 100 kDa seen in both BTU1-4::IAG48[G1] and control extracts, most likely represents an endogenous Tetrahymena protein that shares immunological determinants with the parasite antigen.

It should be noted that because the macronucleus of *T. thermophila* is polyploid and contains about 45 copies of each chromosome, only partial replacement of endogenous genes occurs following initial transformation. Nevertheless, chromosomes are distributed to daughter nuclei through an imprecise form of allelic segregation known as amitosis, and complete replacement of endogenous genes by transgenic copies can be achieved by continuous growth in selective media. In this case, PCR analysis revealed that about one half of endogenous copies of the BTU1 gene were replaced by the IAG48[G1] transgene during early stages of selection. Following growth in the presence of increasing concentrations of paclitaxel, however, endogenous copies of the BTU1 gene could no longer be detected, and a corresponding increase in the copy number of IAG48[G1] was seen, indicating that they had lost all copies of the endogenous BTU1 allele.

In Ichthyophthirius, the 48-kDa protein is a major component of the cell surface and is bound to ciliary and plasma membranes through a glycosylphosphatidylinositol (GPI) anchor. Nevertheless, the sequence elements responsible for membrane targeting in ciliates are not well-understood, and while Ichthyophthirius and Tetrahymena are taxonomically related, it was not know whether signal peptides from such widely diverged species could function interchangeably.

Figure 6A:
Figure 6B:
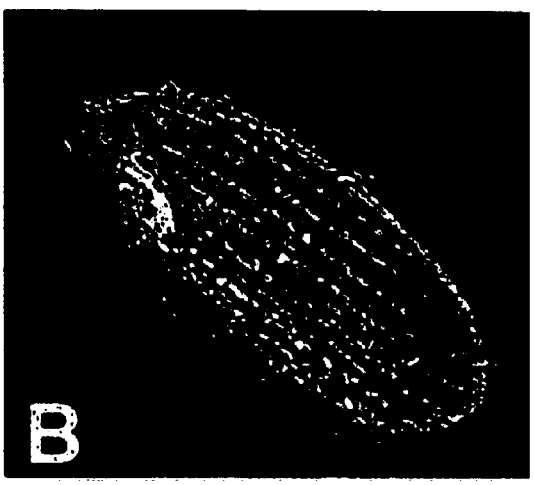
Figure 6C:
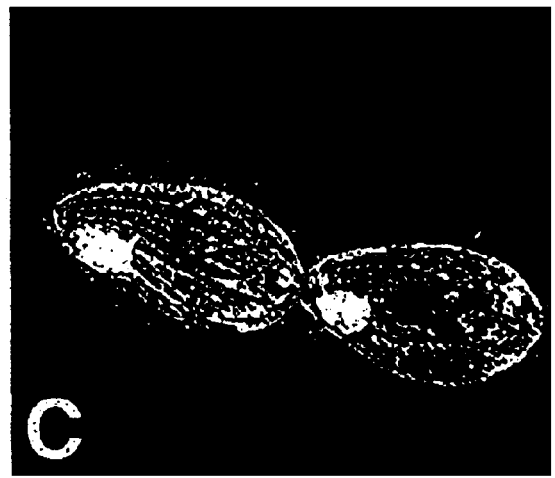
Figure 6D:

Transformed cell lines were therefore fixed (without permeabilization), reacted with antibodies against the 48-kDa antigen and analyzed for the presence of the *I. multifiliis* protein on their surface by indirect immunofluorescence using confocal microscopy. Strong labeling of oral and somatic cilia was observed (FIGS. 6A, 6B and 6C), wherein somatic cilia are shown in FIG. 6A and oral cilia are shown in FIG. 6C. Surface cortical fluorescence was seen in the form of longitudinal rows (shown in FIG. 6B). Dividing cells showed labeling in both the preexisting and newly formed oral apparatus, indicating that as the new structure is formed, parasite antigens are rapidly inserted into the cell membrane (FIG. 6C). Control cells (transformed with noe1) showed no obvious labeling (FIG. 6D). Fluorescence was only seen in controls when cells were permeabilized with methanol prior to fixation with paraformaldehyde. This appeared as a generalized background staining, and was not surprising given the presence of a cross-reacting (100 kDa) band in Western blots of control cell extracts.

A further demonstration of the presence of *I. multifiliis* proteins on the surface of Tetrahymena came from immobilization assays with living cells. In the immobilization assay, at antisera dilutions of 1:100 or less, rabbit antisera against the 48-kDa protein caused an immediate reduction in swimming velocity of the BTU1-4::IAG48[G1] transformants, followed by a complete loss of motility within 50 minutes. In contrast, noe1 transformants showed no immediate effect, but eventually became immobilized after 90 minutes. The difference in the response of BTU1-4::IAG48[G1] versus noe1 transformants indicates that *I. multifiliis* antigens are accessible to antibodies at the surface of live cells. Furthermore, because immobilizing antibodies recognize 3-dimensional epitopes on the 48 kDa protein, the antigen itself is likely to assume a native conformation in Tetrahymena.

Example III

Expression of Green Fluorescent Protein in Tetrahymena

Using the Tetrahymena BTU1 targeting system (Examples I and II), a modified version of the G1 i-antigen was constructed in which the green fluorescent protein (GFP) tag coding sequence was inserted in a correct frame into the G1 i-antigen of *I. multifiliis*, about 10 amino acids downstream from the site of cleavage of the N-terminal signal peptide. The G1-GFP construct was thereby targeted to the BTU1 locus, and transformants were selected with paclitaxel. The fusion protein was detected inside transformed cells using Western blotting and anti-gfp antibodies. A fraction of the fusion protein was found to be associated with the Triton X-114 extractable membranes of transformant cells, although no fusion protein was found on the cell surface.

Example IV

Expression of Malaria Surface Protein in Tetrahymena

Malaria is caused by parasitic protozoa of the genus Plasmodium, and is responsible for 2 million deaths a year worldwide. Current control efforts are focused on the mosquito vector, and treatment of the disease with anti-malarial drugs. No vaccine is yet available. Over the past four decades the parasite has become resistant to many anti-malarial drugs, and an effective vaccine is seen as best hope for controlling morbidity and mortality caused by this pathogen.

Most of the candidate molecules from Plasmodium suggested for inclusion in a vaccine are proteins that bind to receptors on host target cells. Necessary for vaccine development is the identification and characterization of the role played by these proteins. Unfortunately, this effort has been hampered by difficulties in procuring enough parasite protein to allow thorough study. Several heterologous expression systems have been utilized, but none has proven to be ideal, especially for the production of functional protein.

In this preliminary study, the Tetrahymena BTU1 targeting system (Examples I and II) was evaluated for use in expression of the *Plasmodium falciparum* surface proteins implicated in interactions with the host cells. A 1,900 bp region of a putative *P. falciparum* erythrocyte binding protein, EBL-1, was directly inserted in frame, at a NsiI restriction site, into the coding sequence of the G1 i-antigen of *I. multifiliis* flanked by the BTU1 targeting sequences. The resulting construct had a coding region encoding a chimeric fusion protein having the N-terminal portion of the i-antigen (representing about ⅔ of the i-antigen protein), followed by the EBL-1 domain encoded by the 1,900 bp region, followed by the C-terminal portion of the i-antigen (representing about ⅓ of the i-antigen protein), under control of the Tetrahymena BTU1 promoter.

This construct was expressed in Tetrahymena, demonstrating that the presence within the *P. falciparum* coding sequence of codons that are very rare in Tetrahymena did not abrogate expression. However, this EBL1::G1 fusion protein was expressed in Tetrahymena as a cytosolic protein, and no association with the cell membrane or the cell surface was observed despite the fact that the N-terminal and C-terminal targeting sequences of G1 i-antigen were present in the fusion protein. This result could be explained by improper folding of the multi-domain chimeric fusion protein; insertion of the EBL-1 coding sequence into the middle of the G1 i-antigen coding sequence arbitrarily divided the i-antigen sequence into two portions, possibly disrupting folding of the protein or otherwise interfering with the production of a protein that was competent to translocate into or across a membrane. A second experiment replacing the i-antigen coding sequence (between the two targeting sequences) with the EBL-1 domain instead of simply inserting it within the i-antigen coding sequence will provide more insight into targeted expression of EBL-1 in Tetrahymena.

Example V

Deletion of GPI Anchor Modification Domain

Figure 7A:
Figure 7B:
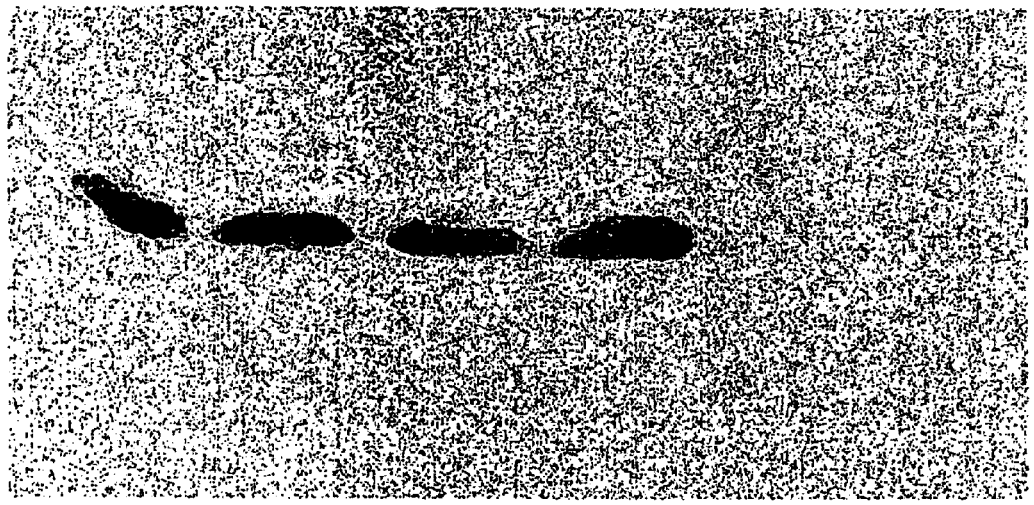

A truncated version of the G1 i-antigen gene from *I. multifiliis* was prepared in which the C-terminal domain implicated in the GPI anchor addition was deleted. The truncated gene was expressed in Tetrahymena as in Example II. FIG. 7 shows Western blots of total protein extracts of transformant cells (FIG. 7(a)) and total culture medium from which transformant cells were removed (FIG. 7(b)). The first four lanes from the left contained either cells (FIG. 7(a)) or culture medium (FIG. 7(b)) of four independent transformants of *T. thermophila* in which a truncated version of the G1 antigen lacking the GPI-anchoring C-terminal domain was incorporated into the BTU1 locus. Controls contained either the neo gene or a full-length G1 i-antigen of *I. multifiliis* expressed in the BTU1 locus. The amount of culture medium loaded (FIG. 7(b)) corresponds to about 1/30 of the amount of cells loaded (FIG. 7(a)). The truncated protein was expressed at essentially the same level observed for surface-targeted expression of the gene (Example II) (FIG. 7, top). However, about ½ of total expressed truncated G1 i-antigen protein was found in the culture medium, in contrast to the full length G1 i-antigen protein which was not detected in the culture medium. Thus, the elimination of the GPI anchor domain caused the i-antigen to be secreted out of the cell, as expected.

Example VI

Expression of Chicken Ovalbumin in Tetrahymena

Figure 8:
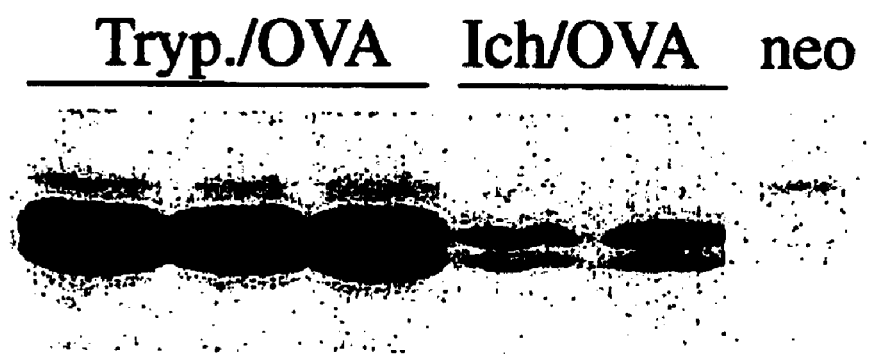

To test the feasibility of *Tetrahymena thermophila* for expression of vertebrate proteins, we prepared two constructs in which the region of the coding sequence of chicken ovalbumin protein (amino acids 139–385; GenBank Acc. Numbers M34346 and M25173; J. Catterall et al., *Nature* 275:510–513 (1978)) was fused to an N-terminal signal peptide of either the gp-72 surface protein of *T. cruzi* (Tryp./OVA) or of the G1 antigen of *I. multifiliis* (Ich/OVA) subcloned between the flanking sequences of the BTU1 gene of *T. thermophila*. These constructs were integrated into the BTU1 locus using biolistic transformation of the paclitaxel-sensitive host cells, and protein extracts of several paclitaxel-resistant transformants were analyzed by a Western blot using anti-chicken ovalbumin antibodies (Sigma Chemical Co.). Two protein bands close to the expected molecular weight of about 30 kD were detected in transformants but not in the negative control cells in which the BTU1 locus was transformed using the bacterial neomycin resistance gene (neo) (FIG. 8). The presence of two bands may be the result of posttranslational modifications or proteolysis in Tetrahymena. Interestingly, the fusion protein containing the signal peptide of *T. cruzi* gp72 protein was expressed at several fold higher level compared to the fusion protein with the *I. multifiliis* signal peptide. Also, it is striking that the levels of expression are extremely reproducible among individual transformants.

Example VII

Immune Response of Channel Catfish to Live Vaccine: Transformed Tetrahymena Expressing Full-length or Truncated *I. multifiliis* (Serotype A) 48 kD I-antigen Protein and Heterologous Challenge With *I. multifiliis* (Serotype D)

The IAG48[G1] gene of *Ichthyophthirius multifiliis* G1 encodes the GPI anchored 48-kDa i-antigen. The extreme 3' region of the gene encodes a stretch of 14 mostly hydrophobic amino acids separated by a short spacer from three small amino acids (CAS). This sequence encodes the protein's GPI anchor addition site. *Tetrahymena thermophila* cells transformed with the entire IAG48[G1] gene produce an intact i-antigen anchored to the cells' surface. Tetrahymena cells transformed with a modified IAG48[G1] gene construct lacking the 3' sequence which includes the GPI addition site would be expected to produce a truncated protein lacking the GPI anchor.

Figure 9:
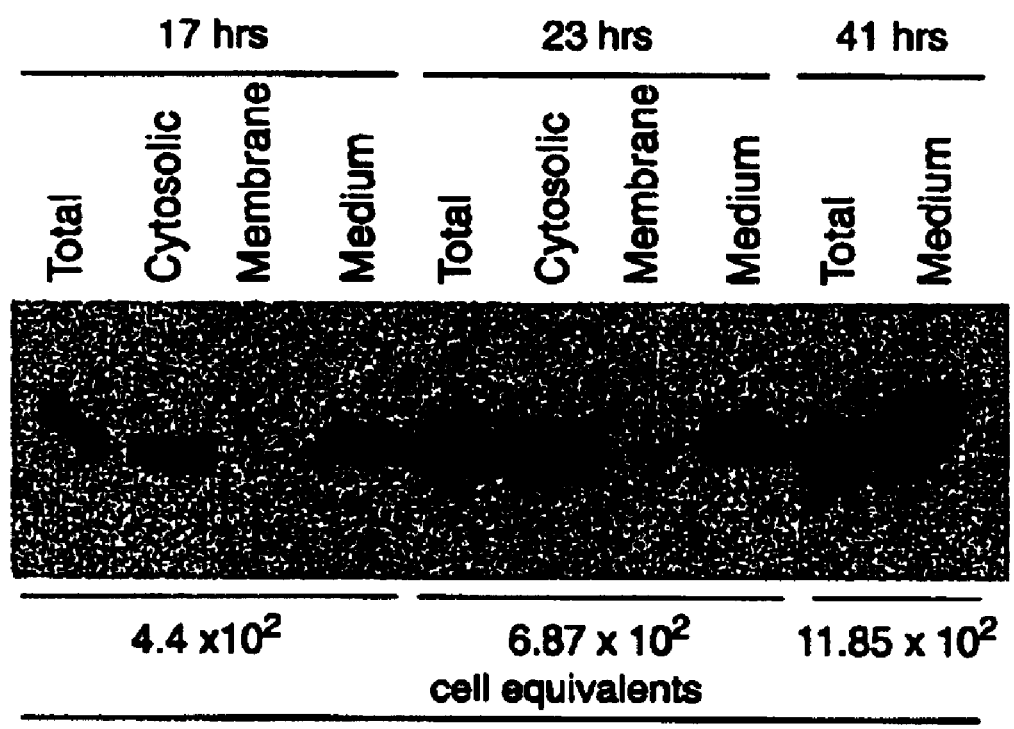

Tetrahymena cells were transformed with either the entire Ichthyophthirius G1 48-kDa i-antigen protein, or a truncated gene sequence which encodes the i-antigen protein lacking 19 amino acids at the carboxy terminus. Transformants encoding the intact or C-terminal truncated i-antigen were grown in standard Tetrahymena growth medium. Cell pellets and supernatant fluids were collected at the time points indicated. I-antigen was detected in cell cytosol, cell membrane or cell culture supernatants by Western blots using rabbit antisera against affinity purified Ichthyophthirius G5 i-antigen (see FIG. 9). It is clearly seen that the truncated protein is secreted into the culture medium.

Groups of channel catfish (6 fish per group) were immunized by bath exposure ($10^6$ or $10^5$ cells/fish) or intraperitoneal injection with *T. thermophila* transformants ($10^6$, $10^5$, or $10^4$ cells/fish) producing intact or truncated i-antigen. A third group of fish was immunized with membrane protein extracts (1 mg or 0.1 mg/fish) from *T. thermophila* producing the full length protein.

Immunization by bath exposure to Tetrahymena transformants. Two groups of fish (6 fish in each group) were immunized by bath exposure. The fish were exposed to either $10^6$ or $10^5$ cells/fish for a period of 24 hours. Two immunogens were used: 1) transformed Tetrahymena cells expressing the entire Ichthyophthirius G1 48-kDa protein, and 2) transformed cells secreting a truncated form of the i-antigen lacking the GPI anchor. Fish in the control group were exposed to Tetrahymena transformants expressing the neo1 gene product. Fish were exposed twice at a 30 day interval and challenged 30–60 days after the last immunization with the G5 Ichthyophthirius isolate. There were no significant differences (z test) between test and control groups (see Table 1). Immunized fish were challenged with a heterologous strain of Ichthyophthirius expressing a different i-antigen (serotype D; G5 isolate) than that produced by the recombinant Tetrahymena used for vaccination. It is expected that challenge with a strain of Ichthyophthirius producing an i-antigen homologous to the G1 48 i-antigen would show increased levels of protection.

TABLE 1

| | Vaccination by bath exposure | | | | | |
|---|---|---|---|---|---|---|
| Immunogen | Dose (cells/fish) | Number of fish challenged | Number of fish surviving | % survival | RSP[3] | MDD[4] ± SD[5] |
| Neo control | $10^6$ | 5 | 2 | 40 | N.A. | 17.0 ± 1.0 |
| TG1[1] | $10^5$ | 5 | 3 | 60 | 33.3 | 18.5 ± 2.1 |
| TG1 | $10^6$ | 6 | 3 | 50 | 25.0 | 13.3 ± 4.9 |
| sTG1[2] | $10^5$ | 6 | 3 | 50 | 25.0 | 21.0 ± 4.6 |
| sTG1 | $10^6$ | 6 | 4 | 66.7 | 40.0 | 17.0 ± 1.4 |

[1]Tetrahymena expressing intact membrane form of Ichthyophthirius G1 i-antigen.
[2]Tetrahymena secreting truncated form of G1 i-antigen.
[3]Relative Survival Percent = 1 - (number of dead fish in test group/number of dead fish in control group) × 100%
[4]Mean days to death
[5]Standard deviation Immunization by injection of Tetrahymena transformants. Fish in each group were injected intraperitoneally with $10^6$, $10^5$, or $10^4$ live transformed Tetrahymena cells/fish. The same immunogens and controls were tested as in the immersion vaccinations. Fish were injected two times at a 30 day interval, and challenged 21 days after the last immunization with G5 Ichthyophthirius. A greater degree of protection was elicited in immunized fish compared to controls (Table 2).

TABLE 2

| | | Vaccination by injection | | | | |
|---|---|---|---|---|---|---|
| Immunogen | Dose (cells/ fish) | Number of fish challenged | Number of fish surviving | % survival | RSP[3] | MDD[4] ± SD[5] |
| Neo control | 10[5] | 6 | 2 | 33.3 | N.A. | 15.3 ± 3.6 |
| TG1[1] | 10[6] | 5 | 3 | 60 | 44.5 | 19.0 ± 2.8 |
| TG1 | 10[5] | 5 | 4 | 80 | 58.4 | 15.0 ± 0.0 |
| TG1 | 10[4] | 6 | 2 | 33.3 | 0 | 14.0 ± 1.4 |
| sTG1[2] | 10[6] | 6 | 5 | 83.3 | 50.0 | 21.0 ± 4.6 |
| sTG1 | 10[5] | 6 | 3 | 50.0 | 25.0 | 20.0 ± 5.7 |

[1]Tetrahymena expressing intact membrane form of Ichthyophthirius G1 i-antigen.
[2]Tefrahymena secreting truncated from of G1 i-antigen.
[3]Relative Survival Percent = 1 − (number of dead fish in test group/ number of dead fish in control group) × 100%
[4]Mean days to death
[5]Standard deviation Serum antibody production. Fish serum antibody responses against recombinant G1 Ichthyophthirius i-antigen were determined by ELISA at 2, 4, and 6 weeks after immunization. Serum antibodies from immunized fish were detected with a sandwich ELISA technique that used wells coated with a cross-reactive rabbit antibody against Ichthyophthirius G5 i-antigen to capture recombinant G1 i-antigen produced in transformed Tetrahymena. Sera from test and control fish were added to wells and antibodies that bound to the captured i-antigen were detected using an alkaline phosphatase labeled mouse mAb against the immunoglobulin heavy chain of channel catfish. ELISA controls consisted of antibody-coated wells reacted with membrane protein from Tetrahymena cells transformed with the noe1 gene.

Figure 10A:
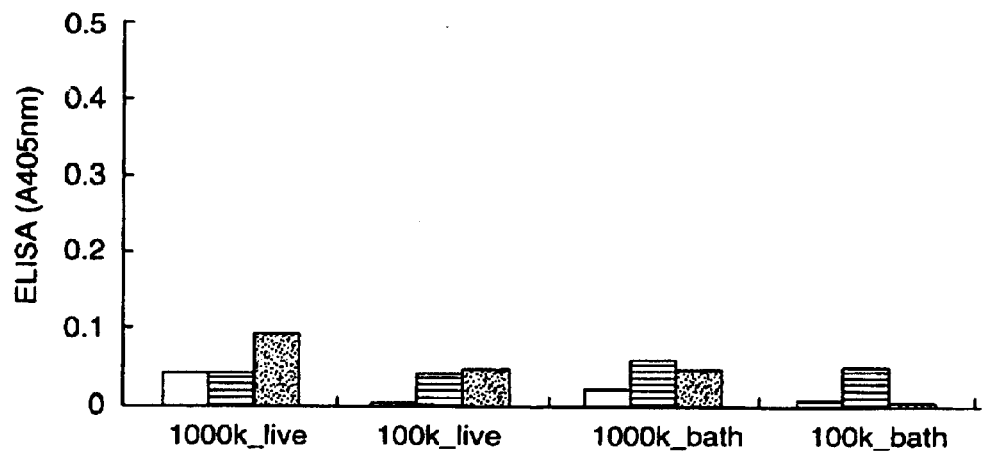
Figure 10B:
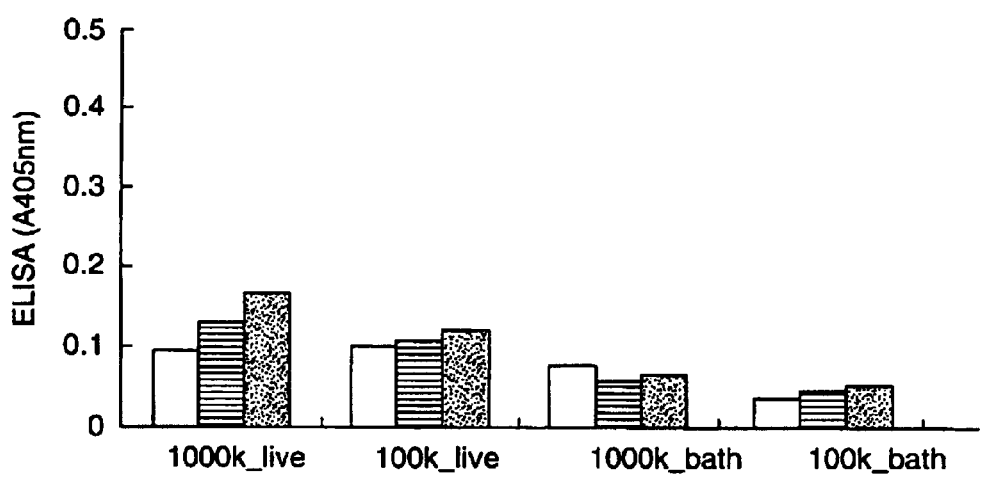

Fish injected with Tetrahymena membrane protein produced high levels of serum antibody against the recombinant i-antigen. The antibody response elicited by fish immunized with live cells was almost an order of magnitude lower. The antibody response of fish immunized by bath or i.p. injection with live cells secreting recombinant i-antigen was approximately two-fold greater than the antibody response of fish immunized with Tetrahymena producing the membrane-bound, intact i-antigen. In FIG. 10, the differences in antibody production between fish immunized with the (a) membrane associated or (b) secreted form of the i-antigen are shown. These results suggest that live cells secreting antigen are more efficacious in eliciting the production of serum antibodies. The mucosal antibody response was not determined in these experiments.

Example VIII

Immune Response of Channel Catfish to Live Vaccine: Transformed Tetrahymena Expressing Full-length or Truncated *I. multifiliis* (Serotype A) 48 kD I-antigen Protein and Homologous Challenge With *I. multifiliis* (Serotype A)

Tetrahymena cells were transformed with either the entire Ichthyophthirius G1 48- kDa i-antigen protein, or a truncated gene sequence which encodes the i-antigen protein lacking 19 amino acids at the carboxy terminus as in Example VII.

Groups of channel catfish (70 fish per group) were vaccinated by intraperitoneal injection with 10[6] *T. thermophila* transformants producing intact or truncated i-antigen. A third group of fish (control group) was vaccinated with *T. thermophila* transformants expressing neo. No adjuvant was used in any of the vaccinations. The fish were boosted 2 weeks following the initial injection and bled at 3 weeks following the initial injection. Sera from 3 fish per group were pooled.

Figure 11B:
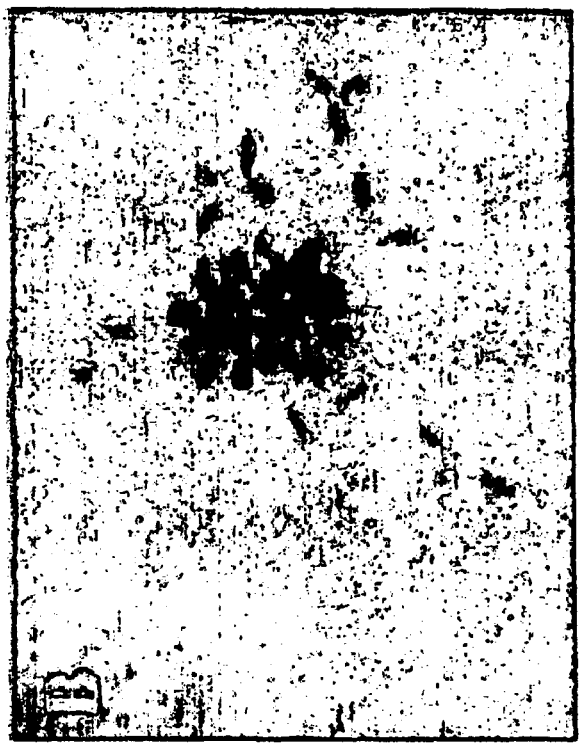
Figure 11A:

A 96 well ELISA plate was seeded with a homologous strain (i.e., serotype A) of *I. multifiliis* (strain NY1, a G1 isolate), 200 cells per well. Fish sera were serially diluted and added to the wells, and the effect on the motility of *I. multifiliis* was observed. Immobilization of *I. multifiliis* was immediately evident at serum dilutions of 1:20, and at higher concentrations the organisms exhibited clumping (see FIG. 11). Sera from the control group did not cause any detectable change in motility of *I. multifiliis*.

As another control, additional wells were seeded with a heterologous strain of *I. multifiliis* (a G5 isolate). The motility of these organisms was not affected by sera from any of the groups of vaccinated fish, confirming that the immobilization epitopes on *I. multifiliis* i-antigens are highly specific.

For comparison, two other groups of fish were vaccinated with purified subunit proteins produced from recombinant Tetrahymena (either the full-length 48 kD i-antigen protein or the C-terminal truncated version). The subunit proteins were adjuvanted with Freund's Complete Adjuvant. In a plate assay similar to the one described above using the homologous strain of *I. multifiliis*, some immobilization was observed but not to the degree caused by the "live vaccine." This observation lends support to the expectation that the "live vaccine" will prove to be more efficacious than the analogous protein subunit vaccine.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A recombinant protein expression system comprising:
a population of mutant protozoan host cells comprising a β-tubulin allele that confers paclitaxel sensitivity on the cells; and
a population of selectable transgenic protozoan host cells comprising a genomically integrated heterologous nucleic acid encoding a polypeptide wherein the genomically integrated heterologous nucleic acid disrupts the β-tubulin allele thereby restoring paclitaxel resistance to the selectable cells such that the selectable cells are selectable by negative selection using paclitaxel.

2. The recombinant protein expression system of claim 1 wherein the heterologous nucleic acid is from an organism that has an AT-rich genome having an AT content of more than about 50% of the total bases.

3. The recombinant protein expression system of claim 1 wherein the protozoan host cell is a Tetrahymena host cell comprising, prior to genomic integration of the heterologous nucleic acid, a btu1-1K350M β-tubulin allele.

4. A recombinant protein expression system comprising a transgenic ciliated protozoan host cell comprising a heterologous protein displayed on the plasma membrane surface of the host cell.

5. The recombinant protein expression system of claim 4 wherein the transgenic ciliated protozoan host cell is a Tetrahymena host cell.

6. The recombinant protein expression system of claim 4 wherein the surface-displayed heterologous protein comprises a GPI anchor encoded by a portion of an i-antigen-encoding nucleotide sequence from *I. multifiliis*.

7. An expression vector comprising a 5' flanking region followed by a heterologous nucleic acid encoding a polypeptide comprising at least one targeting amino acid sequence from an *I. multifiliis* i-antigen protein, followed by a 3' flanking region, wherein at least a portion of each of the 5' flanking region and the 3' flanking region is complementary to an endogenous gene of an intended host, so as to allow for integration of the heterologous nucleic acid into the endogenous gene by way of homologous recombination.

8. The expression vector of claim 7 wherein the 5' flanking region further comprises a promoter region operably linked to the heterologous nucleic acid sequence.

9. The expression vector of claim 7 wherein the 5' flanking region and the 3' flanking region each comprises a nucleic acid sequence selected from at least a portion of the Tetrahymena genes HHF1, rpl29, BTU1, BTU2, SerH3 and the gene encoding actin.

10. The expression vector of claim 7 wherein the at least one targeting amino acid sequence comprises a GPI cleavage/attachment sequence.

11. A transgenic *T. thermophila* comprising an *I. multifiliis* i-antigen protein or antigenic portion thereof.

12. The transgenic *T. thermophila* of claim 11 wherein the *I. multifiliis* i-antigen protein or antigenic portion thereof comprises a targeting amino acid sequence.

13. The transgenic *T. thermophila* of claim 12 wherein the targeting amino acid sequence comprises at least one of an N-terminal targeting sequence and a GPI cleavage/attachment sequence.

14. The transgenic *T. thermophila* of claim 11 wherein the *I. multifiliis* i-antigen protein or antigenic portion thereof is displayed on the surface of its plasma membrane.

15. A transgenic Tetrahymena cell comprising a heterologous protein comprising at least one targeting amino acid sequence from an *I. multifiliis* i-antigen protein.

16. The transgenic Tetrahymena cell of claim 15 wherein the targeting amino acid sequence comprises at least one of an N-terminal targeting sequence and a GPI cleavage/attachment sequence.

17. The transgenic Tetrahymena cell of claim 15 wherein the heterologous protein is displayed on the surface of the plasma membrane of the cell.

18. A vaccine comprising a transgenic nonpathogenic immunogenic protozoan comprising a heterologous surface-displayed antigenic polypeptide.

19. The vaccine of claim 18 comprising a live vaccine.

20. The vaccine of claim 18 comprising a killed vaccine.

21. The vaccine of claim 18 wherein the transgenic nonpathogenic immunogenic protozoan is a transgenic nonpathogenic immunogenic ciliated protozoan.

22. The vaccine of claim 21 wherein the transgenic nonpathogenic immunogenic ciliated protozoan is Tetrahymena.

23. The vaccine of claim 22 wherein the Tetrahymena comprises a btu1-1K350M locus into which a heterologous nucleic acid encoding the antigenic polypeptide has been inserted.

24. The vaccine of claim 18 wherein the antigenic polypeptide comprises at least an antigenic portion of an *I. multifiliis* i-antigen protein.

25. A recombinant method for producing a polypeptide comprising:
  (a) providing a population of mutant protozoan host cells comprising a β-tubulin allele that confers paclitaxel sensitivity on the cells;
  (b) introducing a heterologous nucleic acid encoding the polypeptide into the protozoan host cells such that it integrates into the genome of the protozoan host cells by disrupting the β-tubulin allele to yield a population of selectable transgenic protozoan host cells selectable by negative selection using paclitaxel; and
  (c) expressing the polypeptide in the selectable transgenic protozoan host cells.

26. The recombinant method of claim 25 wherein the protozoan host cell provided in step (a) is Tetrahymena.

27. The recombinant method of claim 26 wherein the Tetrahymena comprises a btu1-1K350M β-tubulin allele.

28. The recombinant method of claim 25 wherein the polypeptide is displayed on the plasma membrane of the transgenic protozoan host cell.

29. The recombinant method of claim 28 further comprising:
  (d) cleaving the polypeptide from the plasma membrane of the transgenic protozoan host cell.

30. The recombinant method of claim 25 wherein the polypeptide comprises at least one targeting amino acid sequence encoded by an i-antigen-encoding nucleotide sequence from *I. multifiliis*.

31. The recombinant method of claim 25 wherein the polypeptide is an antigenic polypeptide.

32. The recombinant method of claim 25 further comprising:
  (d) isolating the polypeptide from the transgenic protozoan host cell.

33. A recombinant method for producing a polypeptide comprising:
  (a) providing a ciliated protozoan host cell;
  (b) introducing a heterologous nucleic acid encoding the polypeptide into the protozoan host cell to yield a transgenic ciliated protozoan host cell; and
  (c) expressing the polypeptide in the transgenic ciliated protozoan host cell such that it is displayed on the plasma membrane surface of the host cell.

34. The recombinant method of claim 33 wherein the polypeptide comprises at least one targeting amino acid sequence encoded by an i-antigen-encoding nucleotide sequence from *I. multifiliis*.

35. The recombinant method of claim 33 further comprising:
  (d) cleaving the polypeptide from the plasma membrane surface of the transgenic host cell.

36. The recombinant method of claim 33 wherein the polypeptide is an antigenic polypeptide.

37. The recombinant method of claim 33 wherein the transgenic ciliated protozoan host cell is Tetrahymena.

38. A recombinant method for producing a polypeptide comprising:
  (a) providing a host cell;
  (b) introducing a heterologous nucleic acid encoding the polypeptide into the host cell to yield a transgenic host cell, wherein the polypeptide comprises at least one targeting amino acid sequence from an *I. multifiliis* i-antigen protein; and
  (c) expressing the polypeptide in the transgenic host cell.

39. The recombinant method of claim 38 wherein the at least one targeting amino acid sequence comprises at least one of an N-terminal targeting sequence and a GPI cleavage/attachment sequence.

40. The recombinant method of claim 38 wherein the at least one targeting amino acid sequence is from a 48 kD i-antigen of *I. multifiliis*.

41. The recombinant method of claim 38 wherein the at least one targeting amino acid sequence is from a 55 kD i-antigen of *I. multifiliis*.

42. A recombinant protein expression system comprising:
  a population of mutant Tetrahymena host cells comprising a β-tubulin allele that confers paclitaxel sensitivity on the cells; and
  a population of selectable transgenic Tetrahymena host cells comprising a genomically integrated heterologous nucleic acid encoding a polypeptide, wherein the heterologous nucleic acid is from a ciliate other than Tetrahymena, and wherein the genomically integrated heterologous nucleic acid disrupts the β-tubulin allele thereby restoring paclitaxel resistance to the selectable cells such that the selectable cells are selectable by negative selection using paclitaxel.

43. A recombinant protein expression system comprising:

a population of mutant protozoan host cells comprising a β-tubulin allele that confers paclitaxel sensitivity on the cells; and a population of selectable transgenic protozoan host cells comprising a genomically integrated heterologous nucleic acid encoding a polypeptide, wherein the genomically integrated heterologous nucleic acid disrupts the β-tubulin allele thereby restoring paclitaxel resistance to the selectable cells such that the selectable cells are selectable by negative selection using paclitaxel, and wherein the polypeptide comprises a targeting amino acid sequence that directs the polypeptide to the extracellular surface of plasma membrane of the cell for surface display.

44. A recombinant protein expression system comprising:

a population of mutant protozoan host cells comprising a β-tubulin allele that confers paclitaxel sensitivity on the cells; and a population of selectable transgenic protozoan host cells comprising a genomically integrated heterologous nucleic acid encoding a polypeptide, wherein the genomically integrated heterologous nucleic acid disrupts the β-tubulin allele thereby restoring paclitaxel resistance to the selectable cells such that the selectable cells are selectable by negative selection using paclitaxel, and wherein the polypeptide comprises a targeting amino acid sequence that directs the polypeptide to be secreted from the cell.

* * * * *

UNITED STATES PATENT AND TRADEMARK OFFICE
CERTIFICATE OF CORRECTION

PATENT NO. : 6,846,481 B1
DATED : January 25, 2005
INVENTOR(S) : Gaertig et al.

It is certified that error appears in the above-identified patent and that said Letters Patent is hereby corrected as shown below:

Column 2,
Line 38, delete "6:38-542" and insert -- 6:538-542 --

Column 20,
Lines 58 and 60, delete "noe1" and insert -- neo1 --

Column 21,
Lines 4, 14 and 17, delete "noe1" and insert -- neo1 --
Lines 15 and 27, delete "HindIII" and insert -- Hind III --
Line 22, delete "(5°" and insert -- (5' --
Line 28, delete "BamHI" and insert -- BamH I --
Line 32, delete "HindIII and BamHI" and insert -- Hind III and BamH I --
Line 33, delete "BasmHi-HindIII" and insert -- BamH I-Hind III --

Column 22,
Line 3, delete "SacI and SalI" and insert -- Sac I and Sal I --
Line 4, delete "noe1" and insert -- neo1 --

Column 23,
Line 47, delete "noe1" and insert -- neo1 --

Column 24,
Lines 20 and 25, delete "noe1" and insert -- neo1 --

Column 25,
Line 19, delete "noe1" and insert -- neo1 --

Column 28,
Line 31, delete "noe1" and insert -- neo1 --

UNITED STATES PATENT AND TRADEMARK OFFICE
CERTIFICATE OF CORRECTION

PATENT NO. : 6,846,481 B1
DATED : January 25, 2005
INVENTOR(S) : Gaertig et al.

It is certified that error appears in the above-identified patent and that said Letters Patent is hereby corrected as shown below:

Column 29,
Line 35, delete "noe1" and insert -- neo1 --

Signed and Sealed this

Seventh Day of June, 2005

JON W. DUDAS
*Director of the United States Patent and Trademark Office*